United States Patent
Wildhirt et al.

(10) Patent No.: US 11,712,511 B2
(45) Date of Patent: Aug. 1, 2023

(54) IMPLANTABLE DEVICE FOR THE LOCATIONALLY ACCURATE DELIVERY AND ADMINISTRATION OF SUBSTANCES INTO THE PERICARDIUM OR ONTO THE SURFACE OF THE HEART

(71) Applicant: AdjuCor GmbH, Munich (DE)

(72) Inventors: Stephen Manuel Wildhirt, Munich (DE); Andreas Maier, Grafing bei Muenchen (DE); Kei Wieland Muller, Munich (DE); Bjorn Hofmann, Oberding (DE)

(73) Assignee: AdjuCor GmbH, Munich (DE)

( * ) Notice: Subject to any disclaimer, the term of this patent is extended or adjusted under 35 U.S.C. 154(b) by 0 days.

(21) Appl. No.: 16/709,716

(22) Filed: Dec. 10, 2019

(65) Prior Publication Data

US 2020/0375742 A1 Dec. 3, 2020

Related U.S. Application Data

(63) Continuation of application No. 14/794,459, filed on Jul. 8, 2015, now abandoned.

(30) Foreign Application Priority Data

Jul. 7, 2015 (DE) .......................... 102015212699.4

(51) Int. Cl.
*A61M 5/14* (2006.01)
*A61F 2/24* (2006.01)
(Continued)

(52) U.S. Cl.
CPC ............. *A61M 5/14* (2013.01); *A61F 2/2481* (2013.01); *A61M 5/14276* (2013.01);
(Continued)

(58) Field of Classification Search
CPC ................ A61M 5/14; A61M 5/14276; A61M 2205/04; A61M 2210/122;
(Continued)

(56) References Cited

U.S. PATENT DOCUMENTS 5,490,820 A 2/1996 Schock et al.
5,749,839 A 5/1998 Kovacs
(Continued)

FOREIGN PATENT DOCUMENTS

DE 69427906 4/2002
DE 102009043795 11/2012
(Continued)

OTHER PUBLICATIONS

World Health Organization. (2013). World health statistics 2013. World Health Organization. http://www.who.int/iris/handle/10665/81965. (Reference submitted in an IDS in Parent U.S. Appl. No. 14/794,459.).
(Continued)

*Primary Examiner* — Shefali D Patel
(74) *Attorney, Agent, or Firm* — Gardella Grace P.A.

(57) ABSTRACT

A device for administration of substances onto an epicardial surface of a heart includes a frame structure for at least partially encircling a circumference of the heart which is able to assume shaping, positioning, guiding and stabilizing functions. The frame structure may be coupled to a heart-shaped sleeve. A substance carrier for accommodating the substances to be administered may be coupled to the device.

21 Claims, 18 Drawing Sheets

(51) Int. Cl.
*A61M 5/142* (2006.01)
*A61L 31/14* (2006.01)
*A61L 31/16* (2006.01)
*A61L 31/00* (2006.01)
*A61M 5/172* (2006.01)

(52) U.S. Cl.
CPC .......... *A61F 2002/2484* (2013.01); *A61F 2230/0067* (2013.01); *A61F 2240/001* (2013.01); *A61F 2250/0068* (2013.01); *A61L 31/005* (2013.01); *A61L 31/146* (2013.01); *A61L 31/148* (2013.01); *A61L 31/16* (2013.01); *A61L 2300/60* (2013.01); *A61L 2300/64* (2013.01); *A61L 2430/20* (2013.01); *A61M 5/1723* (2013.01); *A61M 2205/04* (2013.01); *A61M 2205/05* (2013.01); *A61M 2210/122* (2013.01); *A61M 2210/125* (2013.01)

(58) Field of Classification Search
CPC .......... A61M 2210/125; A61M 5/1723; A61M 60/289; A61M 60/465; A61M 60/468; A61M 60/839; A61M 60/90; A61F 2/2481; A61F 2230/0067; A61F 2250/0003; A61F 2250/0067; A61F 2250/0068; A61F 2/24; A61F 2/2409; A61F 2/2478; A61F 2002/2484; A61F 2230/0063; A61F 2230/0093; A61F 2205/0003; A61F 2205/0067; A61F 2205/0068; A61F 2240/001; A61L 31/146; A61L 31/148; A61L 31/16; A61L 2300/60; A61L 2430/20
See application file for complete search history.

(56) References Cited

U.S. PATENT DOCUMENTS

| | | |
|---|---|---|
| 6,612,979 B2 | 9/2003 | Lau et al. |
| 6,626,821 B1 | 9/2003 | Kung et al. |
| 6,659,950 B2 | 12/2003 | Taheri |
| 7,637,880 B2 * | 12/2009 | Ferrari .......... A61M 60/289 601/153 |
| 8,372,054 B2 | 2/2013 | Duffy et al. |
| 8,944,987 B2 | 2/2015 | Meister et al. |
| 2003/0229260 A1 | 12/2003 | Girard et al. |
| 2004/0267329 A1 | 12/2004 | Raman et al. |
| 2005/0107661 A1 | 5/2005 | Lau et al. |
| 2006/0167334 A1 | 7/2006 | Anstadt et al. |
| 2006/0217774 A1 | 9/2006 | Mower et al. |
| 2007/0065414 A1 | 3/2007 | Freyman et al. |
| 2007/0197859 A1 | 8/2007 | Schaer et al. |
| 2007/0225545 A1 | 9/2007 | Ferrari |
| 2008/0021266 A1 | 1/2008 | Laham et al. |
| 2008/0319255 A1 | 12/2008 | Cohn et al. |
| 2009/0036730 A1 | 2/2009 | Criscione et al. |
| 2009/0285787 A1 | 11/2009 | Minguell et al. |
| 2010/0030017 A1 | 2/2010 | Baker et al. |
| 2010/0152523 A1 | 6/2010 | MacDonald et al. |
| 2010/0168713 A1 | 7/2010 | Tkebuchava |
| 2010/0256441 A1 | 10/2010 | Lu et al. |
| 2011/0021864 A1 | 1/2011 | Criscione et al. |
| 2012/0142996 A1 | 6/2012 | Criscione |
| 2012/0157751 A1 | 6/2012 | Consigny et al. |
| 2012/0283506 A1 | 11/2012 | Meister et al. |
| 2014/0072611 A1 | 3/2014 | Maslowski |
| 2014/0194717 A1 | 7/2014 | Wildhirt et al. |

FOREIGN PATENT DOCUMENTS

| | | |
|---|---|---|
| DE | 102013200154 | 7/2014 |
| EP | 2752208 | 7/2014 |
| EP | 2482865 | 5/2015 |
| WO | 2000/25842 | 5/2000 |

OTHER PUBLICATIONS

Sasaki, D. & Okano, T. (2011). Cardiac Differentiation of Embryonic Stem Cells by Patterning Culture, Embryonic Stem Cells—Recent Advances in Pluripotent Stem Cell-Based Regenerative Medicine, Prof. Craig Atwood (Ed.), ISBN: 978-953-307-198-5, InTech, pp. 65-80, <http://www.intechopen.com/books/embryonic-stem-cells-recent-advances-in-pluripotent-stem-cell-basedregenerative-medicine/cardiac-differentiation-of-embryonic-stem-cells-by-patterning-culture> (Reference submitted in an IDS in Parent U.S. Appl. No. 14/794,459.).

Jawad, H., Lyon, A.R., Harding, S.E., Ali, N.N., & Boccaccini, A.R.; Myocardial tissue engineering, British Medical Bulletin, vol. 87, Issue 1, Sep. 1, 2008, pp. 31-47, https://doi.org/10.1093/bmb/ldn026. (Reference submitted in an IDS in Parent U.S. Appl. No. 14/794,459.).

Vizzardi, E., Lorusso, R., De Cicco, G., Zanini, G D'Aloia, A., & Dei Cas, L. (2012). Stem cells and repair of the heart: Cell-releasing epicardial scaffolds. The Journal of cardiovascular surgery. vol. 53—No. 5, pp. 685-689. (Reference submitted in an IDS in Parent U.S. Appl. No. 14/794,459.).

Hou, D., Youssef, E.A., Brinton, T.J., Zhang, P., Rogers, P.I., Price, E.T., Yeung, A., Johnstone, B., Yock, P.G., & March, K.L. (2005). Radiolabeled cell distribution after intramyocardial, intracoronary, and interstitial retrograde coronary venous delivery: implications for current clinical trials. Circulation, 112 9 Suppl, pp. I150-I156. (Reference submitted in an IDS in Parent U.S. Appl. No. 14/794,459.).

Christoforou, N., Liau, B., Chakraborty, S., Chellapan, M., Bursac N., & Leong, K.W. (2013). Induced Pluripotent Stem Cell-Derived Cardiac Progenitors Differentiate to Cardiomyocytes and Form Biosynthetic Tissues. PLOS ONE 8(6): e65963. https://doi.org/10.1371/journal.pone.0065963. (Reference submitted in an IDS in Parent U.S. Appl. No. 14/794,459.).

Behfar, A., & Terzic, A. (2006). Derivation of a cardiopoietic population from human mesenchymal stem cells yields cardiac progeny. Nature Clinical Practice Cardiovascular Medicine, 3(SUPPL. 1), pp. 78-82. https://doi.org/10.1038/ncpcardio0429. (Reference submitted in an IDS in Parent U.S. Appl. No. 14/794,459.).

Korf-Klingebiel, M., Reboll, M., Klede, S., Brod, T., Pich, A., Polten, F., Napp, L.C., Bauersachs, J., Ganser, A., Brinkmann, E., Reimann, I., Kempf, T., Niessen, H.W., Mizrahi, J., Schonfeld, H., Iglesias, A., Bobadilla, M., Wang, Y., & Wollert, K.C. (2015). Myeloid-derived growth factor (C19orf10) mediates cardiac repair following myocardial infarction. Nature medicine. 21. 10.1038/nm. 3778. (Reference submitted in an IDS in Parent U.S. Appl. No. 14/794,459.).

Maier, Thomas, "Multiple couplings are flexible," all-electronics. de, Aug. 30, 2012, https://www.all-electronics.de/mehrfachkupplungen-zeigen-sich-flexibel/#. (Reference submitted in an IDS in Parent U.S. Appl. No. 14/794,459.).

* cited by examiner

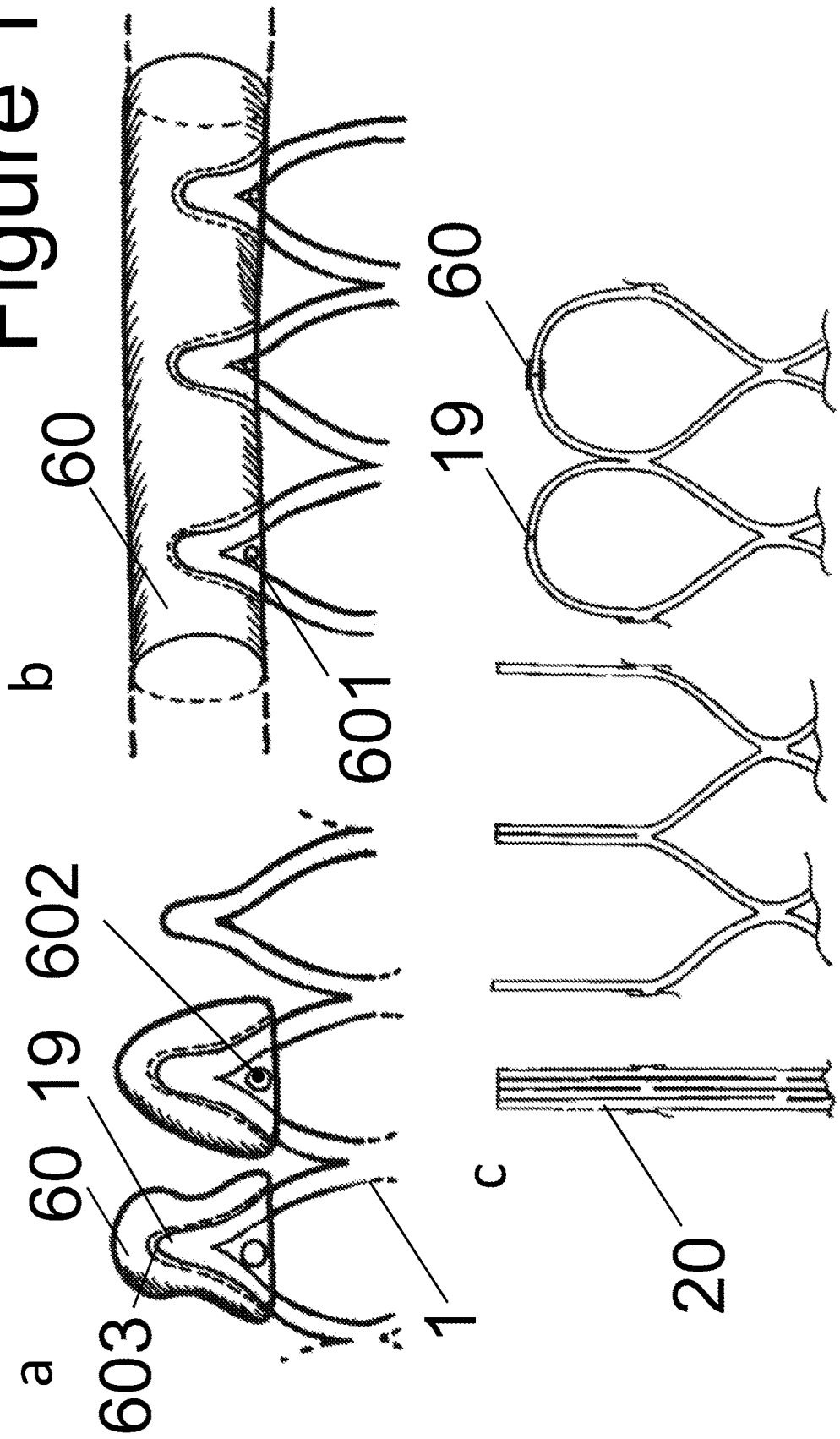

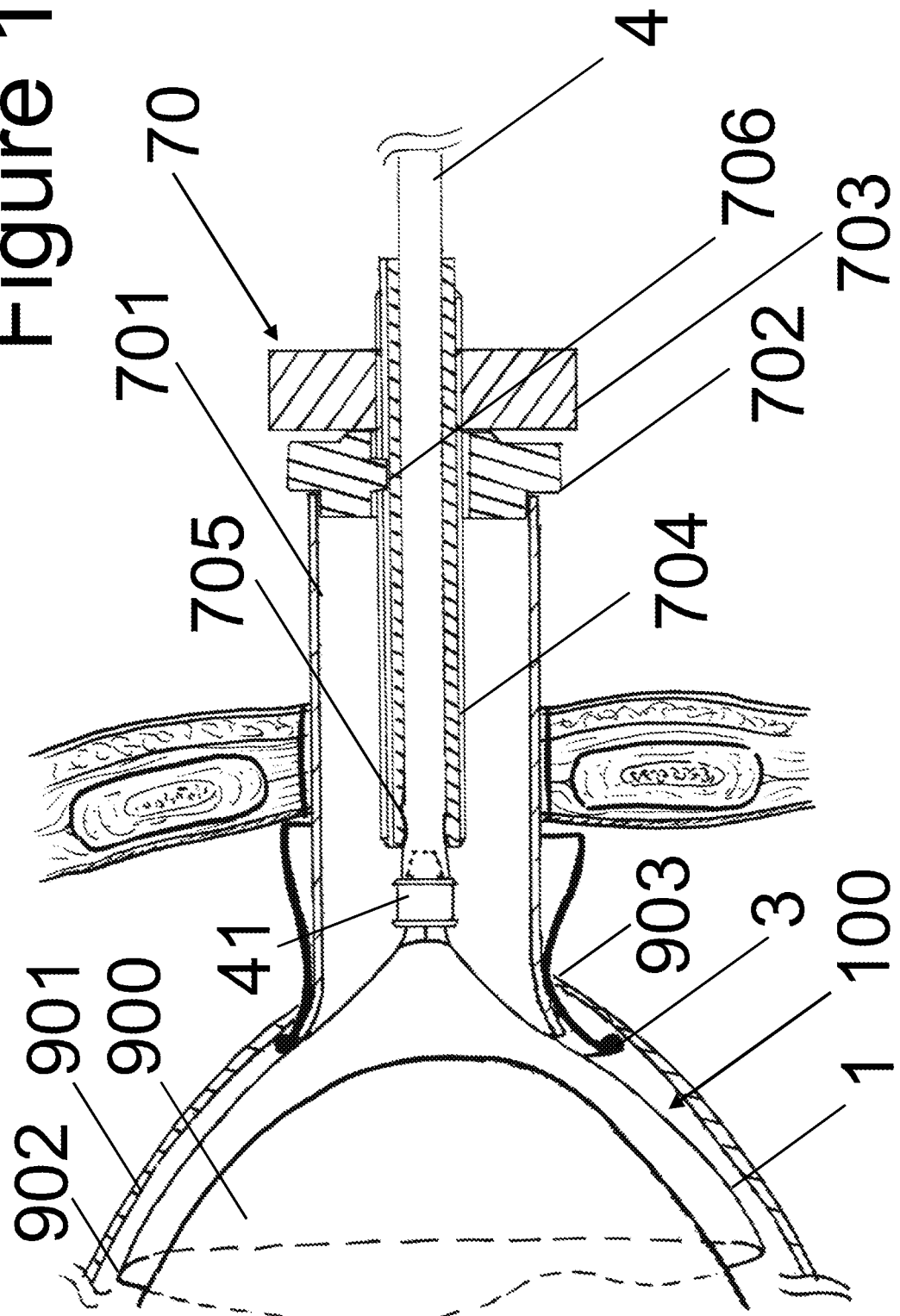

IMPLANTABLE DEVICE FOR THE LOCATIONALLY ACCURATE DELIVERY AND ADMINISTRATION OF SUBSTANCES INTO THE PERICARDIUM OR ONTO THE SURFACE OF THE HEART

PRIORITY CLAIM

The present application is a continuation application of U.S. application Ser. No. 14/794,459, filed Jul. 8, 2015, which claims priority to German patent application serial no. DE 102015212699.4, filed Jul. 7, 2015, the entire contents of which are incorporated herein by reference and relied upon.

BACKGROUND

The invention is for use in the treatment of cardiac insufficiency, for example following previous myocardial infarction. It is intended to support the pumping function of the heart, increase it or regenerate damaged heart tissue and hence to reduce insufficiency over the medium and long term or prevent the terminal stage being reached.

Cardiovascular diseases such as terminal cardiac insufficiency or myocardial infarction are the main cause of death worldwide (Behfar, A. and A. Terzic. Nature clinical practice Cardiovascular medicine 3 Suppl 1, pp. 78-82, 2006). 32% of worldwide deaths are the result of cardiovascular diseases (World Health Statistics, http://apps.who.int/iris/bitstream/10665/81965/1/9789241564588_eng.pdf (2013)2013). 40% of all deaths in Germany are attributable to cardiovascular diseases (German Federal Office of Statistics, https://www.destatis.de/DE/Publikationen/Thematisch/Gesundheit/Todesursachen/To desursachen.html, 2013). In the USA, around a million people a year suffer a heart attack and six million suffer resulting cardiac insufficiency; the direct and indirect costs of this are estimated at 180 billion dollars a year (Christoforou et al., Plos One 8, 17, 2013). The medical, societal and economic implications are enormous and are set to increase worldwide over the coming years as a result of our growing prosperity, the lifestyle associated with it and demographic growth.

Cardiac insufficiency is described as a restriction of the pumping function of the heart. The primary symptom is reduced pumping performance of the heart. The deterioration in performance is compensated for by an increase in the volume of the heart. As a result, the thickness of the wall of the heart decreases, contractility falls and pumping performance therefore declines further. This downward spiral culminates in heart failure or the failure of other organs owing to a lack of oxygen and nutrients.

The various manifestations of cardiac insufficiency can be treated through medication (for example through administration of beta blockers) or by carrying out an operation. The only treatment option for terminal cardiac insufficiency is a heart transplant. However, there is a large demand for donor hearts and only insufficient supply (Sasaki, D. and T. Okano, Embryonic Stem Cells-Recent Advances in Pluripotent Stem Cell-Based Regenerative Medicine, 65-80, 2011). Pacemakers can compensate for disruptions in stimulus conduction, prostheses can replace defective heart valves and blood pumps (for example ventricular assist devices, VADs) can improve the performance of insufficient hearts. However, the above methods only delay the development of insufficiency, they do not stop it or cure the disease (Christoforou et al., 2013). A treatment which addresses the various causes of cardiac insufficiency is to support the pumping function of the heart by means of an implant which exerts a mechanical pressure on the heart and thereby improves its pumping performance not only immediately but also over the medium and long term.

For example, cardiac insufficiency may develop as a result of a heart attack. In a heart attack, the sudden closure of at least one coronary artery leads to the death of heart muscle cells. The limited ability of the damaged heart muscle tissue to regenerate prevents full and independent recovery. Instead, dead tissue is replaced by scar tissue which is unable to contract. The pumping performance of the heart deteriorates and the spiral of degeneration described above begins.

There is a medical, societal and economic need to develop effective, regenerative forms of treatment which support and increase the existing pumping function of the heart, prevent the formation of scar tissue following a heart attack, promote the regeneration of heart muscle cells and consequently prevent terminal cardiac insufficiency and heart failure.

Previously known mechanical cardiac support devices are disclosed, for example, in U.S. Pat. No. 5,749,839 B1 and U.S. Pat. No. 6,626,821 B1 and in WO application 00/25842. They disclose devices which have the disadvantage that their implantation requires an open-chest operation. They are also complex and can only be implanted by means of a complicated surgical operation. They are integrated into the bloodstream of the patient. Improved centrifugal pumps or magnetically mounted impeller systems continually convey the blood. Contact between the blood and the exogenous surfaces of the systems is a considerable technical and medical challenge. Common complications of these systems are strokes, internal bleeding and infections. They often result in long-term hospitalization and frequent readmission of patients who have just been released from hospital.

Other known cardiac support devices, such as the devices disclosed in US 2008/0021266 A1, DE 10 2009 043 795 A1, US 2004/0267329 A1, US 2005/0107661 A1, US 2006/0217774 A1, US 2007/0197859 A1, US 2009/0036730 A1, US 2011/0021864 A1, U.S. Pat. No. 8,944,987 B2 and EP 2482865 B1, have the disadvantage that no embodiments exist which prevent the spatial impairment of the inferior vena cava by the implanted device. The inferior vena cava opens from the back into the right atrium. Spatial impairment of the inferior vena cava by the device would lead to inferior cava syndrome (obstruction of the filling of the right atrium). A further disadvantage of known cardiac support systems is that no precautions are taken against dislocation of the device in relation to the heart. Dislocation leads to a poorer fit of the device to the heart and to a loss of support. Nor are any of these devices self-expanding, that is to say they can only be put into their target position, in which they surround the heart, with the aid of further devices.

Other known cardiac support systems, such as the devices disclosed in EP 2752208 A1, are self-expanding and have a recess which prevents the inferior vena cava or other anatomical features near the heart from being spatially impaired, but they lack the ability to administer substances, such as pharmaceutical active agents, locationally accurately and in a targeted manner onto the epicardium.

A promising approach to the regenerative treatment of ischaemic tissue after a heart attack is through treatment with stem cells (Vizzardi, E. et al. J. Card. Surg., 53, 685-689, 2012) or with what are referred to as growth factors (Korf-Klingebiel, M. et al., Nature Medicine 21, 52-61, 2015). Under certain conditions, stem cells can identify cardiomyocytes and replaced dead cells (Sasaki and Okano, 2011). Stem cells have hitherto with little therapeutic success primarily been injected into the bloodstream (US 2009/0285787 A1) or released in the coronary artery via a catheter (U.S. Pat. No. 8,372,054 B2, US 20070065414 A1, US 20120157751 A1, US 20140072611 A1). Only a small proportion of cells (~3%) or other therapeutic substances reaches the target location (Hou, D. M. et al. Circulation 112, 1150-1156, 2005). Injecting cells into the coronary artery can lead to the artery becoming blocked. All of the above methods work by releasing cells or therapeutic substances in the bloodstream which may lead to internal bleeding, infections, thrombus formation and hence heart attacks and strokes. Another form of administration is the injection of cells into the myocardium (U.S. Pat. No. 6,659, 950 B2, US 20100168713 A1). Because of the movement of the heart, these methods carry a high risk of tissue or vascular damage and of wrongly administered injections without resulting in more successful treatment (Jawad, H., A. R. Lyon, S. E. Harding, N. N. Ali and A. R. Boccaccini, 2008, Myocardial tissue engineering. British Medical Bulletin, 87, 31-47). In order to increase therapeutic efficiency, it is also often necessary to administer, in addition, chemical signalling substances in a temporally and locationally defined manner, which is impossible using said methods. None of the disclosed devices can administer substances via an implantable device into the pericardial cavity or onto the surface of the heart. Nor can any of the disclosed devices deliver or remove substances already administered to the pericardial cavity after implantation.

A device which overcomes all of these disadvantages is described here. The present invention relates to a device for supporting and restoring the function of a heart. One aspect of the invention is a device for the locationally accurate delivery of substances onto the surface of the heart or into the pericardial cavity, which does not have the disadvantages of the known devices and/or methods for the administration of therapeutic substances for the regeneration of ischaemic heart tissue after a myocardial infarction. The device may be implanted minimally invasively with the aid of a catheter. It is not inserted into any vascular system and therefore does not permanently come into direct contact with the blood, which considerably reduces the risk of infection, thrombus formation and internal bleeding compared to other systems for administering substances for the regeneration of ischaemic tissue after a heart attack. The device may remain in the body for a certain amount of time and be explanted minimally invasively after treatment has come to an end.

SUMMARY OF THE INVENTION

The device for administering a substance to a surface of the heart comprises a frame structure, a sleeve, a substance carrier and a substance to be administered. The device may also comprise an expandable unit which is mounted at, in or on the sleeve. The expandable unit may also be part of the sleeve. The substance carrier may be mounted on the expandable unit or on the sleeve. Mounting the substance carrier on the expandable unit allows administration of the substance with the simultaneous exertion of pressure onto the surface of the heart.

The frame structure may be reversibly self-expanding. It may be incorporated minimally invasively into the body and may at least partially surround a heart in its expanded state.

The substance carrier may be a pocket. The substance to be administered may be inserted into the pocket. The substance may be inserted directly into the pocket or be applied to a carrier which is inserted into the pocket.

The pocket may have a removal area on the surface of the pocket facing the heart. In some embodiments, the removable area may be removed from outside the body after implantation of the device. The removable area may be at least partially biodegradable. The pocket may also comprise a permeable area.

The substance carrier may have a delivery line for filling and emptying the substance carrier with a substance to be administered. The substance carrier may have a spongy or porous structure. This increases the surface area and storage capacity of the substance carrier. Such a structure is also advantageous when administering cells because cells adhere and/or proliferate better in such structures.

The sleeve may be affixed to the frame structure. The device may be implanted minimally invasively. The frame structure may also be made out of wire, in particular out of a wire comprising a shape memory alloy.

The substance to be administered may be a pharmaceutical active agent. The substance to be administered may additionally or alternatively comprise cells.

Embodiments of the present invention comprise a supply unit. This may comprise a substance reservoir.

A further aspect of the invention relates to a device for implanting the device. The device for implanting may comprise a tubular delivery system. The tubular delivery system may have a distal end face which is slanted. This may facilitate implantation.

A further aspect of the invention relates to a device for explanting the device. The device for explanting may comprise a cylindrical tube, wherein the cylindrical tube is able to comprise a radial widening at the distal end. This explantation device is able to allow the removal of the implant minimally invasively from the pericardial cavity A further aspect relates to a method for producing a device for the administration of a substance onto a surface of the heart. The method comprises the steps of providing a frame structure, mounting a sleeve on the frame structure, mounting a substance carrier and filling the substance carrier with a substance to be administered. The substance carrier may be mounted on the sleeve. The device may comprise an expandable unit. The substance carrier may be mounted on the expandable unit.

The device for the administration of a substance onto a surface of the heart may comprise further components. For example, lines may be provided for delivering and discharging the substance to be administered. Mechanical forces may also be exerted on the administered substances or the epicardial heart surface of the myocardium. The forces may be built up by the expandable units. Alternatively or in addition, forces may be built up on the substance carrier which improve administration.

A further aspect relates to a motor unit which, by means of an electric motor, drives a pressure reservoir of variable volume in order to set the degree of expansion of the at least one expandable unit.

Furthermore, some embodiments of the device according to the invention may be energetically passive, that is to say they function without any energy supplied from outside and/or inside the body.

A further aspect of the device according to the invention is the fact that it may have devices which minimize the risk of damage to the surrounding tissue caused by pointed or sharp-edged components of the frame structure produced in the manufacturing process.

Further embodiments and advantages are disclosed in the detailed description.

DESCRIPTION OF THE DRAWINGS

FIG. 17 shows various embodiments of end fittings and a frame structure geometry which minimize the risk of damage to the body tissue caused by the frame structure or the risk of the frame structure penetrating the sleeve at least partially surrounding it.

FIG. 18 shows an apparatus for explanting the device minimally invasively during the explantation process.

DETAILED DESCRIPTION

Embodiments of the invention comprise several components which are explained in more detail in the following sections, it being possible for embodiments of the individual components to be combined with one another.

Figure 1:
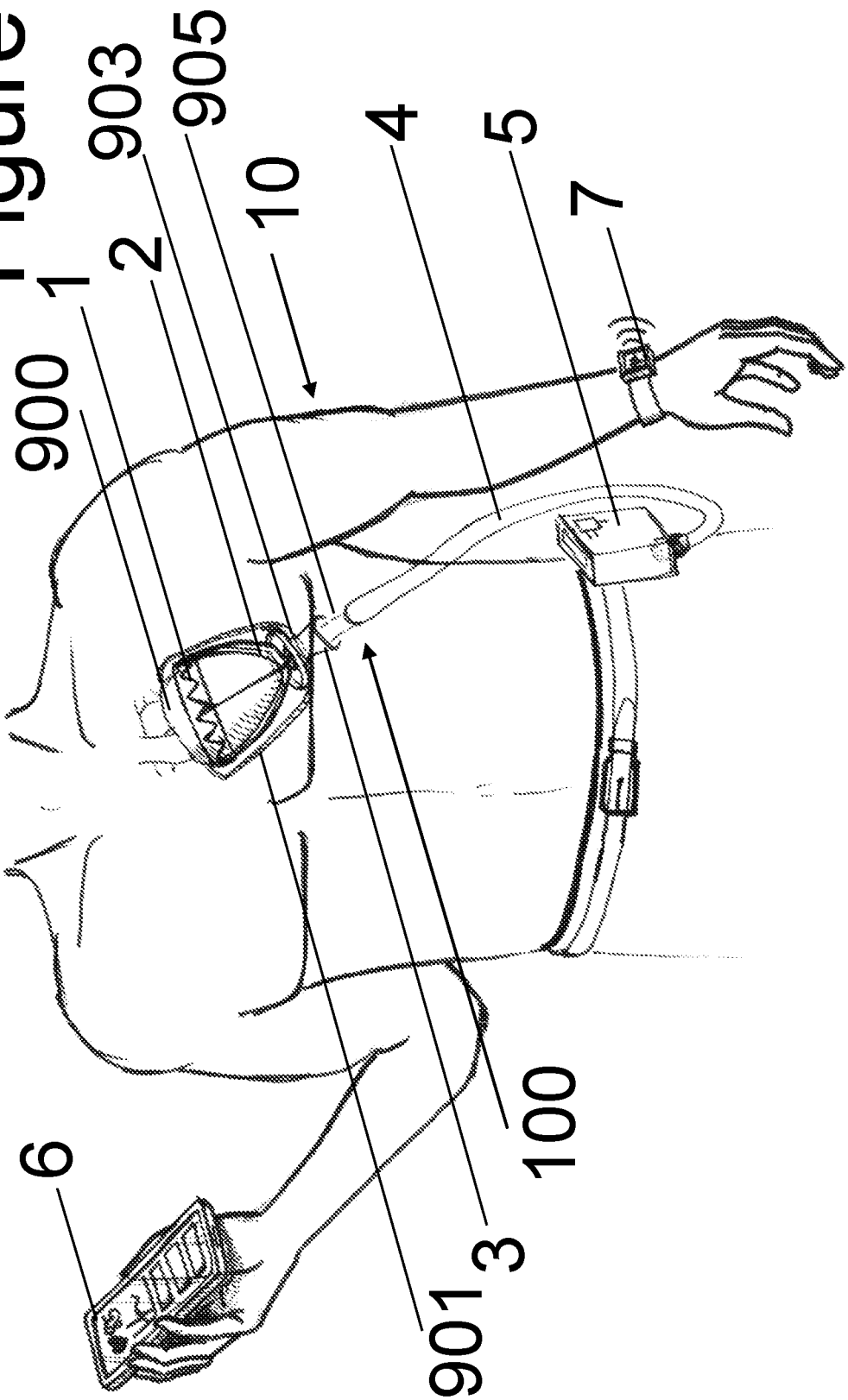
FIG. 1 shows a human torso with components of the implanted device having an extracorporeal supply unit.

FIG. 1 shows a human torso with an embodiment (1) of the device according to the invention in the implanted state. The implant (100) comprises a frame structure (1), a sleeve (2) inserted therein, at least one expandable unit (positioned on the sleeve (2) and/or the frame structure (1)) and at least one substance carrier, at least one sensor and at least one electrode. Also ascribed to the implant (100) are a pericardium sluice (3), the implanted part of a cable harness (4) and pneumatic/hydraulic substance lines and electric lines inside the body. The embodiment (1) of the device according to the invention also comprises a supply unit (5). A control unit (6) and a monitoring unit (7) are also depicted. Embodiments of the device according to the invention may be implanted at least partially in a human body. However, it may also be implanted in the body of an animal. Embodiments of the device according to the invention may be implanted in the body of a mammal, for example the body of a dog, cat, rodent, primate, artiodactyl, perissodactyl or marsupial. Depending on the species, special adjustments may have to be made to the shape and functioning of the implant (100), the cable harness (4) and the supply unit (5) in order to match the anatomy and/or physiology of the species concerned. The device comprises a frame structure (1) at least partially surrounding the heart (900). Also depicted is an encased cable harness (4) which exits from inside the body and is connected to a supply unit (5). Not depicted in FIG. 1 are, for example, a sleeve (2) that may be inserted into this frame structure (1) or further components that are mounted onto the surface of the sleeve (2) or are incorporated into it and may have a therapeutic effect. These are described elsewhere.

The frame structure (1) may be converted from a non-expanded state to an expanded state for the purposes of implantation, which may also be carried out minimally invasively. In the expanded state, the frame structure (1) may at least partially surround a heart (900). In the expanded state, the frame structure (1) may perform a shaping, positioning or stabilizing function or a combination thereof. In the non-expanded state, the frame structure (1) may be inserted into a delivery system. The frame structure (1) may be a single part or may alternatively consist of two, three, four, five, six or more parts. The frame structure (1), which consists of at least one wire or at least one strut, may be made at least partially out of a shape memory alloy. Materials for shape memory alloys are, for example, NiTi and NiTiFe (nickel-titanium and nickel-titanium-iron; nitinol), NiTiCu (nickel-titanium-copper), CuZn (copper-zinc), CuZnAl (copper-zinc-aluminium), CuAlNi (copper-aluminium-nickel), FeNiAl (iron-nickel-aluminium) and FeMnSi (iron-manganese-silicon). The frame structure (1) may also consist of titanium or titanium alloys, tantalum or tantalum alloys, stainless steel, polymer, polymer fibre material, carbon fibre material, aramide fibre material, glass fibre material or combinations thereof. The frame structure (1) at least partially surrounds the heart (900) in the implanted state and is located inside the pericardium. The frame structure (1) may also be mounted outside the pericardium. Such embodiments are not explained separately because the description applies to embodiments implanted both inside and outside the pericardium (apart from the pericardium sluice (3) which is omitted in the case of an embodiment located outside the pericardium). The frame structure (1) may have at least one radiopaque marking with the aid of which the positioning and orientation of the frame structure (1) in relation to a heart (900) may be checked during and after implantation. The make-up of the frame structure (1) is explained in more detail in one of the following sections.

At least one sleeve (2) may be inserted into the frame structure (1). The sleeve (2) may be held by the frame structure (1). The sleeve (2) may be coupled to the frame structure (1). Alternatively, a frame structure (1) may be incorporated into a sleeve (2). The sleeve (2), the structure thereof and the coupling between frame structure (1) and sleeve (2) are explained in more detail in one of the following sections. Components with which a therapeutic effect may be achieved may be inserted into the frame structure (1) or into the sleeve (2). For example, the therapeutic effect may be achieved by exerting mechanical forces or by delivering substances onto the epicardium (the surface of the heart (900)).

FIG. 1 also shows a supply unit (5) which may be carried outside the body. The supply unit (5) may also be partially or fully implanted in the body. If the supply unit (5) is carried outside the body, it may be affixed to a chest strap, to a hip belt or to an abdominal belt. Alternatively, it may be carried in a holster or on/in a rucksack. Other forms of fixing or carrying are also conceivable. FIG. 1 also shows a cable harness (4) which connects the supply unit (5) to the frame structure (1), to a sleeve (2) and/or to components inserted therein. The cable harness (4) is depicted encased in the present embodiment. A detailed description of the cable harness (4) is provided in a subsequent section. If the supply unit (5) is carried outside the body, the cable harness (4) may enter the body at a given place. If the device with a frame structure (1), a sleeve (2), at least one expandable unit and at least one component for achieving a therapeutic effect is located inside the pericardial cavity (902), the cable harness (4) or parts thereof may be fed into the pericardial cavity (902). The cable harness (4) may be delivered to the point of entry into the body (905) and/or to the point of entry (903) into the pericardial cavity (902) through a pericardium sluice (3), which is explained in more detail in a subsequent section of the description.

If the at least one component having a therapeutic effect that is inserted serves the at least locationally accurate delivery to and administration of substances onto the surface of the heart, at least one line may be located in the cable harness (4), said line allowing the subsequent delivery and/or discharge of a substance and/or a refilling of the substance in the inserted component.

If the at least one inserted component having a therapeutic effect is intended to exert a mechanical force on the surface of the heart, this requires the supply of energy from the supply unit (5). If the energy is supplied in the form of pneumatic or hydraulic energy, the cable harness (4) may contain at least one fluid line to transport pressurized fluid. If electrical energy has to be supplied, the cable harness (4) may contain at least one electrical conductor. If the supply unit (5) is carried outside the body, the electrical energy to be provided may alternatively also be conveyed to the device in the body wirelessly, for example using electromagnetic induction.

Alternatively, substances may also be administered and mechanical force may be exerted on the substance and/or the surface of the heart using the inserted component. In this case, at least one line may be provided for subsequently delivering and/or discharging a substance and/or refilling the substance and at the same time at least one fluid line or at least one electrical conductor may be provided.

If the device also contains at least one sensor, at least one electrode or at least one electrical load (for example a heating coil) in the frame structure (1), in the sleeve (2), in the at least one expandable unit or in the inserted component having a therapeutic effect, the at least one electrical line supplying the at least one sensor, electrode or load may likewise be located in the cable harness (4).

There may be mounted, at the end of the cable harness (4), a plug part which may be connected to the supply unit (5) via a couplable connection. Alternatively, a cable harness (4) with a plug part is provided only on the supply unit (5). In this case, the connection couplable thereto is located on the implanted device.

The cable harness (4) may be a single continuous cable harness (4) or a multi-part cable harness (4). In the case of a multi-part cable harness (4), at least one further couplable pair of plugs may be located at an appropriate place in the cable harness (4). In the case of a multi-part cable harness (4), at least one part of the cable harness (4) may be removed and at least one part of the cable harness (4) may remain on the implanted device or the supply unit (5). The removable part of the cable harness (4) may serve as an extension cable and may be used if required. The device may then also be used without the extension cable and the remaining plug parts may be coupled to one another so that the device may be operated. In the case of a multi-part cable harness (4), the individual cable harness pieces may be encoded, for example analogue-electronically, for example by means of a resistor, or digitally-electronically, for example using a ROM memory chip in the plug part. The supply unit (5) may read the encoding of the cable harness (4) and, if necessary, make adjustments in operation of the device. Such adjustments may, for example, be an increase in the supply of fluid required on account of the use of an extension cable.

Embodiments of the device according to the invention may also have separate cable harnesses (4) for the line for subsequently delivering and discharging substance, the fluid line or electrical line for supplying energy to the inserted component having a therapeutic effect and/or the electrical line to provide energy for the at least one sensor, the at least one electrode or the at least one electrical load. If the supply unit (5) is connected directly to the at least one inserted component having a therapeutic effect, the at least one sensor, the at least one electrode or the at least one electrical load, a cable harness (4) may alternatively be omitted.

One part of the continuous or multi-part cable harness (4), of the individual cable harness (4) or of the cable harness (4) divided into several cable harnesses (4) may run inside the body and another part may run outside the body. That part of the cable harness (4) that is inside the body may be between 0 cm and 70 cm in length, or between 30 cm and 60 cm in length. That part of the cable harness (4) that is outside the body may be between 0 cm and 90 cm in length, or between 50 cm and 80 cm in length. The diameter of the cable harness (4) may be between 4 mm and 25 mm, or between 6 mm and 12 mm. The multi-part cable harness (4) may be advantageous compared to the continuous cable harness (4) because it is modular and therefore, for example, may allow a variable, possibly greater freedom of movement of the patient.

The cable harness (4) may be surrounded by a fabric at least partially along its longitudinal axis and at least partially circumferentially. The fabric may be porous, fibrous or rough. It may improve the engraftment of the cable harness (4) into the surrounding conjunctive tissue and hence the mechanical anchoring of the implanted device according to the invention in the body. It may, for example, consist of felt, expanded PTFE, Dacron or another suitable biocompatible synthetic fabric. However, the material of the fabric may differ from this depending on the intended use. For example, an additional screening of the cable harness (4) from the environment may also be possible, for example in order to improve protection against irradiation and emissions.

FIG. 1 also shows an embodiment of a portable control unit (6) and a likewise portable monitoring unit (7). Embodiments of the device according to the invention may have a control unit (6) and a monitoring unit (7). It may also have just a control unit (6). It may also have just a monitoring unit (7). It may also have neither a control unit (6) nor a monitoring unit (7). The control unit (6) and/or the monitoring unit (7) may redundantly assume functions already assumed by the supply unit (5). They may alternatively also provide additional functions.

The control unit (6) may be designed as hardware with software played thereon. The hardware may provide here at least one communication interface, at least one display and/or also the ability to reproduce acoustic, visual or haptic signals. The software played on this hardware may assume control, monitoring and communication functions. However, the external control unit (6) may alternatively also use third-party supplier hardware and may merely be present in the form of a software package or an application ("app"). If the latter is the case, the communication interfaces provided by the third-party supplier hardware may be used in order to communicate with the information/control unit (6) or the supply unit (5). Communication may be carried out here via a wireless P2P connection, a Bluetooth connection, a WLAN connection or some other wireless form of data transmission. Alternatively, communication may also be carried out using wires. The control unit (6) may also assume an additional or exclusive monitoring function. For example, the data gathered by the at least one sensor of the implant (100) may be sent to the control unit (6) via the supply unit (5) (or directly to the control unit (6)), assessed and displayed for the user in a form legible to humans. The user may be the patient here, but may also be a treating doctor or a technician. The control unit (6) may be designed so that the function of the device is guaranteed even if the control unit (6) fails. The control unit (6) may also have purely informative functions.

The monitoring unit (7) may also be a control unit (6). However, it may also carry out exclusively monitoring functions. It may be connected to the control unit (6), but also to the supply unit (5) via one of the means of communication specified above. The monitoring unit (7) may be used in software form on hardware from third-party suppliers and then use the communication interfaces thereof. However, as with the control unit (6), the monitoring unit (7) may also be embodied as a separate piece of hardware with software played on it. The same functionalities may be carried out in respect of the software of the monitoring unit (7) as in the control unit (6). The monitoring unit (7) may, in particular, assume the function of quickly passing information on to the user. In the embodiment shown, the monitoring unit (7) is affixed to the wrist of the user and may therefore be viewed quickly. In the event of a technical or medical emergency, which may be recorded by the supply unit (5) or redundantly by the control unit (6) and/or the monitoring unit (7), this may be communicated to the environment (the user and their surroundings) via the monitoring unit (7) and/or the control unit (6). It is possible here to provide both local notifications (of a visual, acoustic or haptic nature) and notifications which may be sent directly to certain places, for example the emergency doctor or a different third place. This enables the response time to be reduced in the event of an emergency. It is also conceivable, if the control unit (6) is a mobile telephone, for the emergency doctor to communicate directly with the patient, a first aider or a doctor on site using this apparatus. The monitoring unit (7) may also measure at least one parameter of the body, for example the oxygenation of the blood or the person's pulse. The measurement of other parameters of the body is also conceivable.

The overall device, consisting of an implant (100) and a supply unit (5) connected thereto, may also be implanted entirely in the body. Energy may be supplied here through electromagnetic induction from outside the body and so recharge the at least one accumulator or the at least one battery. An advantage of this embodiment is that it avoids any artificial body opening (903) that is required to lead the cable harness (4) from the implant (100) to the supply unit (5). The supply unit (5) may be implanted above the liver and the diaphragm in the chest cavity or laterally to the right under the diaphragm in the abdominal cavity. Other implantation sites are also conceivable. If the supply unit (5) is implanted under the diaphragm, the cable harness (4) may pierce through the diaphragm in order to be fed to the pericardium (901).

Figure 2:
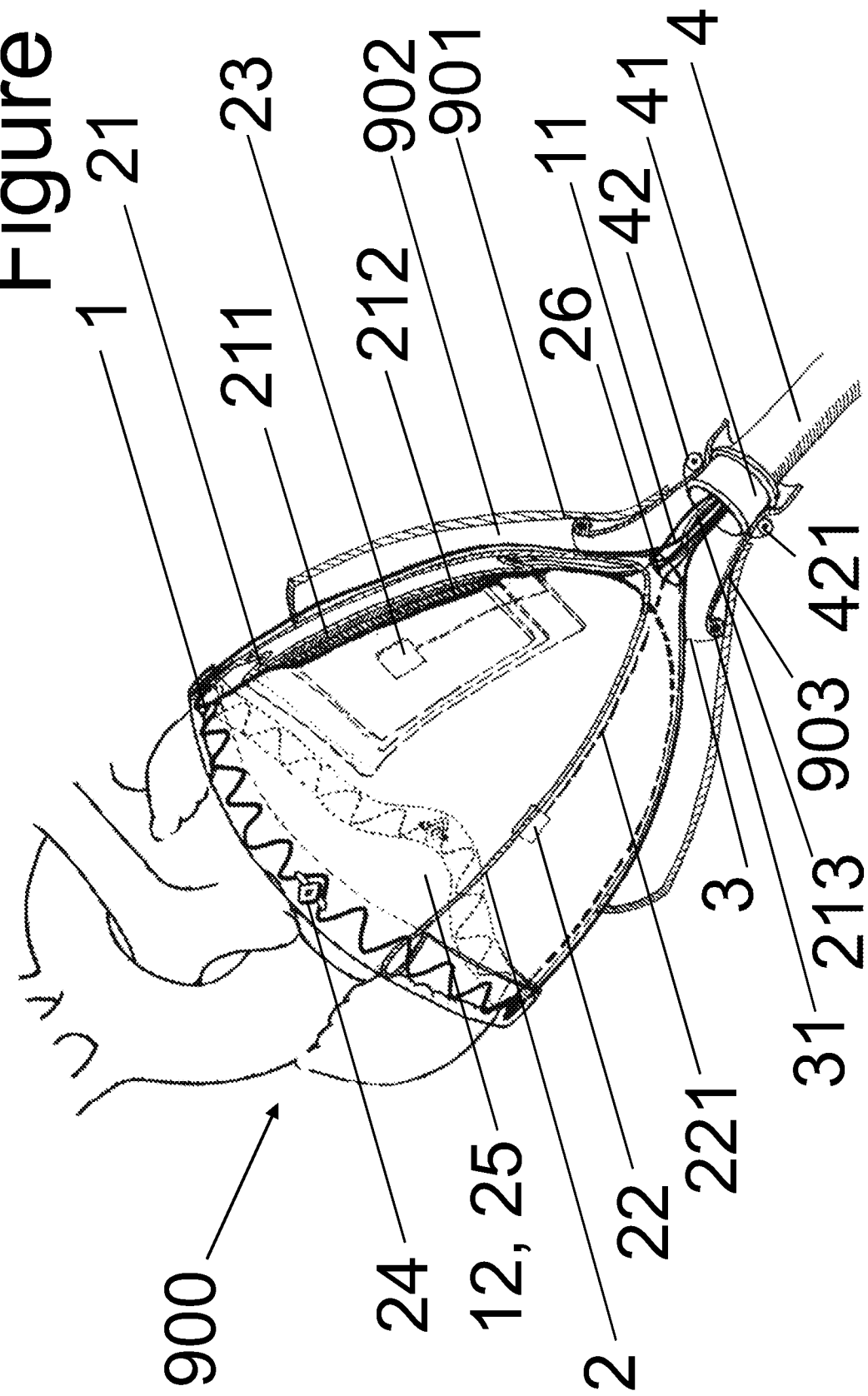
FIG. 2 shows an embodiment of the implant in the expanded and sealed state in which it partially surrounds a heart and lies inside the pericardium.

FIG. 2 shows an embodiment of the implant in the implanted state. Depicted by way of example are a human heart (900), a frame structure (1), a sleeve (2), an expandable unit (21) with the associated line (213), a substance carrier (211), the substance administered thereon (212), sensors and/or electrodes with the associated wires, a fixing sleeve (41), a part of a cable harness (4), a pericardium sluice (3) and a fixing ring (42) of the implant.

The frame structure (1) in this embodiment is depicted as a wire framework. The frame structure (1) may be formed out of at least one wire. The frame structure (1) may also be formed out of two, three, four, five, six or more wires. The frame structure (1) may also be a structure consisting of struts. In this case, the frame structure (1) consists of at least one strut. The frame structure (1) may also be formed out of two, three, four, five, six or more struts. One function of the frame structure (1) may be to guarantee mechanical stability in the expanded state. A further function of the frame structure (1) may be to allow expansion from the non-expanded state to an expanded state. A further function of the frame structure (1) may be to stretch a sleeve (2) which may be affixed in or on the frame structure (1) in order to form it into a specific shape. The spaces in the frame structure (1) which are defined by the at least one wire or the at least one strut may be openings in the frame structure (1). They may serve to increase flexibility, save weight or facilitate the exchanging of liquid from outside the frame structure (1) into its internal cavity and vice versa. More detailed explantations of the make-up and details relating to the functioning of the frame structure (1) are provided in one of the following sections.

A sleeve (2) may be inserted into the frame structure (1). The sleeve (2) may be affixed to the frame structure (1). The inside or the internal face is defined as the side or surface of the sleeve (2) facing the heart in the implanted state of the device. The outside/external face is the correspondingly opposite side/surface of the sleeve (2). The sleeve (2) may at least partially following the shape of the surface of a heart (900) or of a copy of a heart (900). The sleeve (2) may be designed to be patient-specific. In the implanted state, the sleeve (2) may at least partially surround part of a heart (900). The sleeve (2) may be affixed to the frame structure (1) such that the sleeve (2) is pulled over the edge of the frame structure (1) at the upper edge of the frame structure (1). In a further step, that part of the sleeve (2) that has been pulled over is connected to the part that has not been pulled over through openings present in the frame structure (1). The two parts may be welded, stitched or stuck together. Other methods of coupling, for example positive connections, are also conceivable. The sleeve (2) may also be affixed to the frame structure (1) through hanging from points provided for that purpose. At least one sensor and/or at least one electrode (23) may be mounted both on the inside of the sleeve (2) and on the outside of the sleeve (2). The sleeve (2) may consist of plastic, polymer, rubber, gum, latex, silicon or polyurethane. The sleeve (2) may have a thickness of 0.1 mm to 1 mm, preferably 0.2 mm to 0.5 mm.

The process for producing the sleeve (2) may be divided into a number of subsidiary steps. The starting point for a patient-specifically formed sleeve geometry may be a medical image data record. The patient-specific heart geometry may be extracted therefrom and transferred into a three-dimensional copy. This copy may form a model for the process of shaping the sleeve (2). In order to shape the sleeve (2), a moulding may be required which may be derived from the three-dimensional copy of the heart (900). The moulding may be milled from a single piece. Alternatively, it may also be produced using a 3D printing method from a three-dimensional computer model. Alternative manufacturing methods for producing the moulding, such as casting, are also conceivable. The sleeve (2) may surround a heart (900) and lie here at a specific distance from the surface of the heart. The distance may be between 0 mm and 3 mm, or between 0.4 mm and 2 mm. In order to create this spacing, the three-dimensional copy of the heart (900) may be scaled. The scale factor may be chosen here such that the distance between the surface of the heart and the sleeve (2) corresponds to the value range specified above. The moulding may consist of a metal. The moulding may also consist of a plastic. Metallic materials may be aluminium and aluminium alloys, steel and steel alloys or copper and copper alloys here. Other metals may also be possible. In the case of an embodiment of the moulding made out of plastic, for example, polyurethane (PU), polyamide (PA) or polyethylene (PE) may be possible. Other plastics having suitable mechanical properties may also be possible. The moulding may already have characterizations for the position of at least one expandable unit (21), which simplifies the subsequent process of mounting the at least one expandable unit, for example on manual production and mounting of the at least one expandable unit. It is also possible for places already to be provided on the moulding where delivery lines may start, for example for pneumatic actuation of the expandable units (21) or for delivery of the substance in the substance carriers (211) described in more detail in a subsequent section. The sleeve (2) may be stretched over the moulding and becomes plastically deformable when the temperature is increased. The sleeve (2) may cling to the moulding and take on the shape of the moulding after cooling. The instructions for the positioning of the expandable units (21) and the starting points of the delivery lines may also be imprinted on the sleeve (2) in this way. Finally, a protrusion of the material of the sleeve (2) over the actual geometry of the sleeve (2) may be used to couple the sleeve (2) to the frame structure (1), for example by turning it inside out, in a subsequent manufacturing step.

The sleeve (2) may be coupled to the frame structure (1). The coupling may be carried out at the upper edge of the frame structure (1) (where the previously described alternating wire or strut feed is provided), in particular by turning up the sleeve (2) and by coupling the sleeve (2) to itself through the openings in the frame structure (1). The sleeve (2) may be coupled to itself, for example, through adhesion, welding or stitching. Other methods of connection which achieve the same effect are also possible. For example, the sleeve (2) may be suspended from points provided on the frame structure (1) for that purpose (for example at the ends of the alternating wire feed). In such a case, the sleeve (2) may have at least one pocket which may be pulled over at least one loop or at least one stirrup.

The frame structure (1) may have an opening (26) at the lower end. Part of the sleeve (2) may penetrate through this opening (26), for example between 3 mm and 2 cm of the sleeve (2) may penetrate through. The sleeve (2) may also be open underneath, thereby improving the exchanging of liquid between the space inside the sleeve (2) and the space between frame structure (1) and pericardium (901) and vice versa. For example, pericardium liquid may flow in and out through the opening (26) in the sleeve (2). The upper edge of the frame structure (1) preferably runs parallel with the level of the heart valve and may have at least one area with at least one recess (12). The recess (12) in the frame structure (1) may be necessary owing to anatomical conditions, for example in order not to spatially impair the inferior vena cava which runs from the back towards the right atrium of the heart (900). Spatial impairment of the inferior vena cava would lead to inferior cava syndrome (obstruction of the filling of the right atrium). A recess (12) may also be necessary on account of other anatomical or cardial structures. If the frame structure (1) is designed as a lattice or wire mesh, the recess (12) may be made through subsequent detachment of struts or wires. Alternatively, a manufacturing method may also be chosen in which the recess (12) does not have to be produced afterwards. For example, in the case of frame structure (1) made out of a wire mesh, the wire winding may be adjusted so that the wires are chosen to be shorter at the site of the recess (12) and the crossing points move closer together. In the case of a frame structure (1) which consists of a lattice made out of a slotted tube, the recess (12) may be made through suitable cutting of the tube and correspondingly modified slotting. The slotting may be adjusted so that, despite the recess (12), the number of cells in the frame structure (1) remains the same. This may be necessary for stability reasons. If more flexibility in the frame structure (1) is desired, the slotting of the tube may be modified such that one, two or three rows of cells are omitted at the site of the recess (12). The sleeve (2) may be adapted to the recess (12) and may itself have a recess (25) which coincides as far as possible. Along the upper edge of the frame structure, the recess (12) may have a length of 2 cm, 3 cm, 4 cm, 5 cm, 6 cm, 7 cm or more. The depth of the recess (12), measured from the imaginary uninterrupted upper edge of the frame structure to the point of the recess (12) which lies closest to the apex of the heart, may be between 1 mm and 40 mm, in particular between 3 mm and 15 mm. In the circumferential direction, the recess (12) is positioned where the inferior vena cava opens into the right atrium. The recess (12) may be curved, semicircular, rectangular or polygonal. The recess (12) may be sufficiently long that it corresponds to the circumference of the upper edge of the frame structure (1). The recess (12) may then begin and end at the point of the upper edge of the frame structure (1) which lies opposite the cardial structure to be left free, for example the inferior vena cava. This may result in the recess (12) defining a level which is tipped over with respect to the level of the heart valve and which comes to rest at the site to be left free 1 mm to 40 mm, in particular 3 mm to 15 mm lower than if the upper edge of the frame structure (1) were to run parallel to the level of the heart valve. The sleeve (2) has a recess (25) which essentially corresponds to the recess (12) in the frame structure (1) in terms of its shape, position and dimensions and which leaves free the anatomical area around the inferior vena cava. Spatial impairment of the inferior vena cava through the sleeve (2) and the resultant obstruction of the filling of the right atrium is thereby prevented. The recesses (12, 25) in the sleeve (2) and frame structure (1) may be made to coincide with one another.

The frame structure (1) may have several markings. As already described, these markings may be in various forms or positions. In the present embodiment, the markings may be made on the upper edge and at the lower end in the direction of the apex of the frame structure (1).

At the lower end of the frame structure (1), one, two, three, four, five, six or more extension struts (11) may be mounted on the frame structure (1). The extension struts (11) represent an extension of the frame structure (1) in the direction of the longitudinal axis of the heart. The extension struts (11) may run in the direction of an imaginary apex of the heart, rest there or not rest and protrude from there away from the heart (900) in the direction of the longitudinal axis of the heart. The extension struts (11) may be gathered together in a joint fixing sleeve (41). The extension struts (11) and/or the fixing sleeve (41) may be connected to the cable harness (4) of the device, for example by gluing, welding or positive or non-positive anchoring. The extension struts (11) may serve to fix the frame structure (1) in the axial direction. The extension struts (11) only partially restrict the rotation of the frame structure (1) about the longitudinal axis of the heart. If the frame structure (1) is made out of a wire mesh, the extension struts (11) may represent the extended ends of wires. The extension struts (11) and the wire mesh may therefore be one part. If the frame structure (1) consists of a lattice that has been made out of a slotted tube, the lattice may be made using the extension struts (11) through suitable cutting out of just one tube. The lattice and the extension struts (11) may therefore be one part. The extension struts (11) and the frame structure (1) may also be multi-part, whereby the extension struts (11), after production of the frame structure (1), are affixed thereto, for example through a suspension mechanism or through material bonding (welding, gluing). Alternative methods of coupling having the same or similar effect are also conceivable. The length of the extension struts (11) may be between 1 cm and 10 cm, in particular between 4 cm and 7 cm.

The frame structure (1) may comprise only the recess (12) described above and no extension struts (11). Alternatively, the frame structure (1) may comprise both the recess (12) described above and the extension struts (11) described above. The frame structure (1) may also comprise only the extension struts (11) described above and no recess (12).

At the lower end of the frame structure (1) there may be at least one extension strut (11) which fixes the frame structure (1) to the cable harness (4) in the axial direction and stabilizes the device. The at least one extension strut (11) may be coupled to the cable harness (4) of the device. Possible methods of coupling are sticking, clamping, moulding, plug connection, suspension or welding. Alternative methods of coupling are also conceivable. Part of the at least one extension strut (11) may also remain in a fixing sleeve (41) after implantation.

The implant (100) may also comprise a fixing sleeve (41). The fixing sleeve (41) is represented in the present embodiment as a hollow cylinder through which pneumatic/hydraulic, electrical and substance lines may be fed from the distal end of the fixing sleeve (41) and bunched together in the cable harness (4) at the proximal end of the fixing sleeve (41). The cable harness (4) may be coupled to the fixing sleeve (41), for example by means of an adhesive connection (material bonding) or non-positive connection (for example by shrinking the cable harness sheath onto the fixing sleeve (41)). Other methods of coupling are also conceivable.

The fixing sleeve (41) and the cable harness (4) may alternatively also be coupled via an intermediate piece. This intermediate piece may, for example, consist of at least one segment which may allow an at least partially rotatory and/or at least partially translational relative movement between the cable harness (4) and the fixing sleeve (41). The advantage of such indirect coupling is the virtually independent settability of the orientation of the longitudinal axis of the frame structure (1) and of the fixing sleeve (41) and of the orientation of the cable harness (4). The intermediate piece may, for example, be designed as a ball joint. The intermediate piece may alternatively consist of a hose construction comprising at least one segment. As the material of the intermediate piece, polymers, plastics or metals and metal alloys may be used. Other materials which meet the mechanical requirements (in particular with regard to fatigue strength) may also be used.

A fixing ring (42) interacting with the fixing sleeve (41) may also be used to seal the pericardium (901). Together with the fixing sleeve (41), the sluice and a fixing ring (42), the at least one axial extension strut (11) may form the device for closing the pericardium (901). The fixing ring (42) may, for example for stiffening purposes, have a core (421) consisting of a stiffer material than the rest of the fixing ring (42). Possible materials may be steel, nitinol or a stiff polymer. Other materials are also conceivable. If alternative devices are used to seal the pericardium (901), for example through use of a multi-part pericardium sluice (3), at least part of the at least one extension strut (11) may also lie outside the pericardium (901) and at least part of the at least one extension strut may lie inside the pericardial cavity (902). If the device should have a force exerted on it away from the heart (900) in the direction of the longitudinal axis of the heart as a result of the expansion of the at least one expandable unit (21), some of this force may be dissipated via the frame structure (1), the extension struts and the cable harness (4) without any resultant dislocation of the device. The extension struts (11) may have, at their ends, holes, stirrups, loops or angled ends which facilitate the minimally invasive explantation of the frame structure (1) and the sleeve (2). The angled ends, holes, stirrups or loops do not impede the fixing of the extension struts (11) in the fixing sleeve (41). They may be used for fixing or centring the extension struts (11) in the fixing sleeve (41). Upon implantation or during operation of the device, ends of the extension struts (11) may be located inside the cable harness (4) or inside the fixing sleeve (41). Implantation and explantation of the implant are described in more detail in following sections.

At least one expandable unit (21), for example in the form of a bellows-like chamber, may be mounted on the sleeve (2). The expandable unit (21) may be an actively expandable unit (21) or a passively expandable unit (21). A sensor and/or an electrode (23) may also be mounted on the sleeve (2). The sleeve (2) may be the underside of the expandable units (21). The expandable units (21) may be adjusted to the shape of the heart (900), the frame structure (1) and/or the sleeve (2). One, two, three, four, five, six, seven or more expandable units (21) may be mounted on the sleeve (2). When expanding, the expandable units (21) may exert a pressure on the heart muscle. This pressure is preferably exerted in areas of the heart muscle under which a heart chamber is located, preferably below the level of the heart valve. In another embodiment, the pressure may also be exerted above the level of the heart valve in the case of certain therapeutic uses. If the expandable units (21) are positioned in the lower area of the sleeve (2) and/or frame structure (1) near the apex of the heart, on expansion of the expandable units (21), the heart muscle is pressed in the direction of the longitudinal axis of the heart upwards to the level of the heart valve. If the expandable units (21) are arranged in the upper area of the sleeve (2) and the frame structure (1), on expansion of the expandable units (21), the heart muscle is pressed perpendicularly to the longitudinal axis of the heart. Pressure is then exerted on the heart muscle parallel to the level of the heart valve (laterally onto the ventricle). The expandable units (21) may also be positioned in any position between the lower edge and the upper edge of the sleeve (2) and frame structure (1), whereby the pressure of the expandable units (21) when they expand acts partly in the direction of the longitudinal axis of the heart and partly parallel to the level of the heart valve. On expansion of the expandable units (21), the pressure therefore acts as far as possible parallel to the level of the heart valve. The counterforce on the device in the direction of the longitudinal axis of the heart is therefore kept at a low level. Displacement of the device away from the heart in the direction of the longitudinal axis of the heart (dislocation) caused by expansion of the expandable units (21) is therefore minimized. The self-expanding frame structure (1) and the sleeve (2) have recesses (12, 25) in this depiction in order not to spatially impair the inferior vena cava in the implanted state of the device. The expandable units (21) may be adjusted in terms of their size, shape and position to the recesses (12, 25) in the frame structure (1) and the sleeve (2) so that they do not cover the recesses (12, 25) either in the expanded or in the non-expanded state.

The at least one expandable unit (21) may carry out various tasks. It may exert a temporally adjustable pressure on the surface of the heart which is preferably periodic or dependent on the current phase of the heart cycle. If the aim of exerting pressure is to increase the emission of blood, the expandable unit (21) may be an augmentation unit. The concept of augmentation may therefore be understood to refer to the supportive increase or at least the changing of a heart parameter such as the emission quantity. Alternatively, the at least one expandable unit (21) may also exert temporally variable pressure on the surface of the heart without the primary aim thereof being to increase the quantity of blood emitted. Instead, this kind may relate to an expandable unit (21) serving to position or stabilize the implant with respect to the heart (900). In both said cases, energy needs to be supplied in order to be able to set the degree of expansion of the at least one expandable unit (21). These may be active expandable units (21). Alternatively, the at least one expandable unit (21) may also manage without a supply of energy. In this case, the at least one expandable unit (21) may have a previously settable degree of expansion and keep this irrespective of time. Such an expandable unit (21) may be regarded as a passive expandable unit (21). This kind of expandable unit (21) is described in more detail in a subsequent section.

The expandable unit (21) may be a mechanical unit which may have an expanded and a non-expanded configuration. The at least one expandable unit (21) may also have configurations between the expanded and the non-expanded configuration. The at least one expandable unit (21) may serve to exert pressure on the surface of the heart. The at least one expandable unit (21) may serve to position a substance (212) or a substance carrier (211). The at least one expandable unit (21) may also serve to ensure contact between the surface of the heart and a substance carrier (211) or a substance (212) which is located on the surface of the expandable unit (21). The expandable unit (21) may also serve to produce a defined state of mechanical load in the substance (212) and/or in the substance carrier (211).

The at least one expandable unit (21) may consist of the same material as the sleeve (2). The material of the at least one expandable unit (21) may also differ from the material of the sleeve (2). The material of the at least one expandable unit (21) may be a polymer. The material of the at least one expandable unit (21) may be polyurethane, silicone or polytetrafluoroethylene (PTFE). Other materials which are in principle able to meet the requirements of an expandable unit (21) are also conceivable. The at least one expandable unit (21) may be designed as an inflatable, bellows-like chamber. The chamber provided in the depicted embodiment is in the form of a set of bellows. A bellows-like chamber has at least one section in the form of a set of bellows. The expandable unit (21) may be a set of bellows that consists of one, two, three, four, five, six, seven or more pleats. The at least one expandable unit (21) may also differ from the form of a set of bellows.

Such an expandable unit (21) may be operated through tensionable and releasable spring elements, foldable and unfoldable lever elements and/or an elastic, sponge-like or foam-like internal structure. The expandable unit (21) may also be actuated electrically, for example through at least one electromagnet. The at least one electromagnet may be affixed to one side of the expandable unit (21) or incorporated into a wall of the expandable unit (21). A ferromagnetic, paramagnetic material, for example in the form of wires, a thin plate or foil, or a further electromagnet may be placed on the surface of an expandable unit (21) positioned opposite so that energization of the at least one electromagnet causes a change in the state of expansion of the expandable unit (21). Alternatively, spring elements, lever elements, electromagnets and/or ferromagnetic materials may be combined with one another in an expandable unit (21). For example, the expandable unit (21) may be expanded through one or more spring elements and energization of the at least one electromagnet may lead to the mutual attraction of the sides lying opposite one another and hence to the return to a non-expanded state. The at least one expandable unit (21) may have a delivery line for supplying energy which is required to change the expansion state. If the expandable unit (21) is operated electrically, for example electromagnetically, the line (213) for supplying energy may be an electric cable.

Alternatively, the at least one expandable unit (21) is a chamber which may be filled with a fluid. As fluids which are suitable for filling the chamber, liquids, gases, solids (for example nanoparticle mixtures) or mixtures of liquids and/or gases and/or solids are possible. In this case, the expandable unit (21) has a delivery line through which the medium used to expand the at least one expandable unit (21) may be fed. The at least one expandable unit (21) may have a discharge line through which the medium used to expand the at least one expandable unit (21) may be discharged. A line (213) may also be provided for delivering and discharging the medium used for expanding the at least one expandable unit (21).

The at least one expandable unit (21) may be affixed to the inside of the sleeve (2). The expandable unit (21) may also be affixed to the outside sleeve (2). The at least one expandable unit (21) may be mounted in any desired area of the outside or inside of the sleeve (2).

The area of the surface of the heart which may require the use of the at least one expandable unit (21) may be in a different place depending on the individual patient concerned. The free positionability of the at least one expandable unit (21) serves to adapt the implant to the individual geometry of the heart to be treated.

The at least one expandable unit (21) may be in the form of a chamber. The chamber may be bellows-like. A bellows-like chamber has at least one section in the form of a set of bellows. A pleat may be defined as an outwardly directed fold line. A pleat may be defined as an inwardly directed fold line. One, a number or all of the fold lines may be strengthened. Strengthening of a fold line is advantageous because the fold line may be exposed to increased loads as a result of the expanding and contracting of the chamber. Strengthening one or more fold lines may reduce or prevent material fatigue along the at least one fold line. Strengthening of a fold line may be achieved through a greater wall thickness of the material at the fold line. A fold line may also be strengthened by applying additional material, wherein the applied material may be the same material as the material underneath or wherein the applied material may be a different material from the material underneath. A chamber may have a top, an underside and a side surface, wherein the side surface is preferably designed in the form of a set of bellows. The top and/or underside may be oval, circular, elliptical or polygonal. The top may be a different shape than the underside.

A bellows-like chamber may be provided in a frame structure (1) as described above. The chamber may be affixed or attached directly in the frame structure (1). The chamber may be affixed to structural elements of the frame structure (1), such as a wire of a wire mesh, a strut of a lattice or a structure on a frame structure sheath. The chamber may be affixed to crossing points of a mesh or lattice.

The bellows-like chamber may also be affixed to the sleeve (2). A plurality of bellows-like chambers may be affixed to the sleeve (2). The sleeve (2) may be at least partly in the shape of a heart (900). The sleeve (2) may have a shape similar to the frame structure (1). The sleeve (2) may, in addition to one or more augmentation units, such as one or more bellows-like chambers, also have one or more positioning units. The underside of the chamber may be made out of the same material as the sleeve (2). The sleeve (2) may be part of the chamber. The sleeve (2) may form the underside of the chamber. In such cases, only the side surfaces which may be bellows-like are mounted on the sleeve (2). A top may also be provided. The top may also be a sleeve (2), but may also be a top embodied as a separate component. The at least one line (213) which supplies the at least one expandable unit (21) may be defined, like the chamber, at least partly also using the sleeve (2) as the back and a front provided, for example, through adhesive or welded connection. The at least one line (213) may alternatively also be a completely separate, hose-like component.

The at least one expandable unit (21) may have at least one sensor and/or at least one electrode (23). This sensor may preferably be mounted on a surface of the at least one expandable unit (21) facing the heart (900). However, the sensor may also be mounted somewhere else on the at least one expandable unit (21). The sensor may be a temperature sensor, a pressure sensor, a pH sensor, an oxygen sensor, a $CO_2$ sensor, an optical sensor or a conductivity sensor. Alternatively, the at least one sensor may also serve as an impedance sensor for monitoring the adhesion of cells or cell cultures applied to the at least one expandable unit (21) or for monitoring contact with the epicardium. The electrode (23) may also be a sensor. The advantage of providing the at least one sensor and/or the at least one electrode (23) is that, with the aid of the at least one expandable unit (21), constant contact of the at least one sensor and/or the at least one electrode (23) with the surface of the heart may be guaranteed.

The position and/or shape of the at least one expandable unit (21) may be described in the form of coordinates in three-dimensional, Euclidean space so that these coordinates correspond to points on the surface of the sleeve (2) and may therefore be interpreted and used, for example, by machine tools such as milling machines, 3D printers, industrial adhesion robots or laser cutting machines. These coordinates may be determined using the three-dimensional image data of the heart (900), for example from a CT data set. For example, the position and/or shape of the at least one expandable unit (21) may therefore be adjusted to the position and/or shape of an anatomical structure or the position and/or shape of a pathological change in the heart (900), for example caused by a myocardial infarction. The at least one expandable unit (21) may at least partially cover the site of a myocardial infarction or may be positioned in the immediate spatial vicinity of the site of the infarction (the "border zone").

The sleeve (2) may comprise at least one sensor and/or at least one electrode (23) for measuring a parameter of the heart (900) or for stimulating the heart (900). A more detailed explantation is provided in a subsequent section. The at least one electrode (23) may be made out of nitinol which increases its deformability and may therefore be advantageous for the minimally invasive insertion of the implant in the non-expanded configuration. Other common electrode materials are also conceivable. For example, the electrode (23) may also have a coating to improve its electrical properties which may be advantageous, in particular, when measuring at least one parameter of the heart (900).

At least one substance carrier (211) may be inserted into the sleeve (2). The at least one substance carrier (211) serves to store at least one substance (212) which may have at least one therapeutic effect. The substance (212) may be provided as a liquid, gel, in paste form, as a solid or in a combination thereof, for example as an emulsion or suspension. The substance (212) may partly consist of a liquid and/or a solid and/or animal or human cells and/or proteins and/or a gas. The at least one therapeutic effect of the substance (212) may be antithrombotic, antiproliferative, anti-inflammatory, antineoplastic, antimitotic, antimicrobial, anticoagulant, cholesterol-lowering or a combination thereof. The substance (212) may contain a biofilm synthesis inhibitor, an antibiotic, an antibody, a beta blocker or combinations thereof. The substance (212) may contain living biological cells. The substance (212) may contain proteins and/or active agents which enable living biological cells to survive and/or may influence cell activity and hence therapeutic efficiency. The proteins and/or chemicals may be encapsulated in micro- and/or nanoparticles which allow the encapsulated proteins and/or chemicals with defined release kinetics for targeted release of proteins and/or chemicals. The at least one substance carrier (211) may be positioned and affixed on an expandable unit (21). The at least one substance carrier (211) may also be positioned and affixed directly on the sleeve (2). The area of positioning of the at least one substance carrier (211) either on the at least one expandable unit (21) or the surface of the sleeve (2) is entirely optional. The free choice of location in which to position the at least one substance carrier (211) enables the patient-specific adjustment of the implant. The position and shape of the substance carrier (211) may be based, for example, on the site of any heart disease, for example a myocardial infarction. The substance carrier (211) may at least partially cover the site of a myocardial infarction or may be positioned in the immediate spatial vicinity of the site of the infarction (the "border zone"). The advantage of positioning the at least one substance carrier (211) in the border zone may be that this region has living tissue. In the case of a substance (212) which adheres well to the sleeve (2) or the expandable units (21), direct application in the form of a spread or a coating may also be considered, rendering the substance carrier (211) unnecessary in this embodiment. The border zone may, for example, be pre-marked or outlined on the sleeve (2) (if applicable with a certain tolerance) so that the substance (212) may be applied in a targeted manner in this location. This may prevent administration in the wrong place. The substance carrier (211) in the present embodiment is represented as a foil-like component affixed to the at least one expandable unit (21). The substance carrier (211) may be flat in shape. The substance carrier (211) may have a thickness of between 0.01 mm and 5 mm, between 0.05 mm and 2 mm, and preferably between 0.2 mm and 1.5 mm. That surface of the substance carrier (211) facing the heart (900)—the end face of the substance carrier (211)—may be at least partially circular, elliptical, rectangular or polygonal. The at least one substance carrier (211) may be patient-specific (with respect to geometry and therapeutic effect, for example in the dosage of the at least one active agent) and may be adjusted, for example, in terms of its size, taking account of anatomical features or the size and structure of a pathological change in the heart tissue or the shape of the at least one expandable unit to which the substance carrier (211) may be affixed. The fixing of the at least one substance carrier (211) to the at least one expandable unit (21) or the sleeve (2) is carried out through positive coupling, non-positive coupling and/or material bonding. In the case of positive connection, the coupling may be carried out through hooks, eyelets, buttons, loops or at least one Velcro fastening and/or zip. At least one hook and at least one eyelet, at least one hook and at least one loop, at least one button and at least one complementary positive locking element or at least one hook and at least one further hook may be the connection partners here. In the case of a non-positive connection, the at least one substance carrier (211) may be connected in a frictionally engaged manner by means of filamentary or lamellar extensions to likewise filamentary or lamellar extensions on the at least one expandable unit (21) or the sleeve (2). In the case of a materially bonded connection, the connection between the at least one substance carrier (211) and the at least one expandable element or the sleeve (2) may be carried out by gluing, vulcanization or welding. In the present embodiment, the substance (212) may be a gel or a paste and may be applied to the end face of the substance carrier (211). The substance (212) may be applied to the end face of the substance carrier (211) by gluing, spreading, brushing or spraying. Other methods of application are also conceivable.

The substance carrier (211) may also differ from the flat shape. The substance carrier (211) may be designed as a container, or else as a pouch or pocket. The substance carrier (211), in its embodiment as a pouch or pocket, may receive, hold and release the substance (212) to be administered. The substance (212) may be inserted into the substance carrier (211) and removed again in the implanted state. It may also be inserted into the substance carrier (211) in the non-implanted state and may remain in the substance carrier (211) or be removed again any time up until explantation of the implant. A more detailed description is provided in a subsequent section.

The sleeve (2) may also comprise at least one sensor and/or at least one electrode (23) with the aid of which at least one parameter of the heart (900) may be detected, for example the heart rate, the ventricular pressure, the contact force between the wall of the heart and an expandable unit, the systolic blood pressure or the diastolic blood pressure. The at least one sensor may also serve to determine various parameters in the substance carrier (211) and/or the surroundings of the substance carrier (211). The at least one sensor may be a temperature sensor, a sensor for detecting mechanical forces acting on the substance carrier (211) or a sensor for determining the concentration of substances influencing the conductivity, substances influencing the pH value, and substances influencing the oxygen and $CO_2$ content in the substance carrier (211) and/or the surroundings of the substance carrier (211). The at least one sensor may also be able to measure the pressure exerted by an expandable unit (21) on a surface, the pH value, the oxygenation, the electrical resistance, the osmolarity of a solution or the flow rate through a vessel. The at least one sensor may be mounted in, at or on the frame structure (1). The at least one sensor is preferably affixed to the sleeve (2) which may be inserted into the frame structure (1). The at least one sensor may also be an electrode (23).

The cables (221) may be designed as conducting paths. The conducting paths of the at least one sensor and/or of the at least one electrode (23) may be mounted at least partially on the sleeve (2). For example, the conducting paths may be mounted on foils of polyimide (PI), for example through vapour deposition or sputtering. Other methods of mounting or removal which allow conducting paths to be formed are also conceivable. Alternatively, conductive sensor cables and/or electrode cables or sensor conducting paths and/or electrode conducting paths may be glued onto the sleeve (2) or welded in it. The conducting paths may consist at least partially of nitinol here. The at least one electrode (23) may consist of the same material as the conducting paths. As another alternative, the conducting paths and/or the at least one electrode (23) may also consist of conductive electrographic ink and be printed onto the sleeve (2). Alternatively, the conducting paths of the at least one sensor and/or the at least one electrode (23) may also be fed without coupling to the sleeve (2) inside or outside the sleeve (2) in the direction of the fixing sleeve (41) and cable harness (4).

The at least one electrode (23) may be able to stimulate areas of the heart (900) and/or measure the potential for action in the heart muscle during the stimulation process. In particular, the at least one electrode (23) may be able to stimulate the heart muscle with the aid of electrical impulses. Electrical stimulation may incite a heart muscle to contract. The at least one electrode (23) may be a pacemaker electrode. The electrode (23) may be an extracardial stimulation electrode. The heart muscle may be stimulated with an electrode (23) before, during or after any support of the pumping function of the heart (900) by a frame structure (1) with at least one expandable unit (21). The at least one electrode (23) may also carry out a defibrillation function. The at least one electrode (23) may be in the form here of a flat, conductive patch which may be located at points on the surface of the heart which are suitable for defibrillation. An advantage of a patch may be the flat structure of an electrical field, the field lines of which are designed to be straighter than in rod-like or punctiform electrode geometries. Alternatively, the frame structure (1) may also function as an electrode (23). In this case, at least one further electrode (23) must be provided. The expansion of an expandable unit (21) may take place before, during or after any stimulation with an electrode (23). The device for supporting the functioning of a heart (900) may only be operated with at least one expandable unit (21) or only through stimulation with at least one electrode (23). Simultaneous operation of the at least one expandable unit (21) and the at least one electrode (23) may be synchronous or asynchronous. The at least one electrode (23) may also be used as a sensor. The at least one sensor and/or the at least one electrode (23) may comprise at least one electric cable (221). The at least one cable (221) may be incorporated into the sleeve (2). The at least one cable (221) may also be a conducting path insulated from the surroundings. The electrically conductive material may be mounted on the sleeve (2) and also insulated. The at least one cable (221) may be coupled to the sleeve (2), welded into the sleeve (2) or stuck to the sleeve (2). Depending on the position of the at least one sensor and/or the at least one electrode (23), the at least one cable (221) may run on the outside or the inside of the sleeve (2). The at least one cable (221) may also be fed through an opening (26) provided in the sleeve (2) for that purpose and fed along on the outside in the case of at least one sensor and/or at least one electrode (23) lying on the inside of the sleeve (2). The at least one cable may also be fed through an opening (26) provided in the sleeve (2) for that purpose and fed along on the inside in the case of at least one sensor and/or at least one electrode (23) lying on the outside of the sleeve (2).

The sleeve (2) may have an opening (26) at the lower end. This opening (26) may serve to feed out from inside the sleeve (2) the extended ends of the at least one wire or of the at least one strut in the case of an embodiment in which the frame structure (1) lies inside the sleeve (2). This opening (26) may serve to feed the at least one line (213) of the at least one expandable unit (21), in the case of an embodiment in which the at least one expandable unit (21) is affixed on the inside of the sleeve (2), outwards from inside the sleeve (2). This opening (26) may serve to feed the at least one cable (221) of the at least one sensor and/or of the at least one electrode (23) from inside the sleeve (2) in the direction of the fixing sleeve (41) onto the outside of the sleeve (2). This opening (26) may serve to facilitate the exchanging of substances (212) between the outside and the inside of the sleeve (2).

The frame structure (1) may have at least one radiopaque marking (24) with the aid of which the positioning and orientation of the frame structure (1) in relation to a heart (900) may be checked during and after implantation. Alternatively, the at least one radiopaque marking (24) may serve to set and monitor the desired position of the frame structure (1) which is favourable for implantation in the state inserted into a delivery system. Detailed explantations regarding the delivery system are provided in another section.

FIG. 2 also shows a pericardium sluice (3) which allows the implant to be inserted into the pericardium (901). The pericardium sluice (3) produces a feed channel for the implant (100) by delimiting a lumen from the surrounding tissue. The pericardium (901) is a sac made out of conjunctive tissue which surrounds the heart (900) and allows the heart (900) free movement through a narrow sliding layer. In the pericardial cavity (902) there is serous fluid, which is also referred to as liquor pericardii. In order that this liquor pericardii cannot flow out through a surgical opening (903) in the pericardium (901) made during implantation of the implant and so that no other liquids or solids (such as cells, proteins, foreign bodies, etc.) can gain access to the pericardial cavity (902), a pericardium sluice (3) may be inserted at least partially through the surgically made opening (903) in the pericardium (901). The pericardium sluice (3) may close and seal the surgical opening (903) made in the pericardium (901) for insertion of the implant into the pericardial cavity (902). The pericardium sluice (3) may have an internal lumen through which parts of the device according to the invention may protrude. After the device has been implanted, for example, a fixing sleeve (41) or part of the cable harness (4) may be located in the pericardium sluice (3) and remain there for the duration of the implantation. The pericardium sluice (3) seals the surgical opening (903) made in the pericardium (901) for the cable harness (4). The pericardium sluice (3) may be designed as a single part. The pericardium sluice (3) may also be designed as two parts or as multi-part. The pericardium sluice (3) may be rotationally symmetrical in shape. The pericardium sluice (3) may also be of asymmetrical shape. The pericardium sluice (3) may be located at least partially inside the pericardial cavity (902). The pericardium sluice (3) may be located at least partially outside the pericardium (901).

The pericardium sluice (3) may consist of a single material. The pericardium sluice (3) may also consist of at least two materials. The material of the pericardium sluice (3) may be at least one polymer. The pericardium sluice (3) may consist of plastic, polymer, rubber, gum, latex, silicone, polyurethane (PU) or polytetrafluoroethylene (PTFE). The pericardium sluice (3) may consist at least partially of a metal or a metal alloy. The pericardium sluice (3) may consist at least partially of a shape memory alloy. The pericardium sluice (3) may consist at least partially of nitinol. The pericardium sluice (3) may consist of a combination of at least two of said materials.

An embodiment of the pericardium sluice (3) is shown in cross section in FIG. 2. The embodiment is in two parts. It comprises the device for producing the lumen and a sealing ring outside the pericardium (901). The pericardium sluice (3) may comprise at least two components, but may also consist solely of the device for producing the lumen. The pericardium sluice (3) in this embodiment has two different ends. One end of the pericardium sluice (3) has a sealing lip (31) which may be annular. The other end of the pericardium sluice (3) has no sealing lip (31) in this embodiment. Alternatively, the pericardium sluice (3) may also have a sealing lip (31) at both ends. The material of the sealing lip (31) may be the same as the material of the rest of the pericardium sluice (3). The material of the sealing lip (31) may be different from the material of the rest of the pericardium sluice (3). The material of the sealing lip (31) may be plastic, polymer, rubber, gum, latex, silicone, polyurethane (PU) or polytetrafluoroethylene (PTFE). The sealing lip (31) of the pericardium sluice (3) may consist at least partially of a metal or a metal alloy. The sealing lip (31) of the pericardium sluice (3) may consist at least partially of a shape memory alloy. In addition to the sealing effect, the sealing lip (31) may also have a mechanically stabilizing effect in the radial and circumferential directions. Stiffness in the radial and circumferential directions may be set through the thickness of the sealing lip (31). The thickness of the sealing lip (31) may be between 1 mm and 10 mm. The thickness of the sealing lip (31) may be between 3 mm and 6 mm. The sealing lip (31) may have a self-retaining effect. In its implanted form, the upper end of the pericardium sluice (3) may be supported with the sealing lip (31) against the inside wall of the pericardium (901). Through the tapering of the pericardium (901) towards the apex of the heart, a mechanical self-retention may occur between the pericardium sluice (3) and the pericardium (901) and increase the sealing effect and the mechanical stability and positional accuracy of the pericardium sluice (3).

The core of the sealing lip (31) may be made out of a different material to the sheathing placed around the core of the sealing lip (31). At least one part of the core of the sealing lip (31) may be formed out of spring steel or a shape memory alloy and the sheathing of the core may be made out of a polymer. In the case of an embodiment of a pericardium sluice (3) having a core of the sealing lip (31) made out of metal or a metal alloy, the material of the sheathing of the core of the sealing lip (31) may differ from the material of the core of the sealing lip (31). In the present embodiment of the implant, the device for producing the lumen consists of one material, preferably of a polymer. The end with the sealing lip (31) is located inside the pericardial cavity (902) in this embodiment. It is in contact with the inside wall of the pericardium (901) there. The sealing lip (31) guarantees the sealing effect and stops liquid getting out of the pericardium (901) or substances entering the pericardial cavity (902). The self-expanding implant (100) may be inserted into the pericardial cavity (902) through the pericardium sluice (3). As a result, that end of the cable harness (4) with the fixing sleeve (41) which is near the frame structure (1) is located in the pericardium sluice (3). A sealing connection may be made between the fixing sleeve (41) and the pericardium sluice (3). In the present embodiment, the sealing effect is produced through a sealing ring pulled over the pericardium sluice (3). The seal between the pericardium sluice (3) and the fixing sleeve (41) may also be made possible by other means. The sealing effect may alternatively be produced by stitching the pericardium sluice (3) to the fixing sleeve (41), clamping the pericardium sluice (3) by means of a clamp, a clip or by means of at least one cable tie, which may be positioned around the fixing sleeve (41) and the pericardium sluice (3) lying opposite. The sealing effect may also be produced through the pericardium sluice (3) alone or through part of an embodiment of the pericardium sluice (3). The sealing effect may in this case be produced by suturing, knotting together or welding the lower end of the pericardium sluice (3). The full sealing of the surgical opening (903) made in the pericardium (901) may be provided at at least two interfaces: between pericardium (901) and pericardium sluice (3) and between pericardium sluice (3) and surroundings or pericardium sluice (3) and fixing sleeve (41). Additionally, the pericardium sluice (3) can also facilitate explantation because it effectively reduces the surface area between the implant and the pericardium (901), thus reducing adhesions between them.

FIG. 2 shows the pericardium sluice (3) in its configuration after insertion of the implant into the pericardial cavity (902). The process of inserting the pericardium sluice (3) is explained in more detail in a subsequent section.

An alternative embodiment of the implant may also be designed without the frame structure (1). This may be the case if no mechanical augmentation of the myocardium is required. Alternatively, the implant (100) may be designed without the sleeve (2) but with a frame structure (1). This may be advantageous if the mechanical supporting effect of the frame structure (1) is primarily intended to be used.

Other alternative embodiments may consist exclusively of the frame structure (1) and/or the sleeve (2) and at least one expandable unit (21). Such embodiments may therefore be implantable in their entirety. This has the advantage that the risk of inflammation is reduced because no cable harness (4) exits from inside the body. The at least one expandable unit (21) may, for example with the aid of at least one spring element, set or maintain a certain degree of expansion, whereby, for example, permanent contact of a substance carrier (211) mounted on the at least one expandable unit (21) with the surface of the heart may be guaranteed. The spring element may consist of polymer or plastic, metal or metal alloys or a shape memory material. In the case of embodiments which have no spring element, the expandable unit (21) may also be operated pneumatically/hydraulically. For example, a constant or a temporally variable degree of expansion may be set. Instead of at least one expandable unit (21), a passive silicone patch may also be used. The implant (100) may be designed to be self-sufficient and without any energy supply from outside the body. Alternatively, the implant (100) may also be connectionless, for example supplied with energy through induction.

A further embodiment may consist solely of at least one sleeve (2), which may be provided with a therapeutic substance (212). Such an embodiment may be implanted in a very space-saving manner. An advantage of such an embodiment may be that it manages without a cable harness (4) or pericardium sluice (3).

Figure 3:
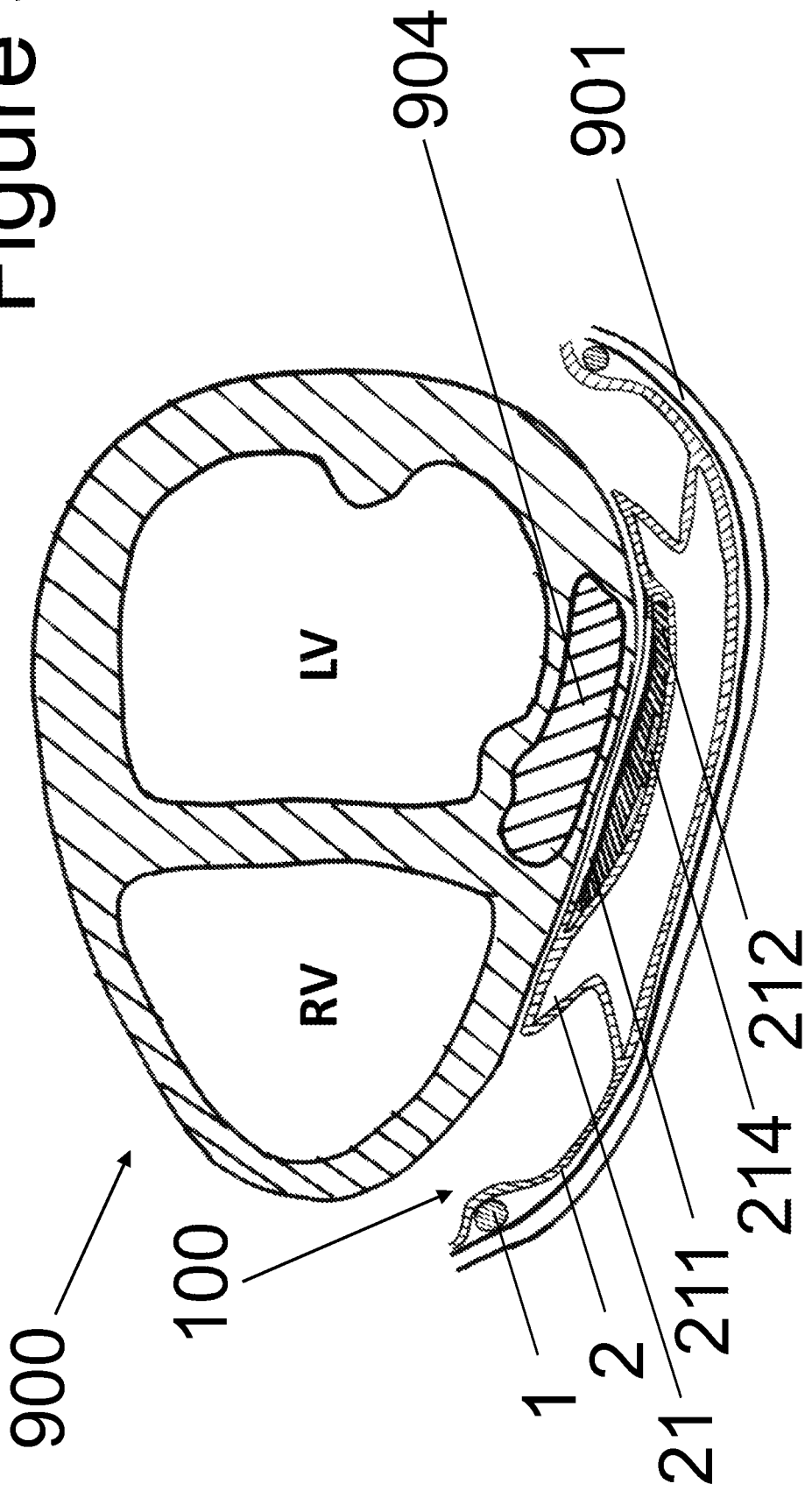
FIG. 3 shows a section through a heart having an infarction which is held by an inflatable, pneumatic chamber and substance carrier located thereon.

FIG. 3 shows a section through a heart (900) around which is placed an embodiment of the implant (100) which is in turn surrounded by the pericardium (901). In the wall of the heart, infarction tissue (904) is schematically distinguished from intact tissue of the heart (900). An expandable unit (21) may be positioned such that it completely covers a limited part of the surface of the heart (900) which lies directly above the infarction area. The expandable unit (21) is shown in this exemplary embodiment as an inflatable, bellows-like chamber. The expandable unit (21) may also differ from the form of a set of bellows. The underside of the expandable unit (21) is formed from part of the sleeve (2) in this embodiment. The underside of the expandable unit (21) may also be designed separately and then affixed to the sleeve (2), for example through gluing, welding or vulcanisation. With the aid of the expandable unit (21), the substance carrier (211) may be brought into contact with the surface of the heart. The substance carrier (211) is represented in this embodiment as a pocket with an opening on the end face. The opening on the end face allows the substance to pass from the substance carrier (211) to the surface of the heart. The underside of the substance carrier (211) is part of the end face of the expandable unit (21) in this embodiment. The underside of the substance carrier (211) may also be designed separately and affixed to the end face of the expandable unit (21), for example by gluing, welding or vulcanization or alternatively by suspension or with the aid of Velcro fastenings.

In general, the substance carrier (211) may be positioned in any desired location on the surface of the sleeve (2), of the at least one expandable unit (21) or of the frame structure (21). In some embodiments, the substance carrier (211) may be positioned at least partially on at least one expandable unit (21). The surface covered by the substance carrier (211) may be identical to and coincident with the end face of the expandable unit (21) here. However, the surface covered by the substance carrier (211) may also be larger or smaller than the end face of the expandable unit (21). The surface covered by the substance carrier (211) may be influenced by the size of the area to be treated on the surface of the heart. In embodiments with substance carriers (211) which take up a larger surface area than the at least one expandable unit (21) covered thereby, the mechanical load introduced into the substance carrier (211) through expansion of the expandable unit (21) may have a therapeutic effect. A more detailed description of this point is provided in a subsequent section. If the contact between substance (212) or substance carrier (211) and the surface of the heart is not permanent, that is to say in some embodiments it is preferably controllable or at least settable, the substance carrier (211) may also be positioned in areas of the implant (100) in which there is no overlapping of the substance carrier (211) and at least one expandable unit (21).

Alternatively, an embodiment is also conceivable in which the substance carrier (211) covers a number of expandable units (21) and/or surfaces of the sleeve (2) without expandable units (21), for example if the design of the substance carrier (211) has a number of separate or connected partial areas with a substance (212) which may be brought into contact with the surface of the heart at different areas of the latter.

The shape of the substance carrier (211) or its footprint is represented as being rectangular in this embodiment. Alternatively, the substance carrier (211) may also be any desired shape in order to be more efficient when substance is inserted and to be able better to match the geometry of the area of the heart (900) to be treated. Also conceivable are substance carriers (211) which may contain a number of substances (212), which may be of different kinds, in separate locations.

The substance carrier may also comprise at least one sensor (214). The at least one sensor (214) may also be an electrode. The at least one sensor (214) may be used to detect at least one parameter in the substance carrier or the substance. The at least one sensor (214) may be a concentration measurement sensor, a pH sensor, an oxygenation sensor or a pressure sensor. Other types of sensor are also conceivable. If the at least one sensor (214) is an electrode and if at least two of them are mounted, for example, the electrical potential between the two locations in which the electrodes have been mounted may be measured. The at least two electrodes may also be used to apply an electrical voltage.

Figure 4:
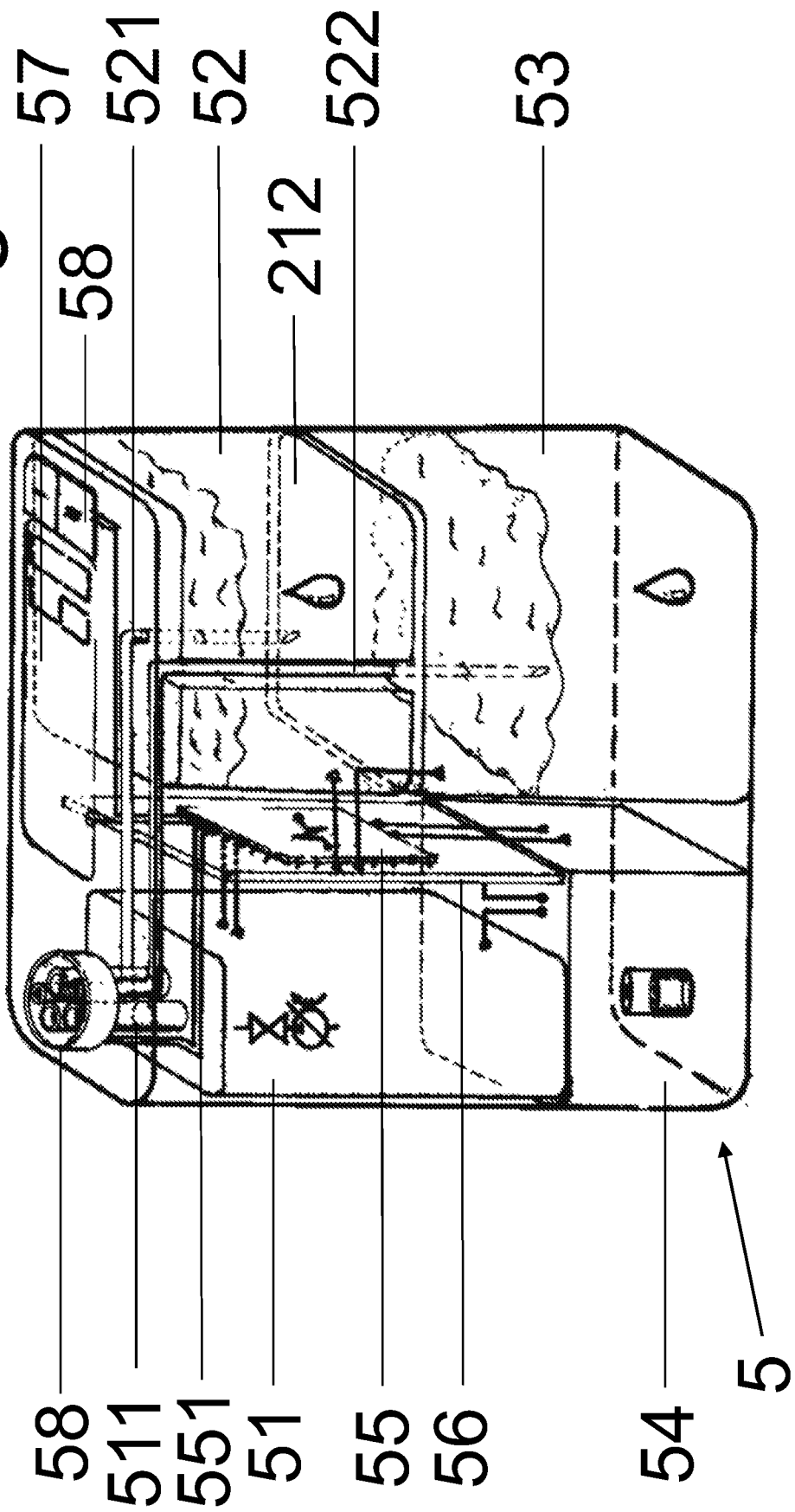
FIG. 4 shows a supply unit of an implant.

FIG. 4 shows an embodiment of the supply unit (5). The supply unit (5) may guarantee the supply of energy to the at least one actuator unit (51) of the at least one expandable unit, in particular for actuation of an inflatable, bellows-like pneumatic chamber. The supply unit (5) may supply the at least one sensor and/or the at least one electrode with energy. The supply unit (5) may supply energy to the at least one element for setting a parameter, for example at least one heating coil, in the at least one substance carrier, represented in the embodiment as a fillable and emptyable pocket. The energy supply for the at least two electrodes for applying an electrical voltage to the substance carrier, the pump device for the at least one reservoir (52) and the at least one control unit may be guaranteed by means of the supply unit (5). The supply unit (5) may also comprise at least one fillable and refillable reservoir (52) for at least one substance (212). The at least one reservoir (52) may be exchangeable. The at least one reservoir (52) may be insertable into the supply unit (5) and removable from the latter. The at least one reservoir (52) may also be designed to be separate from the supply unit (5). The at least one reservoir (52) may also be designed as a pouch, canister or bottle. The at least one reservoir (52) may be used, via at least one line (521) provided for that purpose, to carry a substance (212) to the substance carrier or into the substance carrier. The at least one reservoir (52) may have at least one pump device which may convey the at least one substance (212) to the at least one substance carrier and pump it out again. With the aid of the at least one reservoir (52), a continuous circulation of a substance (212) through at least one substance carrier may also be guaranteed in an embodiment as a pocket. In such an embodiment, the circulation may be guaranteed through a pump device. The at least one reservoir (52) may also have at least one filter device. The at least one filter device may comprise at least one membrane. The at least one membrane may be semipermeable. The at least one membrane may serve to prevent or to exclusively allow at least one substance (212) to pass from one partial space of the at least one reservoir (52) into the at least one other partial space of the reservoir (52). The at least one line (521) may be open to the at least one substance carrier. The at least one line (521) may also be closed to the at least one substance carrier. The at least one line (521) may also be permeable to the at least one substance carrier in respect of at least one substance (212) and at the same time impermeable in respect of at least one substance (212). The at least one line (521) may be semipermeable in the area in which the at least one substance carrier is located. A further discharge line (522) may run away from the substance carrier back to the reservoir (52). The at least one discharge line (522) may also be an extension of the at least one delivery line to the substance carrier. The at least one discharge line (522) may also not be connected to the reservoir (52). The at least one discharge line (522) may lead into a further, separate reservoir (53).

The supply unit (5) has an energy store with the aid of which the at least one expandable unit may be driven. The energy store may be in the form of an accumulator (54) which provides electrical energy in order to be able to expand the expandable unit. The accumulator (54) may be changed. The supply unit (5) may also contain a pressure reservoir which provides a compressed gas in order to be able to expand an inflatable chamber. Suitable gases are, inter alia, compressed air, $CO_2$ or noble gases. The housing of the supply unit (5) itself may serve as a pressure reservoir housing. This has the advantage that the cavity nevertheless provided in the housing may be used and an embodiment with a separate pressure reservoir may be dispensed with. The supply unit (5) may also contain pumps, valves, sensors and at least one display (57). The supply unit (5) may also comprise at least one microprocessor (55) on a microprocessor circuit board (56) which is able to receive and to process data from the at least one sensor. If the supply unit (5) is carried outside the body, the energy to be provided may be transferred through a direct connection via a cable, or wirelessly, for example through electromagnetic induction. The at least one microprocessor (55) may also control the actuation of the at least one expandable unit and/or regulate the circulation of the at least one substance (212) from the reservoir (52) via at least one substance line into the substance carrier and if applicable back again into the at least one reservoir (52) or at least one other reservoir (53).

The supply unit (5) may also be designed to be at least partially inside the body. For example, a separate pressure reservoir, for example for the purposes of refilling with a pressurized fluid, may lie inside the body. Alternatively, the at least one accumulator (54) for operation of the energy-consuming components of the implant may also lie inside the body. The data from the at least one sensor may likewise be transferred directly via a cable or wirelessly using radio technology, such as Bluetooth.

The implant may also comprise a cable harness which connects the at least one expandable unit and/or the at least one sensor or the at least one electrode to the supply unit (5). A detailed description of the cable harness is provided in a previous section. In the case of a multi-part cable harness, a cable with a plug part may be mounted on the at least one expandable unit and/or on the at least one sensor or the at least one electrode and a cable may also be mounted on the supply unit (5) at the end of which a plug part is likewise preferably located.

The supply unit (5) may have a wireless communication interface. By means of the latter, data may be transmitted for the purposes of assessment or forwarding, for example to the control and monitoring units described in a previous section. This wireless connection may, for example, be a WLAN or a Bluetooth connection.

All lines, for example at least one pneumatic line (511), at least one electrical line (551) and/or at least one substance line (521), may, to facilitate handling, be combined in the female part of a multiconnector (58). A detailed description of this multiconnector is provided elsewhere.

The supply unit (5) may also have at least one operating element (58) via which at least one function of the supply unit (5) may at least be monitored. The at least one operating element (58) may also serve to set at least one parameter or one function of the supply unit (5). For example, the mass flow of the substance (212) may therefore be monitored and/or set.

Figure 5:
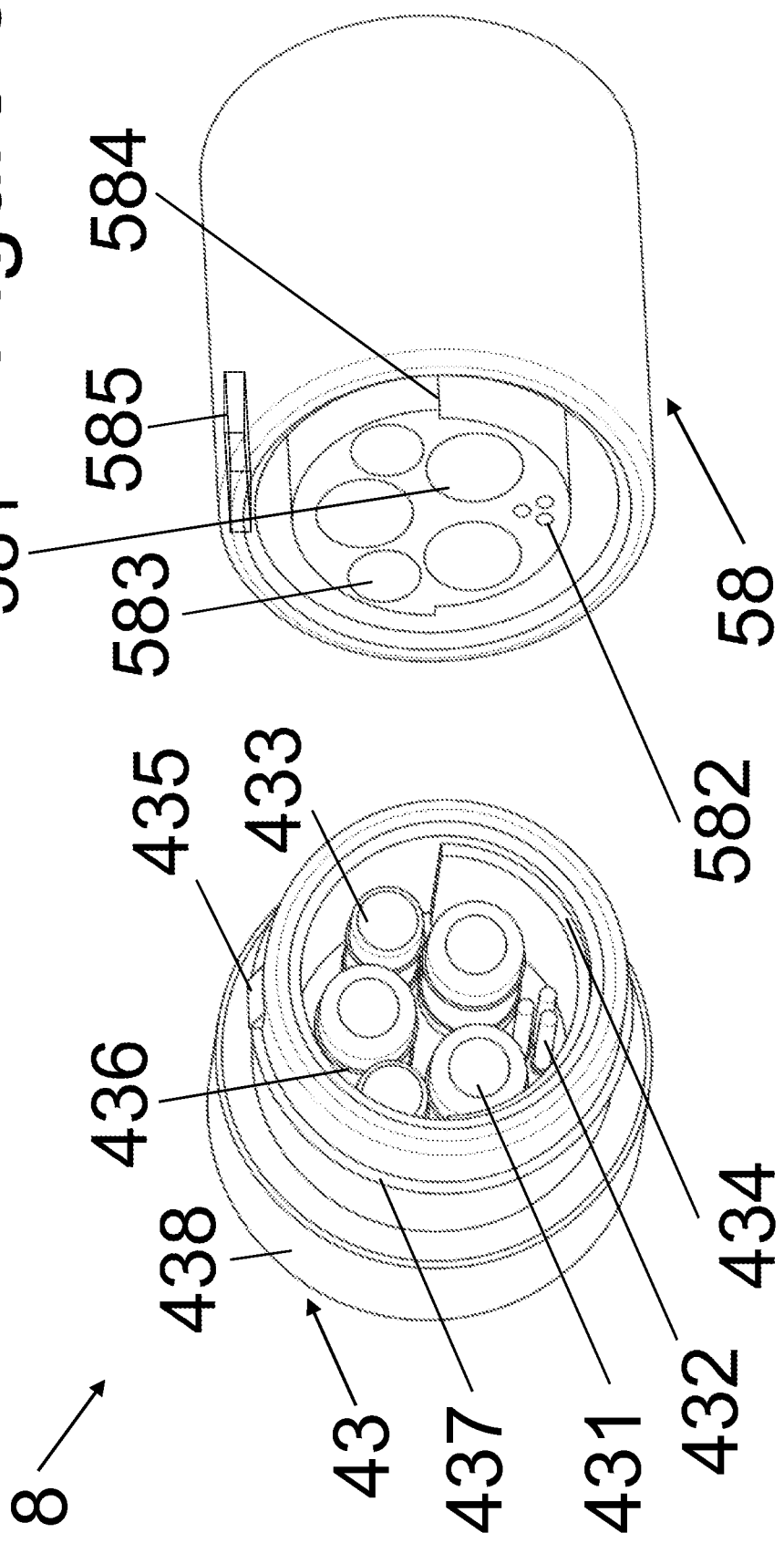
FIG. 5 shows a multiconnector with which the cable harness of an implant may be coupled to a supply unit.

FIG. 5 shows an embodiment of the multiconnector (8) which comprises two complementary plug parts, a male plug part (43) and a female plug part (58). The male plug part (43) comprises at least one connection (431) to at least one pneumatic or hydraulic line, at least one connection to at least one electrical line (432) and at least one connection (433) to at least one substance line. The complementary female plug part (58) comprises at least one connection (581) to at least one pneumatic or hydraulic line, at least one connection to at least one electrical line (582) and at least one connection (583) to at least one substance line. The embodiment shown in FIG. 5 comprises connections for three pneumatic lines (431, 581), three electrical lines (432, 582) and two substance lines (433, 583). Advantages of the multiconnector (8) are the compact spatial bunching together of different types of line, easy handling during coupling and uncoupling and the easy sealability.

The multiconnector (8) may also contain devices for centring (434, 584), for example in the form of a centring pin (434) and complementary shape (584) which guarantees correct orientation for problem-free joining of the two complementary plug parts (43,58). The cohesion of the plug connection may be assured through a coupling mechanism, for example a reversible, non-destructive snap lock (435, 585). In the embodiment shown, a snap lock (435) is depicted on the male plug side (43) which may be plugged into the complementary lock (585) provided for that purpose on the female plug side (58). The snap lock (435) may in some embodiments of the multiconnector (8) also serve as a centring device.

The multiconnector (8) may be sealed against the undesirable entry and/or exit of, for example, fluids, fluid-solid mixtures or granulates. Sealing against other media is also conceivable. Tightness is achieved through seals, for example in the form of sealing rings (436) as in the embodiment shown. Each line which has a lumen to be kept tight may be provided with an individual seal with sealing rings (436). Moreover, the multiconnector (8) may also be sealed overall. In the embodiment shown, this may be a sealing ring (437) mounted on the plug sleeve (438) of the male part (43).

Figure 6:
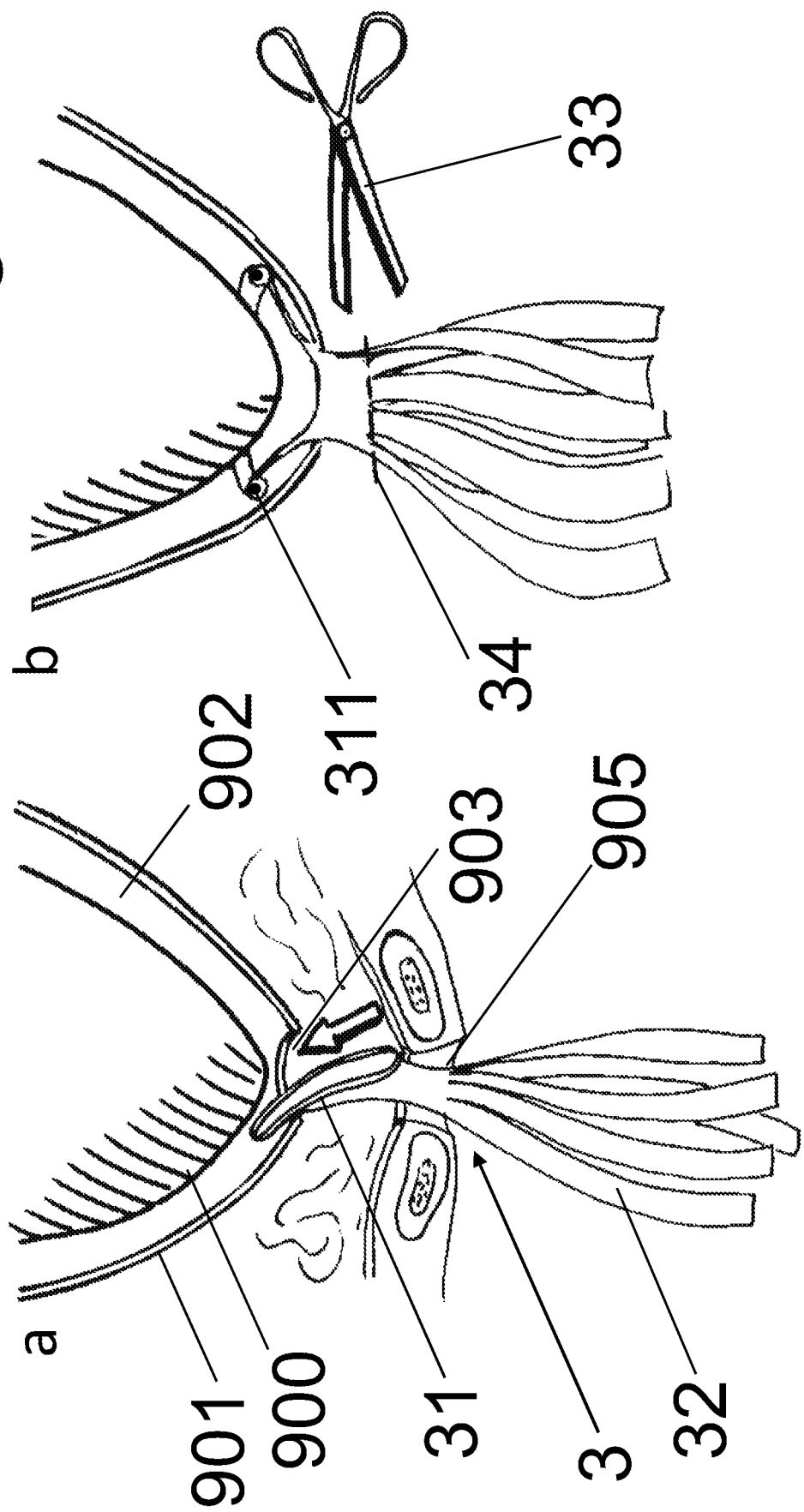
FIG. 6 shows the process for inserting a sluice into the pericardium.

FIGS. 6a and 6b show the process for inserting an embodiment of the pericardium sluice (3) through a surgically made access (905) and a surgically made opening (903) into the pericardial cavity (902). The pericardium sluice (3) has a proximal end and a distal end. The proximal end may have at least one lamella (32). The distal end has a sealing lip (31). The proximal end of the pericardium sluice (3) faces the operator during implantation and the distal end faces the patient. The material used for the pericardium sluice (3) is explained in more detail in a previous section. The material of the pericardium sluice (3) may be selected such that the pericardium sluice (3) may undergo considerable elastic deformation. This property is advantageous during the process of inserting the pericardium sluice (3) into the pericardial cavity (902). The material of at least part of the pericardium sluice (3) may be a polymer. The material of at least part of the pericardium sluice (3) may be silicone, polytetrafluoroethylene (PTFE) or polyurethane (PU). The material of at least a further part of the pericardium sluice (3) may be steel, a shape memory alloy or a polymer differing from those specified above or a plastic. The sealing lip (31) may, for example, contain a core (311) made out of a stiffer material which may increase the dimensional stability of the pericardium sluice (3). The pericardium sluice (3) may also be coated on the inside and/or on the outside so that friction between the pericardium sluice (3) and components inserted therein may be set. In some areas, greater friction may be advantageous (for example on the outside in contact with body tissue), while in other areas friction may be reduced by means of the coating, for example for easier insertion of a delivery system or of the implant.

The pericardium sluice (3) may be made out of at least one part. The pericardium sluice (3) is preferably designed to be rotationally symmetrical. It comprises lamellae (32) at the proximal end, a neck region and a sealing lip (31) which may have a diameter differing from the neck region. The sealing lip (31) preferably has a larger diameter than the neck region of the pericardium sluice (3) so that self-retention may occur after the pericardium sluice (3) has been inserted into the pericardial cavity (902). The diameter of the sealing lip (31) may be larger by a factor of 1.0 to 2.0 than the diameter of the neck region, while it may be larger by a factor of 1.05 to 1.2 than the diameter of the neck region.

The pericardium sluice (3) may, inter alia, serve to produce and maintain an insertion channel for the minimally invasive implantation of the implant. The pericardium sluice (3) may, with its outer surface and/or with a sealing lip (31), close and/or seal an opening (903) in the pericardium (901) and produce an inner lumen as a feed channel for implantation of the implant.

The lumen of the neck region may have a diameter of 5 mm to 100 mm, preferably 40 mm to 80 mm. The pericardium sluice (3) may be made out of a hose. Alternatively, the pericardium sluice (3) may consist of separate parts for the widening towards the sealing lip (31), the neck region and the lamellae (32) at the proximal end. The widening area and the neck region of the pericardium sluice (3) may also be made out of one part, while the lamellae (32) likewise represent a separate part which may be coupled to the other part for example by gluing or welding or some other joining technique. The materials of the different parts may be the same or different. It may be advantageous to design one part of the pericardium sluice (3) to be stiffer than the other. The wall thickness of the pericardium sluice (3) may be 0.2 mm to 4 mm. The wall thickness of the pericardium sluice (3) may be 0.4 mm to 2.5 mm. The size of the lumen produced by the pericardium sluice (3) may be set via the diameter. The stiffness of the pericardium sluice (3) may be set by the wall thickness. The wall thickness may vary locally. In certain places, for example in the area of the widening towards the sealing lip (31) or in the neck region, the wall thickness may be greater in order to facilitate insertion of the implant as the pericardium sluice (3) may be deformed in a more defined manner. At the proximal end, the pericardium sluice (3) may have lamellae (32) which protrude in the direction of the longitudinal axis of the sluice. If the pericardium sluice (3) is thermoformed, for example out of a continuous piece of hose, or if the pericardium sluice (3) is produced through casting, the lamellae (32) may also be produced by cutting along the axial direction of the pericardium sluice (3) or subsequently coupled to the pericardium sluice (3), for example by gluing. There may be 1 to 16 lamellae (32), preferably 2 to 6 lamellae (32) along the circumference of the pericardium sluice (3). The lamellae (32) may be arranged equidistantly along the circumference, which leads to equally wide lamellae (32). They may also be at different distances from one another, which leads to lamellae (32) of different widths. During implantation, the lamellae (32) of the pericardium sluice (3) may be positioned at least partially outside the body and serve to stretch the pericardium sluice (3). The lamellae (32) may have a spreading effect in that they may be pulled in a radial direction. The lamellae (32) may serve to spread the pericardium sluice (3) radially as evenly as possible. The lamellae (32) may thereby produce the largest possible lumen clinging to the cut in the skin and body covering. If more axial cuts are made, that is to say if there are more lamellae (32), the spreading process and the clinging of the pericardium sluice (3) to the shape of the cut in the skin and body covering are adjusted more finely. Lamellae (32) of differing widths along the circumference may serve to adjust the spreading and the clinging of the pericardium sluice (3) in different circumferential segments of the pericardium sluice (3) with differing fineness in order, for example, to take account of different tissues with different material properties or the individual body shape of the patient. The lamellae (32) may serve to adjust the entry depth of the pericardium sluice (3) by its being pulled more or less strongly. If it is pulled more strongly, the entry depth of the pericardium sluice (3) may be reduced, while if it is pulled less strongly, the entry depth of the pericardium sluice (3) may be increased. The lamellae (32) may serve to set a constant entry depth of the pericardium sluice (3).

The pericardium sluice (3) may also be made by casting. The pericardium sluice (3) may also have a differing diameter in the axial direction. In the present embodiment, the pericardium sluice (3) may taper from the upper end down to a certain point underneath the upper end and may then widen again below that point.

In addition, in the area of the widening of the pericardium sluice (3) towards the sealing lip (31) and/or in the neck region, a porous structure or a fabric at least partially covering the corresponding areas may be provided, for example a felt, expanded PTFE, Dacron or another suitable biocompatible synthetic fabric. This has the advantage that the pericardium sluice (3) grows together better with the surrounding body tissue in said places and therefore improves both the mechanical resilience and the tightness.

An alternative embodiment may comprise a further component, an insertion aid, which may be rotationally symmetrical and preferably consists of a stiffer and/or smoother material, that is to say potentially with lower friction in relation to components to be inserted, than the pericardium sluice (3). The measures specified above for setting the friction may also be used for this component. This component may serve to temporarily widen and support the implantation channel and may reduce the tendency of the pericardium sluice (3) to crumple and kink when it comes into contact with embodiments of the implant to be inserted. After implantation, this component may remain in or be removed from the pericardium sluice (3).

FIG. 6a shows an embodiment of the pericardium sluice (3) during insertion into the pericardial cavity (902). Implantation may be carried out between two ribs. Owing to its considerable elastic deformability, the pericardium sluice (3) may be passed through an opening (903) in the pericardium (901) which, at its largest elongation, is smaller than the diameter of the pericardium sluice (3) in its undeformed state.

FIG. 6b shows the position of the pericardium sluice (3) after insertion into the pericardial cavity (902). On account of the size relationship described above between the opening (903) in the pericardium (901) and the diameter of the sluice, a non-positive connection may be made between the pericardium (901) and the pericardium sluice (3). This connection may increase the stability and the positional accuracy of the pericardium sluice (3) inside the pericardial cavity (902). The neck of the pericardium sluice (3) extending towards the sealing lip (31) may abut against the pericardium (901) and produce a self-retaining effect, thus increasing the stability and the positional accuracy of the pericardium sluice (3) inside the pericardial cavity (902). The sealing lip (31) may likewise increase the stability and positional accuracy of the pericardium sluice (3) inside the pericardial cavity (902) because it may be an area of increased material stiffness and may therefore be less deformable.

After insertion of the implant, the pericardium sluice may remain at least partially in the body. The lamellae (32) of the pericardium sluice (3) may also serve another function after implantation of the implant. They may serve to additionally fix the pericardium sluice (3) to the fixing sleeve, for example through wrapping, tying, stitching, sticking or welding. Other methods of fixing are also conceivable. They may also perform no function after implantation of the implant. In order to minimize the amount of exogenous material remaining in the body, these lamellae (32) may be separated off. The separation of the lamellae (32) may be carried out by means of a separation device (33), for example a pair of scissors or forceps, at a separation plane (34) adequate for the application concerned. Separation may also be carried out without any separation device if, for example, predetermined breaking points are provided on the pericardium sluice (3) in the place of intended separation at the separation plane (34).

Alternative embodiments may have a multi-part pericardium sluice (3). Such embodiments may, for example, have a sealing element (for example in the form of a further sealing lip) which may be coupled to a further part so that the two parts achieve the sealing effect together. One part of the seal may be located here inside the pericardial cavity (902), the other outside it. The coupling of the two parts means that the pericardium opening (903) may be closed and is thereby sealed.

Figure 7:
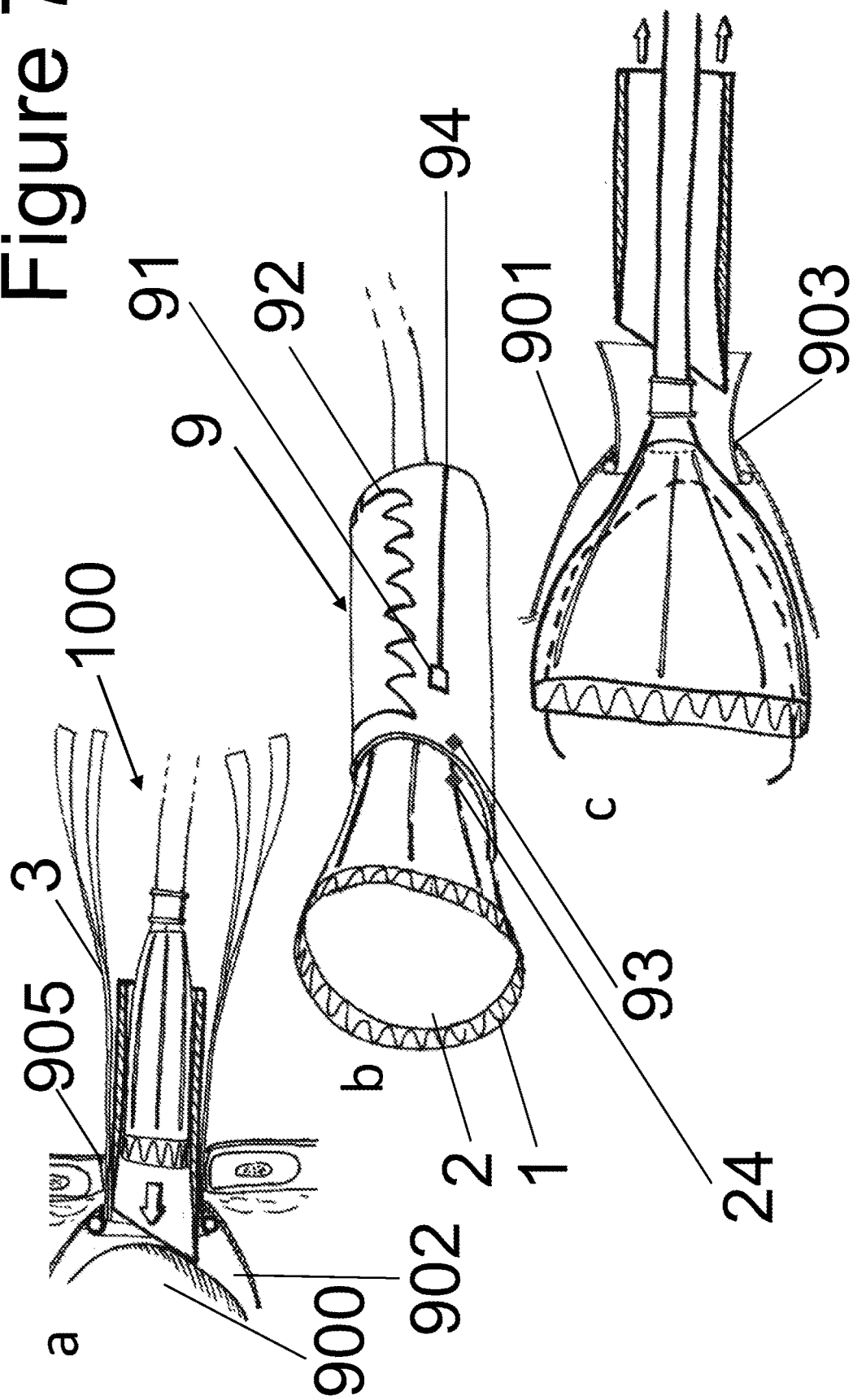
FIG. 7 shows an assembly consisting of a sluice, a delivery system inserted into it and an embodiment of the implant inserted therein. The process for bringing the implant out into the pericardium is shown.

FIGS. 7a, b and c show the insertion of the implant (100) via a delivery system (9) into the pericardial cavity (902). FIG. 7a shows a position of the delivery system (9) inside the pericardium sluice (3) just under the apex of the heart and partially inside the pericardial cavity (902).

The delivery system (9) may be an essentially tubular delivery system (9). The delivery system (9) has a proximal and a distal side. The proximal side of the delivery system (9) faces the operator during implantation and the distal side faces the patient. In this embodiment, the delivery system (9) is represented as a straight, cylindrical tube with a slanted distal end. The delivery system (9) may also differ from the straight, cylindrical tube form. The delivery system (9) may be rotationally symmetrical with regard to a straight reference line. The delivery system (9) may also differ from rotational symmetry with regard to a straight reference line. The straight reference line may also be the union of a number of symmetry planes (tube with a polygonal cross section). The straight reference line may also be the union of focus points of all cross sections of the tube (tube with any desired cross section). The reference axis may also be a reference line. A reference line may be straight. A reference line may also be curvilinear. The definition of the reference line suggests the possible course of the tube. In its embodiment as a straight, cylindrical tube, the delivery system (9) may have a constant wall thickness. The wall thickness of the tubular delivery system (9) may also be variable. The wall thickness may be variable in the axial direction and in the circumferential direction. The variable wall thickness may serve to influence the insertion of the implant (100) into the delivery system (9), the passing of the implant (100) through the delivery system (9) or the removal of the implant (100) from the delivery system (9). The variable wall thickness may facilitate the insertion of the implant (100) into the delivery system (9), the passing through the delivery system (9) or the removal from the delivery system (9). A variable wall thickness in the case of an embodiment in the form of a cylindrical tube may mean that the internal diameter of the tube may change. This may facilitate the insertion of the implant (100) into the delivery system (9), the passing through the delivery system (9) or the removal from the delivery system (9). A variable wall thickness in the case of an embodiment in the form of a cylindrical tube may also mean that the external diameter of the tube may change. A variable wall thickness in the case of an embodiment in the form of a cylindrical tube may also mean that the internal and external diameter of the tube may change. As a result, the consequences of both changes in diameter may be combined. In the present embodiment, the wall thickness declines linearly to the end at which the implant (100) is intended to exit. The external diameter of the embodiment shown remains constant here, while the internal diameter increases towards the exit and has a funnel-shaped geometry.

The implant (100) may be inserted into a delivery system (9). The insertion of the implant (100) into the delivery system (9) may be carried out through a radial compression of the implant (100). The assembly consisting of the delivery system (9) and the device according to the invention may be carried to the heart (900) through a pericardium sluice (3) which is located partially inside the pericardial cavity (902) and partially outside the pericardium, but inside the body and partially outside the body.

In one embodiment in which the frame structure (1) consists of an elastically compressible or self-expanding material, the implant (100) may expand on removal from the delivery system (9) owing to the elastic energy stored on insertion into the delivery system (9) in the case of an elastically compressed material or alternatively, in the case of a shape memory alloy, owing to the changed temperature inside the body, and may at least partially surround the heart (900).

FIG. 7b shows the delivery system (9) and an embodiment of the implant (100) which has partially emerged from the delivery system (9) and is in the process of expansion. At least one sensor (91) and at least one element for influencing at least one parameter in or on the delivery system (9), for example a heating coil (92), may be mounted on the surface of the delivery system (9).

The at least one sensor (91) may be mounted on the inner surface or on the outer surface of the delivery system (9). Alternatively, the at least one sensor (91) may be incorporated into the wall of the delivery system (9). The at least one sensor (91) may serve to detect various parameters in the delivery system (9) or the surroundings. The sensor (91) may be a temperature sensor, a pressure sensor, a pH sensor, an oxygen sensor, a $CO_2$ sensor, an optical sensor or a conductivity sensor. The electrical line (94) may connect the sensor to an evaluation device. The at least one sensor may alternatively also be operated wirelessly.

In the present embodiment, the at least one element for influencing at least one parameter in or on the delivery system (9) is designed as a heating coil (92). By means of the heating coil (92), for example, the expansion behaviour of the self-expanding frame structure (1) may be set. The at least one element for influencing at least one parameter may be mounted on the inner surface of the delivery system (9). The at least one element for influencing at least one parameter may also be mounted on the outside surface of the delivery system (9) or incorporated into the wall of the delivery system (9). Influenceable parameters may control the temperature inside and/or surrounding the delivery system (9), the concentration of conductivity-influencing substances, the pH value of influencing substances or the oxygen and $CO_2$ content-influencing substances inside and/or surrounding the delivery system (9). A further parameter may be the static and dynamic friction between implant (100) and delivery system (9) which may be set through suitable additions such as lubricant. If the supply, for example, of electrical energy is required for operation of the at least one element (94) for influencing at least one parameter in or on the delivery system (9), this may be carried out by means of the electrical line (94).

The end faces of a delivery system (9) may differ from a planar shape at at least one end of the tube. The end faces may take the form of a spatially running level band. The end faces may also be planar, but tilted towards the central axis of the delivery system (9), that is to say the normal of the end face and the tangent of the reference line of the delivery system (9) at the focus point of the end faces form an angle that is zero or more. The distal end face of the delivery system (9) is preferably slanted, facilitating the insertion of the implant (100). Changing the shape and orientation of at least one end face of the delivery system (9) with respect to an embodiment with plane end faces, the normals of which are parallel or antiparallel to the tangent of the reference line of the delivery system (9) at the focus point of the end faces may facilitate and/or improve the insertion of the delivery system (9) into the pericardial cavity (902) through the pericardium sluice (3), the expansion of the frame structure (1) and the surrounding of a heart (900) through the frame structure (1) and the sleeve (2) because anatomical conditions such as the position of the ribs and of the heart (900) may require operational access to the heart (900) at a certain angle to the longitudinal axis of the heart. The slant with respect to the surface normals of an embodiment with a planer end face may be between 30° and 90°, or between 45° and 80°.

The delivery system (9) may be designed to be at least partially transparent. The advantage lies in the fact that the embodiment of the implant (100) inserted into the delivery system (9) may be aligned with the aid of corresponding markings (24, 93) in relation to the delivery system (9) and a precise delivery into the body and insertion into the pericardial cavity (902) may be guaranteed. These markings (24, 93) may be radiopaque.

FIG. 7c shows an embodiment of the implant (100) which at least partially surrounds a heart (900) after removal from the delivery system (9) through the pericardium sluice (3). The pericardium sluice (3) may, as described in a previous section, remain in the body in order to close off and seal the opening (903) in the pericardium (901). The delivery system (9) may be removed from inside the body again after removal of the implant (100) through the pericardium sluice (3).

Figure 8:
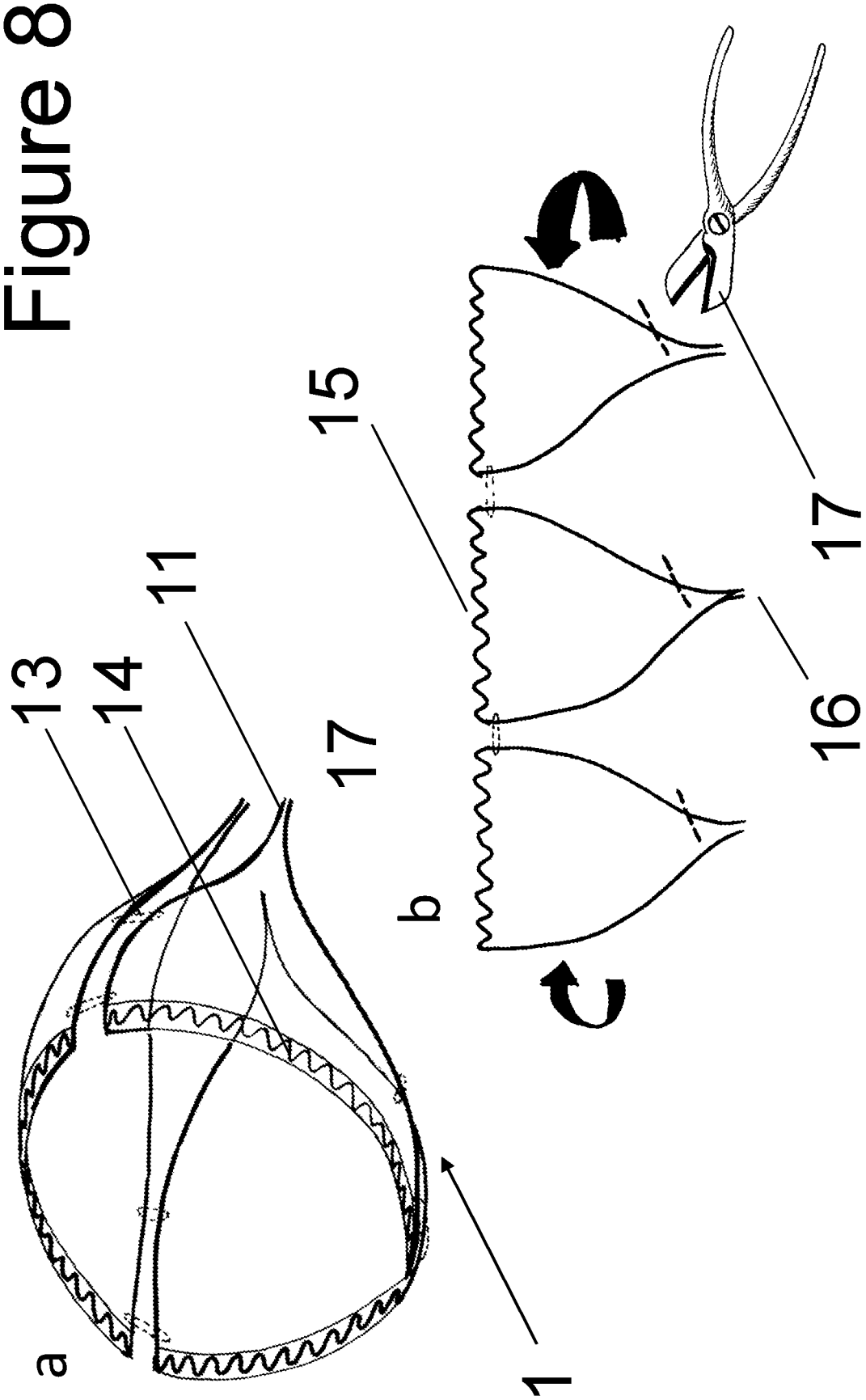
FIG. 8 shows a three-dimensional and an unrolled view of the expandable frame structure.

FIGS. 8a and b show an embodiment of the frame structure (1) which may provide form and stability to the implant generally and to a sleeve inserted into the frame structure (1) and which may guarantee the expansion of the implant after removal from a delivery system into the pericardial cavity.

FIG. 8a shows a three-dimensional view of an embodiment of the frame structure (1) of the implant. The frame structure (1) in this embodiment is represented as a wire framework made out of three wires (14).

The frame structure (1) may be designed in the form of a lattice. The lattice may consist of a continuous material from which parts have been removed or in which the openings have been made. For example, the frame structure (1) may be made out of a tube or an individually formed frame structure sheath in which the openings are cut.

Preferred here is a method in which small slots are made in a tube, for example by means of laser cutting ("slotted tube"). The slotted tube may have a diameter of 4 mm to 30 mm, or a diameter of 6 mm to 20 mm. The slotted tube may be between 5 cm and 20 cm in length, or between 8 cm and 15 cm in length.

A slotted tube which consists of a shape memory alloy is then stretched over shaping mandrels and normalized by mean of a heat treatment so that the stretched form represents the new natural configuration of the tube. These stretching and heat treatment processes may be repeated with larger and larger mandrels until the slotted tube may finally be stretched over a form which corresponds to a copy of the heart and whereby, under heat treatment, the shape of the heart is transferred to the slotted tube. The production of the mandrel is described in more detail in a subsequent section. The slotted tube is therefore transferred into a frame structure (1) consisting of a lattice, the shape of the frame structure (1) corresponding to a copy of the heart. The slots in the tube pass here into the openings of the lattice. The openings are delineated here through struts (14). A number of struts (14) of an opening form individual cells of the lattice here. The lattice may preferably have diamond-shaped cells. The shape of the cells may be modified through suitable cutting when slotting the tube. Alternatively, cells with a hexagonal honeycomb structure or cells with a polygonal structure may thereby be produced.

Through suitable cutting, longer or shorter cells may be produced. Through the length and number of the slots, the number of rows of cells along the longitudinal axis of the heart of the frame structure (1) is also defined. Longer slots lead to longer struts (14), while shorter slots lead to shorter struts (14) in the frame structure (1). Longer struts (14) are more flexible than short struts (14) here. The length of the cells is 5 mm to 50 mm, in particular 10 mm to 30 mm. The length of the cells may vary from cell row to cell row and may also be the same or vary within a cell row.

As a result of the number of slots along the circumference of the tube, the number of cells along the circumference of the frame structure (1) is determined. Fewer slots along the circumference lead to a greater width of the resulting struts (14), while an increase in the number of slots along the circumference leads to thinner struts (14). Wider struts (14) are less flexible here than thinner struts (14). In the longitudinal direction, between 4 and 15 cuts may be made in a row one after another, or between 5 and 10 cuts may be made in a row one after another. In the circumferential direction, 14 to 80 such rows of cuts may be distributed around the circumference of the tube, or 20 to 45 such rows of cuts may be distributed around the circumference, or 26 to 36 such rows of cuts may be distributed around the circumference. During production, the cuts may be distributed evenly around the circumference of the tube (equidistantly), thereby achieving homogeneous structural stiffness in the lattice. Alternatively, the cuts may be distributed unevenly (not equidistantly) with respect to one another so that areas with cells having wider struts (greater structural stiffness) and areas with cells having narrower struts (lesser structural stiffness) may be achieved. Areas in which greater structural stiffness is desired may, for example, be areas which cover the left ventricle of the heart or areas which form the abutment for the expandable units. Areas in which a lesser structural stiffness is desired are, for example, areas of the right ventricle.

The wall thickness of the tube into which the slots are cut gives the strut height of the frame structure (1). A greater strut height leads to stiffer properties of the lattice. A lesser strut height leads to more flexible properties of the lattice. Through use of a tube with regionally differing wall thickness, areas of lesser or greater structural stiffness may therefore be produced. The wall thickness of the tube may be between 0.2 mm and 2 mm, preferably between 0.4 mm and 1.5 mm, in particular between 0.6 min and 1 mm. The wall thickness of the frame structure (1) is the same as the wall thickness of the tube.

If the number of slots is the same, a greater tube diameter results in a greater strut width. The method of production guarantees that the lattice of the expanded frame structure (1) may also be compressed again to the size of the tube from which it was cut. This may be helpful in particular if the frame structure (1) is intended to be inserted into a delivery system described above. However, the frame structure (1) may also be compressed to any intermediate size between the fully expanded, heart-shaped lattice and the original tube diameter. By using, for example, a shape memory alloy, the frame structure (1) may expand into the heart shape of its own accord upon implantation/removal from the delivery system. The exerting of external forces through further devices is unnecessary when using a shape memory alloy. In particular, the length of the cells and/or struts (14) of the lattice determines the opening angle on expansion of the frame structure (1) here, in particular in the case of the self-expandable frame structure (1).

Instead of a lattice, the frame structure (1) may also consist of a mesh of wires (14). The wires (14) form crossing points which may be firmly connected to one another. For example, the wires (14) may be welded to one another at the crossing points. The connecting of the wires (14) at crossing points increases the stability of the frame structure (1). The crossing points may also not be connected to one another. This may increase the flexibility of the frame structure (1) and hence make the frame structure (1) easier to compress. This may be helpful in particular if the frame structure (1) is intended to be inserted into a delivery system with a catheter having a smaller diameter. The frame structure (1) may also have certain crossing points firmly connected to one another and other crossing points not firmly connected to one another. Through a suitable choice of crossing points which are firmly connected to one another and crossing points which are not firmly connected to one another, the stability and flexibility of the frame structure (1) may be adjusted. Areas which require greater stability in the implanted state may be stabilized through the connection of wires (14) at crossing points. These may, for example, be areas which serve as abutments for expandable units. Such abutments may be located directly under an expandable unit or next to areas with expandable units. Areas which require greater flexibility may be areas which have to be compressed to a greater extent than other areas on insertion into a delivery system. Areas which may require greater flexibility may also be areas in which greater flexibility helps the natural movement of the heart.

Adjustments may also be made through the choice of material used, through changes of material in certain areas or through application of, for example, energetic radiation, such as heat. The frame structure (1) preferably has openings which are formed by the wires (14) of a wire mesh, the struts (14) of a lattice or the holes in a frame structure sheath. These openings allow the compression of the frame structure (1), they allow the exchanging of substances from inside the frame structure (1) with areas outside the frame structure (1) and vice versa, they reduce the quantity of material to be used for the frame structure (1) and they allow greater flexibility of the frame structure (1). Forms which can only be produced with difficulty using continuous materials can be formed more easily with mesh-like or lattice-like structures. The openings may be quadrangular, diamond-shaped, round or oval. The openings defined by the wires (14), the struts (14) or the holes in a frame structure sheath have a diameter of approximately 1 mm to 50 mm, preferably from 3 mm to 30 mm, preferably from 5 mm to 20 mm. The diameter of an opening is defined as a pin opening, that is to say the diameter of the opening constitutes the largest diameter of a cylindrical pin which may be passed through an opening (a cell, a hole).

The frame structure (1) preferably consists of a material which allows expansion. The frame structure (1) is preferably formed from a material which is selected from the group consisting of nitinol, titanium and titanium alloys, tantalum and tantalum alloys, stainless steel, polyamide, polymer fibre materials, carbon fibre materials, aramide fibre materials, glass fibre materials and combinations thereof. For a self-expanding frame structure (1), a material which is made at least partially out of a shape memory alloy is suitable. Materials for shape memory alloys are, for example, NiTi (nickel-titanium; nitinol), NiTiCu (nickel-titanium-copper), CuZn (copper-zinc), CuZnAl (copper-zinc-aluminium), CuAlNi (copper-aluminium-nickel), FeNiAl (iron-nickel-aluminium) and FeMnSi (iron-manganese-silicon).

The frame structure (1) may also consist of a plastic, a composite material or a polymer, which have sufficient stiffness for expansion under the conditions described. For example, the frame structure (1) may be made out of polyethylene and is preferably produced by a casting process, for example injection moulding. Other plastics, fibre materials or composite materials are also conceivable.

The frame structure (1) preferably has a shape adapted to the individual shape of the patient's heart. The individual shape of the patient's heart may be reconstructed here from CT or MRT image data. The frame structure (1) is open at the distal, upper end (15) from the operator's point of view. The upper, distal edge of the frame structure (1) preferably has loops of a wire or stirrup which are formed from struts (14). The loops or stirrups may serve as anchoring points for a sleeve with at least one expandable unit. At the proximal, lower end of the frame structure (1) from the operator's point of view there is preferably an opening (16) through which one or more electric lines of the at least one sensor or the at least one electrode and/or lines of the at least one expandable unit may be passed. The shape of the frame structure (1) at least partially represents the shape of a natural heart, preferably the lower part of a heart. Specifics regarding the shape of the frame structure (1) are explained in more detail in a subsequent section of the description.

If there are two or more struts (14), the at least two struts (14) may be the same length, but may also be of different lengths. The cross section of the at least one strut (14) may be rectangular. The cross section of the strut (14) may also differ from the rectangular form, and may for example also be round, elliptical or polygonal. The at least one part of the frame structure (1) may consist of several wires (14) which may in each case be coupled in pairs. At least one couplable pair may also be designed to be uncoupled. Alternatively, the at least one part of the frame structure (1) may consist of at least one strut (14). The at least one part of the frame structure (1) may also consist of several struts (14) which may in each case be coupled in pairs. At least one couplable pair may also be designed to be uncoupled. The at least one wire (14) or the at least one strut (14) may be coupled so that different segments are connected to one another along the at least one wire or the at least one strut (14).

In the present exemplary embodiment, the three shaped wires (14) are connected to the respective neighbouring wire through two couplings (13) in each case. A coupling (13) may be carried out through material bonding, through positive locking and/or through non-positive locking. If the coupling (13) is designed as a material bond, the coupling partners may, for example, be welded or stuck to one another. If the coupling (13) is designed as a positive connection, this may, for example, be carried out through complementary coupling elements (13) on the at least two wire or strut segments to be connected. The coupling elements (13) here may be part of the at least two wire or strut segments, for example in the form of hooks, eyelets, buttons, loops or the complementary combination thereof for the respective wire segment or strut segment pair to be coupled. Alternatively, the connection partners, if designed as wires (14), may also be weaved or twisted. The coupling elements (13) may also be at least one individual component, for example in the form of rings, sleeves, clips, wires or clamps. The positive coupling (13) may also be carried out through at least one Velcro fastening and/or zip. If the coupling (13) is carried out through non-positive locking, the ends of the at least two wire or strut segments may be tied together using threads, fibres or cables. The ends of the at least one wire or of the at least one strut (14) may be brought together at the lower end of the implant. The ends may be coupled to one another. However, the ends may also be left uncoupled. The two ends of the at least one wire may be coupled. If there are at least three wires (14), one end of one may also be connected to one end of the neighbouring wire (14). The ends of the at least one wire (14) or the at least one strut (14) may serve to axially stiffen the implant (parallel to the longitudinal axis of the heart) and to axially position it securely in place. The axial positioning securely in place is achieved by the ends of the at least one wire or of the at least one strut (14) being affixed on or in the fixing sleeve which runs from the present embodiment of the implant away towards the supply unit. This connection may be brought about through positive locking, non-positive locking or material bonding. In the case of positive locking, the connection may be designed as the coupling (13) of two complementary connection partners in the form of a connection with feather keys, in the form of a hook-eyelet connection, a button-loop connection or a hook-loop connection. In the case of non-positive locking, this connection may be carried out in the form of a clamp connection or a connection using a threaded pin. In the case of material bonding, this connection may be carried out in the form of an adhesive connection or a welded connection.

The stiffness of the frame structure (1) in the axial, radial and circumferential direction may be set through the number of wires or struts (14). The stiffness of the frame structure (1) increases with the increasing number of wires (14) or struts (14) used. Alternatively, the stiffness of the frame structure (1) may be set through the number of pair-wise couplings of at least two wires (14) or struts (14). The stiffness of the frame structure (1) increases with the increasing number of couplings (13). The stiffness of the frame structure (1) may also be adjusted via the cross section of the at least one wire or the cross section of the at least one strut (14). A larger cross-sectional surface area may lead to greater stiffness of the frame structure (1). The thickness of the at least one wire or of the at least one strut (14) may be between 0.2 mm and 2 mm. The thickness of the at least one wire or of the at least one strut (14) may be between 0.4 mm and 1 mm. In the circumferential direction, the stiffness of the frame structure (1) may be set by an alternating course of the at least one wire or the at least one strut (14). The alternating course may be periodical. However, it may also differ from a periodical form. The parameters playing a role in setting the stiffness are the amplitude of the alternating course in the transverse direction and the number of maxima and minima of the wire or strut course. In the case of a periodic wire or strut course, the number of periods of the wire or strut course is reflected in the period length, a period having one maximum and one minimum. In the case of a periodic wire or strut course, an embodiment may be realized in sinusoidal form, in triangular form, in rectangular form, in polygonal form, sectionally in semicircular form or in a combination of these forms. The combination of the forms specified above may also lead to an aperiodic wire or strut course when viewed over the entire circumference. The wire or strut course may be the same in each part in an embodiment of the frame structure (1) consisting of at least two parts or may differ between the parts. The amplitude of the wire or strut course influences the stiffness of the frame structure (1) primarily, but not exclusively, in the circumferential and in the radial direction. An effect influencing axial stiffness may also be achieved. The expansion and compression behaviour of the expandable frame structure (1) may be influenced through the amplitude of the wire or strut course. The amplitude of the wire or strut course may be between 0 mm and half the total height of the frame structure (1) (the distance between the upper and lower ends of the frame structure (1)). The amplitude may be between 4 mm and 10 mm. The number of periods of the wire or strut course along the circumference may likewise be used to influence the stiffness of the frame structure (1) primarily, but not exclusively, in a radial and circumferential direction. An effect influencing axial stiffness may also be achieved. The number of periods in the wire or strut course along the circumference may be between 0 and 72, or may also be between 12 and 36. All of the possible ways of influencing axial, radial and circumferential stiffness specified in the description of the frame structure (1) may also be used in combination.

In the case of embodiments of the frame structure (1) consisting of at least one wire, at least one strut (14) may also be used and may be coupled to the at least one wire (14), which may additionally increase the stability and stiffness of the frame structure (1). In alternative embodiments of the frame structure (1) consisting of at least one strut (14), at least one wire (14) may also be used and may be coupled to the at least one strut (14), which may additionally increase the stability and stiffness of the frame structure (1). The axial, radial and circumferential stiffness of the frame structure (1) may also be set through the targeted combination of wires (14) and struts (14).

The material of the at least one wire or of the at least one strut (14) may enable the frame structure (1) to pass from a non-expanded state to an expanded state. The material of the at least one wire or of the at least one strut (14) may be a shape memory alloy. The material of the at least one wire or of the at least one strut (14) of the frame structure (1) may also differ from a shape memory alloy. The material may also be a spring steel or a polymer. The polymer may be polyurethane (PU), polypropylene (PP), polyethylene (PE), polycarbonate (PC), polyamide (PA), a superelastic polymer or a shape memory polymer. The frame structure (1) may also consist of a biodegradable material, for example polylactide, cellulose or polyglycolide, because this may have the advantage that an embodiment of the implant without any cable harness or supply unit, which consists overall of at least one biodegradable material, no longer has to be removed from the body after it has carried out its function. In the case of embodiments of the implant in which only the frame structure (1) consists of at least one biodegradable material, this may be advantageous because, for example, the risk of injury to the surrounding tissue caused by the frame structure (1) is reduced and the process of explantation without a frame structure (1) may be considerably easier. Such a frame structure (1) is broken down by the body over time. A frame structure (1) made out of a polymer may consist of struts (14) which can be deformed elastically from the expanded state in order to compress the frame structure (1) and insert it into a delivery system. On removal into the pericardial cavity, the frame structure (1) returns to its expanded state again. The expansion and compression of the embodiment of a frame structure (1) consisting of a polymer may be carried out with the aid of a shape memory effect or without the use of any shape memory effect. With increasing stiffness, the suitability of the frame structure (1) as an abutment, for example for the at least one expandable unit, may increase. In the case of low stiffness, a small amount of material may be used for the frame structure (1). The stiffness may be sufficient to provide the sleeve with position and shape. With a low but sufficient stiffness of the frame structure (1), the weight of the implant may be reduced. With a low but sufficient stiffness of the frame structure (1), insertion into a delivery system may be facilitated. The frame structure (1) may also primarily serve to position and shape a sleeve and may serve less as an abutment.

The frame structure (1) may have at least one recess which ensures that anatomical structures are not spatially impaired, for example the inferior vena cava. The recess may be produced such that the circumferential wire or strut course provides a recess in the area of the anatomical structure which is not supposed to be compressed.

At least one wire (14) or at least one strut (14) may also run in the circumferential direction. The at least one wire (14) or the at least one strut (14) in the circumferential direction may increase the stability of the frame structure (1). The at least one wire (14) or the at least one strut in circumferential direction may increase the stiffness in the circumferential direction. The number of wires (14) or struts in the circumferential direction may be between 0 and 10. It may be between 0 and 3. At least one wire (14) or at least one strut may also be partially axially orientated and partially orientated in the circumferential direction. The at least one wire (14) or the at least one strut (14) in the circumferential direction may increase the stability of the frame structure (1). The at least one wire (14) or the at least one strut (14) in the circumferential direction may increase the stiffness both in the axial direction and in the circumferential direction.

FIG. 8b shows a two-dimensional unrolling of the frame structure (1). In the present embodiment, the unrolled frame structure (1) consists of three wires (14), the two ends of each of them being brought together at the lower end of the frame structure (1). There they may be connected with the aid of a coupling (13). Possible connections may be an adhesive connection, a welding connection, a non-positive connection such as tying up, or a positive connection with hooks, eyelets, buttons or loops. At least one end of the at least one wire (14) or of the at least one strut (14) of the frame structure (1) may be clipped off afterwards or beforehand. The clipping of the frame structure through a separation device (17) or through predetermined breaking points provided in suitable places may reduce the quantity of exogenous material introduced into the body. The clipping may be perceived as a further option for adjusting axial or rotatory stiffness.

The at least one wire (14) may form a recess which may serve the purpose of not spatially impairing anatomical structures such as the inferior vena cava.

Using a suitable method of production, for example by laser cutting, segments of the frame structure (1) may alternatively be cut out of a sheet or a half-tube. The frame structure (1) may be produced through subsequent shaping (for example bending or contorting of the frame segment which is flat after the first production step) and coupling of the segments together.

Figure 9:
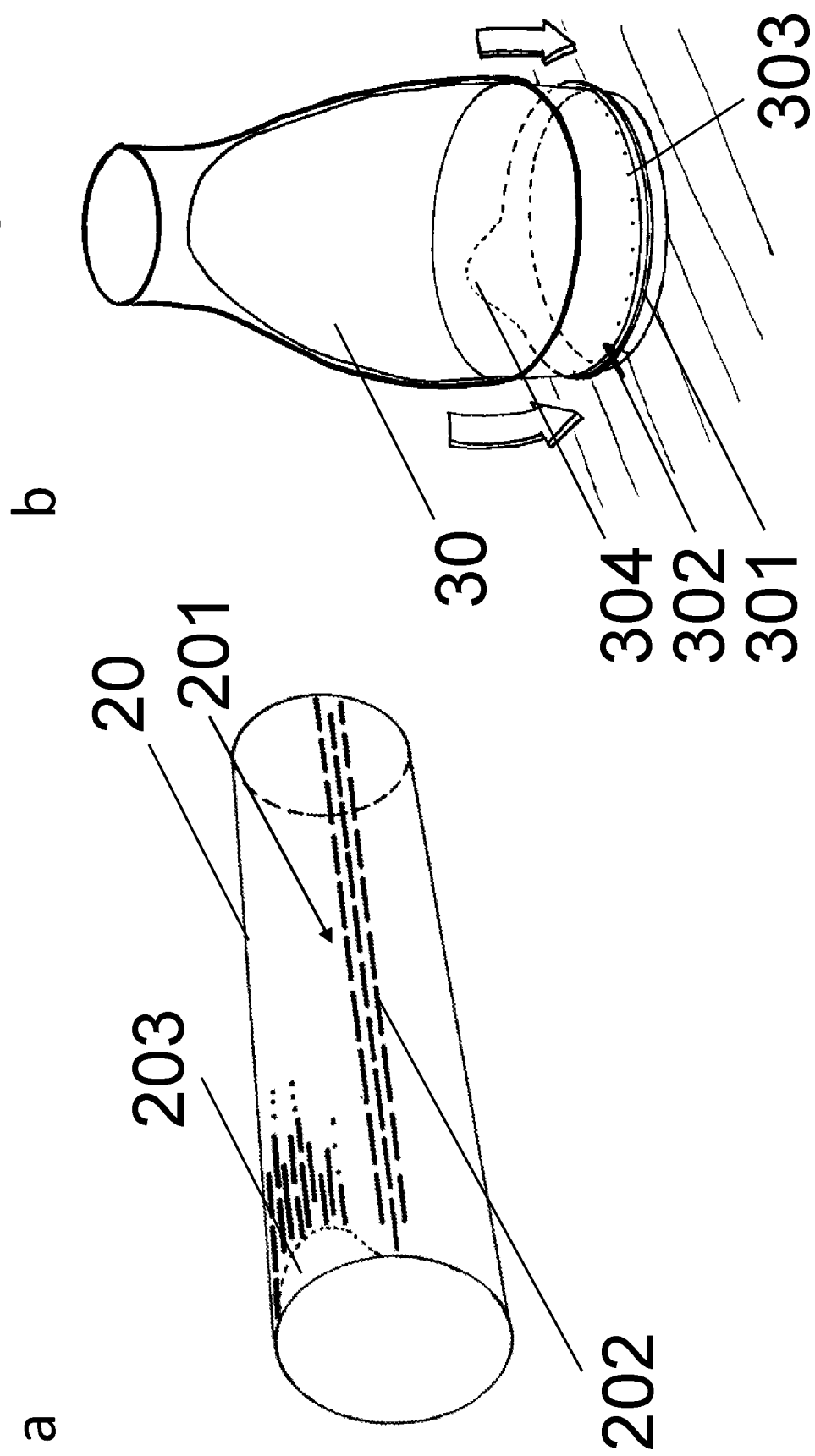
FIG. 9 shows a slotted tube with the pattern indicated and the process for fitting the slotted tube onto a mandrel.

FIGS. 9a and b show a slotted tube (20) with the pattern (201) indicated and the process of pulling a slotted tube (20) onto a mandrel (30) which may be derived from a three-dimensional copy of a heart. The process is intended to produce a patient-specific geometry of the frame structure which may be made out of an initially continuous, tubular semi-finished product.

FIG. 9a shows by way of indication a number of rows of cuts (202) orientated in the longitudinal direction of the tube, it being possible for neighbouring rows to be offset with respect to one another. The offsetting may influence the shape of the cells which are produced when the slotted tube is widened. Moreover, a corresponding pattern (201) may already provide the recess (203) which, after widening of the tube, leads to a notch being created along the circumference which prevents the spatial impairment of the vena cava or other relatively large anatomical structures. A suitable pattern (201) may also already determine the shape and length of the extension struts.

FIG. 9b shows a partially removed slotted tube (20) and an embodiment of the shaping mandrel (30). The mandrel (30) comprises a circumferential rib (301) in the proximity of its base and a circumferential rim made out of bores for the insertion of fixing bolts (302). The circumferential rib (301) may correspond to the extensive shape of the implant sought. One embodiment may, for example, take account of the recess (304) for the vena cava or other relatively large anatomical structures with the aid of the course of the circumferential rib (301). The rib (301) may be used here to set the circumferential shape of the implant precisely. In the state in which the tube (20) has been pulled over the mandrel (30) until it stops at the rib (301), the tube (20) may be affixed, with the aid of fixing bolts (302), which are inserted into the bores (303) provided for that purpose through the openings produced as a result of the slotting of the tube, until the widened form has become established in the precursor of the frame structure. If the slotted tube (20), for example, consists of a shape memory alloy, the establishment of the widened geometry may be carried out through normalization. Metallic frame structures which do not consist of shape memory alloys are also conceivable.

Figure 10:
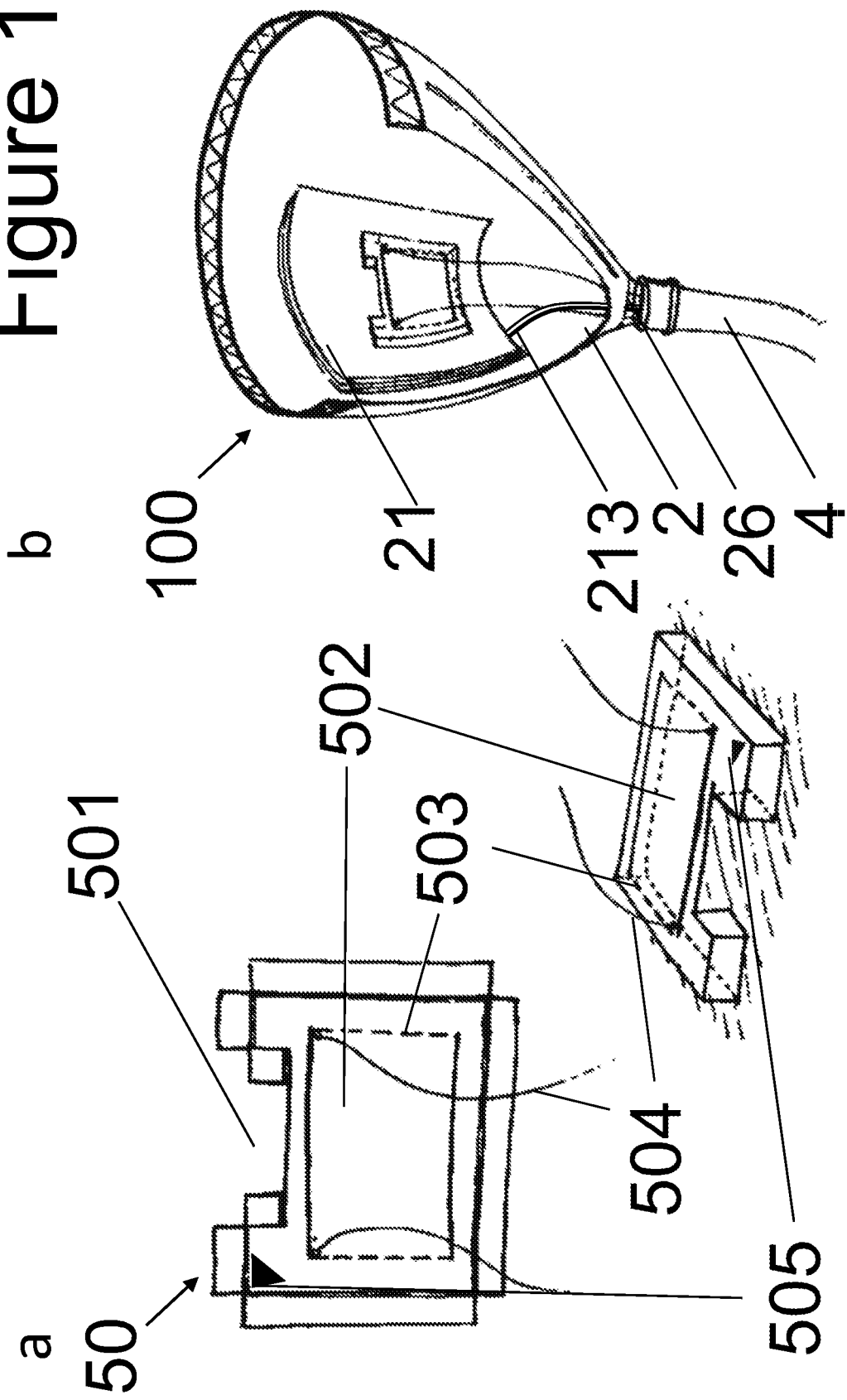
FIG. 10 shows an embodiment of an implant in which a substance carrier in the form of a pocket is mounted on a pneumatic chamber on the inside of a sleeve.

FIGS. 10a and b show an embodiment of a pocket (50) which may accommodate a substance carrier. The pocket (50) may be filled with a substance via an opening (501) in the lateral surface facing the upper edge of the sleeve (2). The pocket (50) may have a removable area (502) on the surface facing the heart. Removal thereof results in the temporally and spatially well-defined release of the substance.

FIG. 10a shows the unassembled pocket (50) which may accommodate a substance carrier and a three-dimensional depiction of the pocket (50). The pocket (50) may be affixed in the sleeve (2). Embodiments of a substance carrier are described in more detail in a subsequent section. If the device in an embodiment also has an expandable unit (21) which may be incorporated into the sleeve (2), the at least one pocket (50) may be affixed to the end face of an expandable unit (21). However, the pocket (50) may also be affixed somewhere in the sleeve (2) where there is no expandable unit (21). The present embodiment is designed such that the end face of the expandable unit (21) or the sleeve (2) forms the back of the at least one pocket (50). Alternatively, the pocket (50) may also have an enclosed space before coupling to the sleeve (2) and/or at least one expandable unit (21). In this case, a separate coupling mechanism may be required. The coupling mechanism may be designed such that coupling may also be carried out only under operating conditions and by a person in the operating theatre.

The width, length and depth of a pocket (50) or of a substance carrier are in each case defined as the dimensions of the pocket (50) or of the substance carrier in the circumferential direction of the heart, the longitudinal axis of the heart and in a radial direction perpendicularly to the longitudinal axis of the heart. The at least one pocket (50) may be between 10 mm and 80 mm wide, preferably between 20 mm and 50 mm. The length of a pocket (50) may be between 10 mm and 80 mm, preferably between 20 mm and 50 mm. The pocket (50) may be between 0.05 mm and 8 mm deep. The at least one pocket (50) may be between 1 mm and 3 mm deep. The material of the at least one pocket (50) may be identical to the material of the sleeve (2) or the material of the at least one expandable unit (21). The material of the at least one pocket (50) may also differ from the material of the sleeve (2) or the material of the at least one expandable unit (21). The material of the at least one pocket (50) may be a polymer. The material of the at least one pocket (50) may be polyurethane, silicone or polytetrafluoroethylene (PTFE). The pocket (50) may be made out of the same material as the sleeve (2) and/or an expandable unit (21). The pocket (50) may be incorporated directly into a sleeve (2) and/or an expandable unit (21), whereby the pocket (50) is part of the sleeve (2) or of an expandable unit (21).

The pocket (50) may, for example, first be cut as a two-dimensional unassembled part from a sheet made out of at least one of the materials specified above and then joined together to produce its three-dimensional form.

The at least one pocket (50) may have an opening (501) on one surface which may be used to insert a substance into the pocket (50) in the present embodiment. The at least one pocket (50) may have a removable area (502) on the surface facing the heart. The removable area (502) may be rectangular. The removable area (502) may be of round, elliptical or polygonal shape or a combination thereof. The removable area (502) may, in its implanted state, be removable from the pocket (50) from outside the body by means of a mechanism which uses traction elements (504). The mechanism and its fraction elements (504) may at least partially consist, for example, of threads, cords, rods, strips (for example of plastic) or similar loadable components. If this area (502) is pulled away, an opening is made in the at least one pocket (50) through which the substance held inside the at least one pocket (50) can come out, that is to say into the sleeve (2), and enter into contact with the heart at the location intended for release of the substance. The removable area (502) of the at least one pocket (50) may be pulled away through threads mounted in this area (502). The removable area (502) may have at least one perforation (503) of the material of the pocket (50) at its edges in order to be able to allow the process of pulling away. The removable area (502) may also have at least one dummy joint/predetermined tear point (503) at its edges which may allow the process of pulling away. The removable area (502) may serve to ensure the temporally delayed release of a substance inside the pericardial cavity. The pocket (50) per se may serve to protect the substance, for example against friction or during compression over the course of the implantation process. After implantation, this protection is no longer required and may therefore be removed.

Alternatively to the removable area (502) on the side of a pocket (50) facing the heart, an area (502) may be provided which is at least partially made out of a biodegradable and/or permeable material. This has the advantage that a substance is mechanically protected during the implantation process and may subsequently be released. Unlike with the removable area (502), no part therefore has to be removed from the body any longer, which facilitates the implantation process. The release of the substance may also be carried out in a time-controlled manner by using materials with a different dissolution and/or decomposition rate, with a defined wall thickness or with a specific permeability. Examples of such decomposable or soluble materials are natural polymers such as collagen or alginate, polysaccharides such as hyaluronic acid and gelatine and/or synthetic aliphatic poly (hydroxycarboxylic acid) polyesters such as poly($\epsilon$-caprolactone), polylactide, polyglycolic acid, poly(4-hydroxybutyric acid), poly(3-hydroxybutyric acid), poly(2-hydroxybutyric acid) or their copolymers and/or self-assembling peptides such as peptides based on arginine-glycine-aspartate amino acids. Examples of permeable substances are methylcellulose, polyurethanes or their copolymers, the porosity depending on the method of production. The at least one pocket (50) may also consist entirely of a biodegradable and/or a permeable polymer.

The pocket (50) may also comprise a radiopaque marking (505).

FIG. 10b shows an embodiment of the implant (100) which is partially cut away to provide a view of the inside of the sleeve (2). A pocket (50), which may accommodate a substance carrier, is affixed to the present expandable unit (21). The removable area (502) on the end face of the pocket (50) in the form of a rectangle is connected to the two upper corners with threads which are guided through the opening (26) of the sleeve (2) lying underneath through the encased cable harness (4) to the outside, that is to say out of the body.

Figure 11:
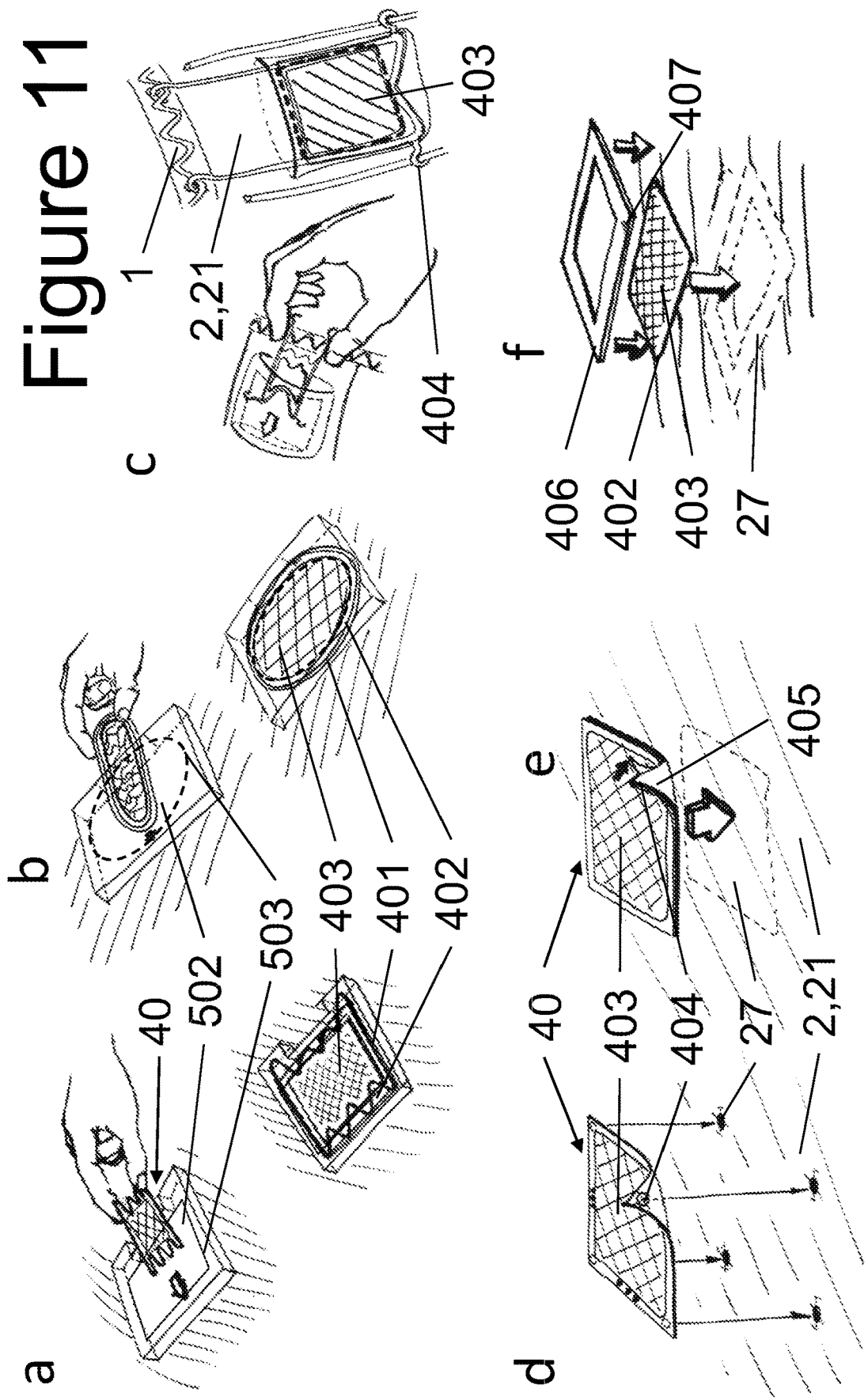
FIG. 11 shows various possible embodiments of the substance carrier.

FIG. 11 shows various embodiments of the substance carrier (40).

FIG. 11a shows the production and insertion of a substance carrier (40) into a pocket (50) which may be provided for the purpose of accommodating a substance carrier (40) during the insertion of the substance carrier (40) into the pocket (50) and in the installed state. A substance (403) which may have a therapeutic effect may be applied to the substance carrier (40). The at least one substance (403) may be applied to the substance carrier (40), for example by application, spreading, gluing, vapour deposition, populating with cells, casting or thermobonding.

In FIG. 11a, the substance carrier (40) is represented as being multi-part, consisting of a frame (401) and a membrane (402) which is stretched through the frame (401) and on which at least one substance (403) may be applied. The membrane (402) may be connected to the frame (401), for example by sticking. The frame (401) may also be incorporated into the membrane (402), for example moulded. The frame (401) may serve to facilitate the process of inserting the substance carrier (40) into the at least one pocket (50). The pocket may have a removable area (502) which may have a perforation (503). The frame (401) and the substance carrier (40) may be compressed for the purposes of insertion into a pocket (50). In the non-compressed state, the frame (401) may guarantee the correct positioning of the substance carrier (40) and the substance (403) applied thereto. The frame (401) may be dimensioned such that it may be inserted in its compressed state into the pocket (50) through an opening in the pocket (50) and is wider than the opening in the non-compressed state. As a result, before implantation of the implant, simple insertion of the substance carrier (40) may be guaranteed and any dislocation of the substance carrier (40) after implantation of the implant may be prevented. The frame (401) of the substance carrier (40) may be made out of polyurethane (PU), silicone, polytetrafluoroethylene (PTFE), metal or a metal alloy, in particular a shape memory alloy, or a combination thereof. The at least one material may be a shape memory alloy. The membrane (402) may be made out of polyurethane, silicone or polytetrafluoroethylene (PTFE). The membrane (402) may also consist of the same material as the frame (401). If the membrane (402) and frame (401) consist of the same material, the substance carrier (40) may also be formed as one part. The frame (401) may then consist of an amassing of the material, for example from a thickening of the material at the edge of the substance carrier (40). Alternatively, a single-part substance carrier (40) may be characterized in that material has been removed from the membrane area or subsequently weakened, for example through application of radiation or chemicals.

The membrane (402) may be made out of a different material than the frame (401). The membrane (402) may have an incorporated frame (401). The frame (401) may be made out of a self-expanding material. The frame (401) may be made out of a shape memory alloy and/or out of a superelastic material so that the substance carrier (40) may be transferred from a non-compressed form into a compressed form for the purposes of insertion into a pocket (50). The frame (401) may be made out of nitinol. The substance carrier (40) may be considerably deformable. The substance carrier (40) may be deformable for the purposes of insertion into a pocket (50) such that its width in a compressed state is smaller than or the same as the size of an opening in a pocket (50). The at least one substance carrier (40) may be between 10 mm and 80 mm wide, preferably between 20 mm and 50 mm. The at least one substance carrier (40) may be between 10 mm and 80 mm long, preferably between 20 mm and 50 mm. The at least one substance carrier (40) may be between 0.5 mm and 5 mm thick, preferably between 1 mm and 3 mm. The frame (401) and/or the substance carrier

(40) may also differ from the flat shape and be three-dimensionally adapted to the curvature of a cylinder, a ball or a copy of a heart.

In the present embodiment, the substance carrier (40) may be inserted into the pocket (50) through an opening in the pocket (50). In the present figure, a substance carrier (40) is represented with a rectangular frame (401). The opening in the pocket (50) may be smaller than the lengths of the edges of the substance carrier (40) and/or of the frame (401). At least one edge of the frame (401) may be wavy, meandering, contorted or bent in form. The difference in the form of at least one edge of the frame (401) from the straight form may make the frame (401) easier to compress. In one embodiment in which at least part of the substance carrier (40) consists of an elastic and/or superelastic material, the substance carrier (40) may, after deformation on insertion into the pocket (50) through the opening in the pocket (50), return to its initial geometry before deformation again. As a result, a better seating of the substance carrier (40) in the pocket (50) may be achieved. The frame (401) of the substance carrier (40) may consist of at least one wire. The frame (401) of the substance carrier (40) may be produced by separating a profile from a previously continuous semi-finished product, for example by stamping from a sheet or laser cutting from a tube, a sheet or a film. Alternatively, the frame (401) may also be produced by a generative method of production, such as casting, sintering or a rapid prototyping method. The frame (401) may consist of a coherent profile. If the frame (401) consists of at least one wire, the ends of the at least one wire may be connected, for example by gluing, welding, riveting, hooks and/or eyelets or a sleeve, thereby producing an enclosed frame (401). The profile or a wire of the frame (401) may also not be connected in at least one place and an open and/or interrupted frame (401) is produced. An enclosed frame (401) has a greater structural stiffness and may also ensure a certain formal stability of the substance carrier (40) when forces are exerted through movement of the heart or when load is applied by an expandable unit, the sleeve (2) or another part of the implant. An open frame (401) has the advantage that the substance carrier (40) is easier to compress than a comparable substance carrier (40) with an enclosed frame (401). The wire winding or the profile may have a form at least partially differing from a straight line. The at least one wire or the profile of the frame (401) may have a periodically alternating directrix. The directrix may also be aperiodically alternating. If the material of the frame (401) is a shape memory alloy, the frame (401) may be transformed into a defined shape with the aid of at least one heat treatment.

FIG. 11b shows a further embodiment of the substance carrier (40) during insertion of the substance carrier (40) into the pocket (50) and in the implanted state. The pocket (50) shown corresponds here to that in FIG. 11a. The present embodiment of the substance carrier (40) is elliptical and comprises a membrane (402) which contains at least one wire incorporated into the membrane (402) for stretching the membrane (402). In the present embodiment, at least one of the two main axes may be longer than the edge, which is parallel to this main axis, of the pocket (50) which is rectangular in this embodiment, which means that the elliptical substance carrier (40) is better fixed in the rectangular pocket (50) through the resulting clamping effect. The pocket (50) may also differ from the rectangular shape. In this case, it may be advantageous also to change the shape of the substance carrier (40) and adapt it to the shape of the pocket. Advantages of the elliptical embodiment are, amongst other things, the simple geometry and the easy producibility of the substance carrier (40).

FIG. 11c shows a further embodiment of the substance carrier (40) and of the pocket (50) during insertion of the substance carrier (40) into the pocket (50) and in the implanted state. Materials which may be used for the substance carrier (40) and the pocket (50) are specified in a previous section. The embodiment of the substance carrier (40) shown is in two parts. It comprises a frame (401) and a membrane (402) to which the at least one substance (403) may be applied. The previous descriptions correspondingly apply to the substance carrier (40), the frame (401) and the membrane (402). FIG. 11c also shows a possible way of connecting the substance carrier (40) to the frame structure (1), the sleeve (2), the end face of the at least one expandable unit (21) and/or the pocket (50). For that purpose, the substance carrier (40) may have at least one coupling element (404). The at least one coupling element (404) may be part of the frame (401), for example a longitudinal strut or a wire element, and protrude from the frame (401). The coupling element (404) may be designed at the end such that coupling to another component of the device is made possible. The coupling element (404) may extend as far as a structurally bearing component of the frame structure (1) or as far as another coupling element (404) of the sleeve (2), of the pocket (50) and/or of an expandable unit (21). FIG. 11c shows four coupling elements, two of the coupling elements protruding laterally away from the frame (401) of the substance carrier (40) and connecting the latter by means of hooks to two wires or struts of the frame structure (1). The other two coupling elements in FIG. 11c protrude upwards away from the frame (401) and connect the latter to the implant through an opening in the sleeve (2) and on the "upper rim" of the frame structure (1). The coupling may be carried out by means of positive locking, non-positive locking and/or material bonding. In the case of positive coupling, the at least one coupling option may include a loop, a hook, an eyelet, a button or at least one Velcro fastening and/or zip. In the case of non-positive coupling, an adhesive connection or a connection by tying with threads, lamellae or cables may be used. In the case of materially bonded coupling, the connection may be a welded connection or an adhesive connection. In the present embodiment, the coupling is represented with four coupling elements. A substance carrier (40) may also have one, two, three, four, five, six or more coupling elements.

The pocket (50) in the present embodiment may have two openings at opposite ends. The substance carrier (40) may be inserted into the pocket (50) through the first opening and exit again through the second opening. The pocket (50) may have a removable area (502) on the end face which may be delimited by a perforation (503) and/or a dummy joint. After insertion and fixing of the substance carrier (40) to the sleeve (2) and/or to the end face of the at least one expandable unit (21) and/or the frame structure (1), the removable area (502) may be removed. Alternatively, the removable area (502) is made, as described above, at least partially out of a biodegradable and/or permeable material. The removable area (502) may be formed according to the description in FIG. 10. Following the removal of the removable area (502), the substance (403) which is located on the substance carrier (40) may be brought directly into contact with the surface of the heart. The pocket (50) may have the function of protecting the substance carrier (40) in the non-expanded state of the implant. The pocket (50) may increase the positional accuracy of the substance carrier (40). An advantage of the embodiment shown in FIG. 11c is the additional fixing of the substance carrier (40) in the frame structure (1) with simultaneous protection of the substance carrier (40) through the pocket (50) which is shown here in the form of a protective sleeve.

FIG. 11*d* shows a further embodiment of a substance carrier (40) consisting of a membrane (402) which may be directly connected to the inside of the sleeve (2) and/or to the end face of the at least one expandable unit (21). In this embodiment, a pocket (50) and/or a frame (401) may be dispensed with. The connection between the substance carrier (40) and the surface of the sleeve (2) and/or the end face of the at least one expandable unit (21) may be carried out in the ways mentioned in a previous section of the description. In particular, the at least one coupling (27, 404) may be designed as a plug connection or as an adhesive connection. The at least one coupling (27, 404) may also be carried out through at least one button-eyelet connection or at least one Velcro fastening connection. In the present embodiment, the substance carrier (40) may have four selective coupling options. The coupling option (27, 404) may also be designed as a planar coupling. The coupling (27, 404) to the surface of the sleeve (2) and/or to the end face of the at least one expandable unit (21) may require at least one coupling pair (27, 404), it being possible for one coupling partner to be affixed to the substance carrier (40) and the other coupling partner to be fixed to the surface of the sleeve (2) or the end face of the at least one expandable unit (21). The application of the substance (403) to the substance carrier (40) may correspond to a previous description. Advantages of such an embodiment are the simplified mounting of the substance carrier (40) in the sleeve (2) or on an expandable unit (21) and the fact that a pocket (50) is not additionally required in order to keep the substance carrier (40) in position.

FIG. 11*e* shows a further embodiment of the substance carrier (40). It is similar to the embodiment which is described in FIG. 11*d*. The substance carrier (40) may consist of only one membrane (402) to which a substance (403) may be applied and may contain no frame (401). The coupling (27, 404) between the underside of the substance carrier (40) and the inside of the sleeve (2) and/or the end side of an expandable unit (21) is designed to be planar in this embodiment. The at least one planar coupling option (404) may at least partially cover the underside of the substance carrier (40). The underside of the substance carrier (40) may also have two, three, four, five, six or more planar coupling elements (404) which in each case at least partially cover the underside. The underside of the substance carrier (40) may have one, two, three, four, five, six, seven or more planar coupling elements (404).

The coupling partner of the at least one planar coupling element (404) may be the surface of the sleeve (2) and/or the end face of the at least one expandable unit (21). The surface of the sleeve (2) and/or the end face of the at least one expandable unit (21) may also have at least one coupling element (404) which serves as a coupling partner for the at least one coupling element (404) on the underside of the substance carrier (40). The at least one planar coupling element (404) on the underside of the substance carrier (40) may have at least one planar cover (405) which may be removed in order to release the at least one planar coupling element (404) on the underside of the substance carrier (40). The complementary coupling area (27) is located on the sleeve (2) and/or the at least one expandable unit (21).

Alternatively, the planar cover (405) may also remain on the substance carrier (40) if it itself allows an adhesive connection and also has at least one additional function. For example, this additional layer (405) may be at least partially electrically conductive, raising the possibility of applying a potential to the substance carrier (40) or the substance (403). This may influence the growth of, for example, stem cell cultures. In the present embodiment, the cover (405) of the at least one planar coupling element may be removed. The substance carrier (40) in the present embodiment may be mounted and affixed directly onto the surface of the sleeve (2) and/or the end face of the at least one expandable unit (21). The advantages of the present embodiment correspond to those listed in FIG. 11*d*. The planar coupling (27, 404) also allows potentially better retention than in the embodiment in FIG. 11*d*. It may also be placed anywhere because no pocket (50) is provided.

FIG. 11*f* shows a further embodiment in which the substance carrier (40) consists of at least two parts. One part may be a membrane (402) to which a substance (403) may be applied. The substance carrier (40) may also consist of at least one fixing component (406). The further at least one fixing component (406) of the substance carrier (40) may serve to position and fix the membrane (402) on the inside of the sleeve (2) and/or the end face of the at least one expandable unit (21). In the embodiment shown, the at least one fixing component (406) is provided as a flat, frame-like component. The at least one fixing component (406) may be formed like a frame (401) according to the previous description, with the special feature that the membrane (402) to which the substance (403) is applied and the frame (401) are connected to one another only on insertion into the sleeve (2)/onto the expandable unit (21). The underside of the at least one fixing component (406) may at least partially overlap with the top of the membrane (402). As a result of this at least partial overlapping, the membrane (402) may be affixed to the surface of the sleeve (2) and/or the end face of the at least one expandable unit (21). The underside of the at least one fixing component (406) may be connected to the inside of the sleeve (2) and/or the end face of the at least one expandable unit (21) by means of at least one coupling (27, 406). The at least one coupling (27, 406) may be designed as a plug connection or as an adhesive connection. The at least one adhesive connection (27, 406) may be produced in the form of a self-adhesive film which may be connected to the surface of the sleeve (2) and/or the end face of the at least one expandable unit (21). The self-adhesive film may consist of a base layer, an adhesive layer and a protective film which protects the adhesive layer for example from contact with water. The base layer may consist of polyurethane, silicone or polytetrafluoroethylene (PTFE). A silane layer may possibly be used as a single-component adhesive layer in a self-adhesive film. Other kinds of adhesive connection are also conceivable. The hardening takes place after removal of the removable protective layer in moist surroundings through water. The at least one coupling may also be carried out through at least one button-eyelet connection or at least one Velcro fastening connection.

In respect of each of the abovementioned embodiments, the substance carrier (40) may be provided with the substance (403) only directly before implantation of the implant under operating conditions by a person in the operating theatre, and may then be inserted into the device, for example into a pocket (50), onto the inside of a sleeve (2) and/or onto the end side of an expandable unit (21). Alternatively, a substance carrier (40) already provided with a substance (403) may be used and the latter may be inserted into the device under operating conditions. Alternatively, the substance carrier (40) may be inserted into a pocket (50), into the sleeve (2) and/or onto the end side of an expandable unit (21) right during production of the device and may be provided with a substance (403) during production of the device or at a later time, for example before implantation of the device. Irrespective of the degree of preparation of the substance carrier (40)/of the device, pretreatment of the substance carrier (40) and/or of the substance (403) may be required before implantation of the device. Pretreatment of the substance (403) and/or of the substance carrier (40) may involve flushing with a buffer (for example Phosphate Buffered Saline, PBS) to set a specific pH value, flushing with a nutrient solution, setting a temperature or a combination thereof. Alternatively, a device with a substance carrier (40) on which no substance (403) is yet provided may also be implanted. The substance (403) may then be added after implantation has been carried out. Details of this are provided in a subsequent section. An advantage of this embodiment is the division of functions into a pure substance carrier (40) and a fastening frame (406), which may make production of the individual parts less complex and also simplify handling upon use.

A further embodiment of the substance carrier (40) may be porous. The substance carrier (40) may therefore store the substance (403) within it like a sponge and release it, for example, when pressure is applied. Through the enlarged surface area and through the use of biocompatible materials or a biocompatible coating, the substance carrier (40) in such an embodiment may also be provided with living cells which may transfer from it to the surface of the heart, for example if it is in permanent contact with the latter.

The substance carrier (40) may comprise at least one sensor and/or at least one electrode. The sensor here may be a temperature sensor, a pressure sensor, a pH sensor, an oxygen sensor, a $CO_2$ sensor, an optical sensor, a conductivity sensor or an impedance sensor. Possible functions of the sensors are mentioned in a previous section. With the aid of a sensor, the conditions on and around the substance carrier (40) may be detected in order, for example, to indicate whether contact is being made with the surface of the heart.

The substance carrier (40) may also comprise at least one radiopaque marking (407) by means of which the position of the substance carrier (40) during and after implantation may be checked. Alternatively, or in addition, the pocket (50) may comprise a radiopaque marking (505).

Figure 12:
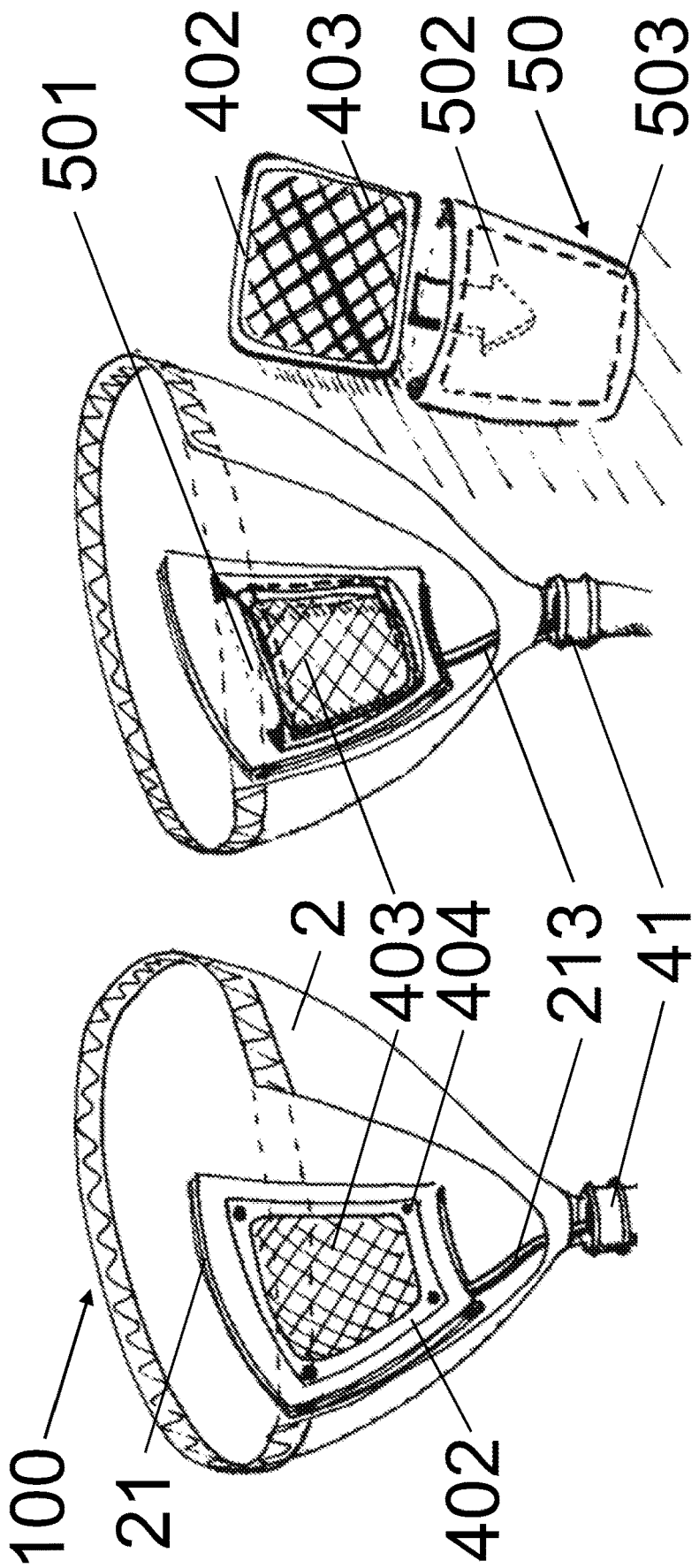
FIG. 12 shows two general views of embodiments in which the substance carrier is coupled directly to the pneumatic chamber.

FIGS. 12*a* and *b* show two embodiments of the implant (100). A partial section through the sleeve (2) provides a better view of the substance carrier (40) which is affixed to the at least one expandable unit (21). The at least one expandable unit (21) may be provided with a delivery and discharge line (213).

FIG. 12*a* shows an embodiment of the implant (100) in which the substance carrier (40) without a pocket (50) may be affixed directly onto the end face of the at least one expandable unit (21). The fixing may be carried out with the aid of in this case punctiform couplings (27, 404). The punctiform couplings (27, 404) may be plug connections, button-eyelet connections or adhesive connections, or alternatively Velcro fastening connections. The substance carrier (40) may consist of a membrane (402) and comprise a substance (403) applied thereto. Alternatively, the substance carrier (40) may have a frame (401) over which a membrane (402) is stretched, onto which in turn the substance (403) may be applied. Embodiments of a substance carrier (40) differing herefrom are also conceivable.

FIG. 12*b* shows an embodiment of the implant (100) in which the substance carrier (40) may be inserted via an opening (501) into a pocket (50) and affixed directly onto the end face of the at least one expandable unit (21). The pocket (50) may have a removable area (502) which may provide a window in the pocket (50) after it has been removed. The removable area (502) may be defined by a perforation (503) which may facilitate the removal of the removable area (502). As a result, the substance applied to the substance carrier (40) may be brought into contact with the surface of the heart through the window. The coupling of the substance carrier (40) to the surface of the at least one expandable unit (21) may be carried out via a planar coupling option (27, 404), for example a planar adhesive connection to the underside of the substance carrier (40) which at least partially covers the underside of the substance carrier (40). In the embodiment shown, the at least one expandable unit (21) is structured as an inflatable chamber. This may be an inflatable chamber which is filled with a fluid. Liquids or gases may be used as fluids. Alternatively, the inflatable chamber may also be filled with solids (for example nanoparticle mixtures). Alternatively, the inflatable chamber may also be filled with liquids and/or gases and/or solids. The present embodiment of the implant (100) has an inflatable unit which may be filled with a gas mixture (air) and which is supplied with a gas mixture via a pneumatic line (213). The pneumatic line (213) may be passed through the fixing sleeve (41) and the cable harness (4) here.

Figure 13:
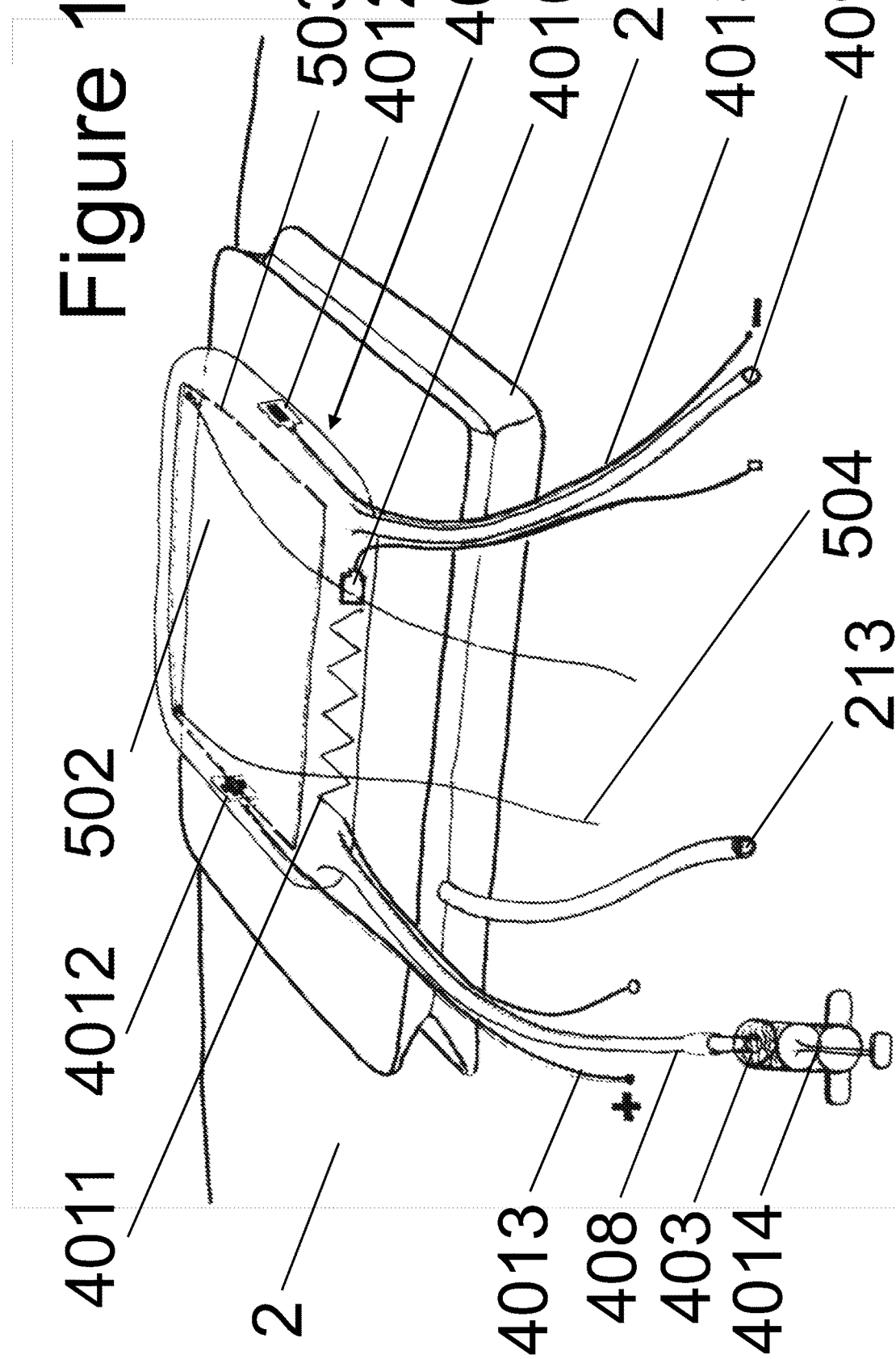
FIG. 13 shows a substance carrier in the form of a fillable and emptyable pouch mounted on the front of a pneumatic chamber.

FIG. 13 shows an embodiment of the at least one substance carrier (40) of the implant in the form of a container (40), a substance delivery line (408), a substance discharge line (409), a sensor (4010) and an adjuster (4011).

The material of the substance carrier (40) may be the same as that of the at least one expandable unit (21). A different material therefrom may also be chosen. Possible materials are specified elsewhere. For the purposes of delivering, replacing and/or refilling substance (403) into the device in the implanted state, the device may also contain at least one substance delivery line (408). In order to discharge old, used or therapeutically no longer active substance (403) from the implanted device or else for the purposes of flushing the substance carrier (40) and/or the membrane, the device may also contain at least one substance discharge line (409). The at least one substance delivery line (408) and/or substance discharge line (409) may in each case end outside the body. In this embodiment, the substance carrier (40) may, after implantation, be filled from outside the body with the substance (403) itself or with a liquid which contains the at least one substance (403). In the exemplary embodiment shown, the substance carrier (40) may be filled via a manual delivery device (4014), for example a syringe, which contains the substance (403). Machine-controlled delivery is also conceivable. The substance carrier (40) may have at least one discharge line (409) via which a liquid may be removed from inside the substance carrier (40). The substance carrier (40) may be emptied from outside the body. The possibility of at least partially filling and emptying from outside the body may serve to set the quantity of the at least one substance (403), to set the concentration in the event that the substance (403) is an active agent, or to replace the liquid containing the substance (403). The at least one substance carrier (40) may also only have a shared substance delivery and discharge line. The at least one substance delivery line (408) and/or the at least one substance discharge line (409) may also be fed out of the body in the cable harness. The plug parts on the cable harness may contain ports for the connection of substance lines and the substance lines may be connected to these ports. The plug parts may be connected to a supply unit. The delivery or discharge of substance (403) from a substance carrier (40) may also be regulated through the supply unit. The supply unit may correspondingly contain, for this purpose, a substance reservoir, a feed pump and/or a pressure reservoir, valves and electric components for controlling the components, for example a microcontroller.

The substance carrier (40) may have a removable area (502) on its end face which may be removed and which may provide a window into the inside of the substance carrier (40). Through the window, the contents of the substance carrier (40) may come into contact with the surface of the heart or the inside of the pericardial cavity. The removable area (502) of the substance carrier (40) may be removed from the substance carrier (40) via a device provided for that purpose from a locationally remote point. This point may lie outside the body. A mechanism may lead to the removal of the removable area on the substance carrier (40).

In FIG. 13, this mechanism is designed with the aid of cords (504). Exemplary embodiments may comprise at least one cord provided to remove the removable area, a thread or a cable, for example as part of a cable control. Alternative mechanisms are also conceivable. In the present exemplary embodiment, two cords (504) are connected to those corners of the removable area (502) lying at the top. The removable area of the substance carrier (40) may be removed by pulling on the cords (504). The cords (504) may be designed as part of the cable harness and may be pulled from outside the body. The position of the removable area after removal from the substance carrier (40) may be in a cavity in the fixing sleeve lying inside the epicardium. Alternatively, the removable area (502) is made, as described above, at least partially out of a biodegradable and/or permeable material. Further characteristics of the removable area are described in previous sections.

The substance carrier (40) may also be designed as at least one fillable and/or emptyable container for storing substance (403). The at least one container may alternatively also be coupled directly to a substance carrier (40) so that substance (403) may transfer from the container (40) onto the membrane. For example, a container (40) may be located directly on the back of a substance carrier (40) and the coupling point may be arranged to be permeable or perforated. If the container (40) is not in direct contact with a substance carrier (40), a substance-conducting connection from the container (40) to the membrane may also be produced through a channel or hose. The container (40) may have at least one delivery line (408) through which a substance (403) or a fluid which contains the at least one substance (403) to be inserted may be delivered into the container (40). The container (40) may also have a discharge line (409) via which substance (403) may be removed from the container (40) out of the body.

The substance carrier (40) may also comprise at least one sensor (4010). The at least one sensor (4010) may detect a parameter of the substance carrier (40) and/or of the content of the substance carrier (40). Variables detectable through the at least one sensor (4010) may be the compressive or tensile stress in the substance carrier (40), the pH value, the temperature, an electric voltage, the osmolarity, the oxygen concentration, the $CO_2$ concentration, the electrical conductivity, the optical density, an active agent concentration, the presence of liquid and/or substance (403) or a combination thereof. The position of the at least one sensor (4010) on the substance carrier (40) may be such here that it enables optimal detection of the parameter of the substance carrier (40) and/or of the substance (403) contained therein to be detected.

The substance carrier (40) may also comprise at least one adjuster (4011) to influence at least one parameter of the substance carrier (40) and/or of the substance (403). In the present exemplary embodiment, a heating coil (4011) is shown by way of example. The at least one heating coil (4011) may be used to adjust the temperature in the substance (403) or on the substance carrier (40). It is possible hereby to influence, for example, the growth conditions for living biological cells.

The substance carrier (40) may comprise at least two electrodes (4012) which may be connected to a supply unit via electric lines (4013). The two electrodes (4012) may be an adjuster (4011). Via the electrodes (4012), an electrical voltage may be applied to the substance carrier (40), the membrane and/or the liquid located in the substance carrier (40) which contains the substance (403). The application of an electrical voltage may change the characteristics of the substance (403) located in the substance carrier (40). The application of an electrical voltage may influence the growth of living biological cells located in the substance carrier (40).

In FIG. 13, the substance carrier (40) is affixed to the end side of an expandable unit (21). With the aid of the expandable unit (21), contact may be made between the substance carrier (40) or its contents and the surface of the heart by filling and emptying the expandable unit (21). With the aid of the at least one expandable unit (21) to which the substance carrier (40) is affixed, the contact pressure of the substance carrier (40) against the surface of the heart may be set by delivering and discharging a fluid via the pneumatic line (213). With the aid of the at least one expandable unit (21) to which the substance carrier (40) is affixed, the contact pressure of the substance carrier (40) against the surface of the heart may be adjusted as required. If the expandable unit (21) is, for example, structured as an inflatable chamber, the contact pressure against the surface of the heart may be regulated by delivering or discharging a pressurized fluid via the line (213). The filling with fluid or the discharging of the fluid may be regulated so that constant contact pressure of the substance carrier (40) against the heart muscle always prevails. Alternatively, temporally and periodically alternating pressure patterns may also be applied. For example, a lower contact pressure may be applied during the systole than during the diastole or correspondingly conversely. This has the advantage that the behaviour of the body's own cells and of the therapeutic (stem) cells may be influenced as a function of the contact pressure and therapeutic efficiency may therefore be improved.

FIGS. 14*a* to *d* show various embodiments of a substance carrier (40) which may be exposed to a mechanical load. A mechanical load on the substance carrier (40) may lead to a mechanical load on the membrane (402) and the substrate located thereon. If the substrate contains living cells, different what are referred to as cytokines may be secreted if cell physiology is influenced owing to the mechanical load. Depending on the cytokines secreted from the cells, it may be possible, for example, to regulate therapeutic efficiency in order to regenerate ischaemic myocardium tissue after a myocardial infarction.

Figure 14:
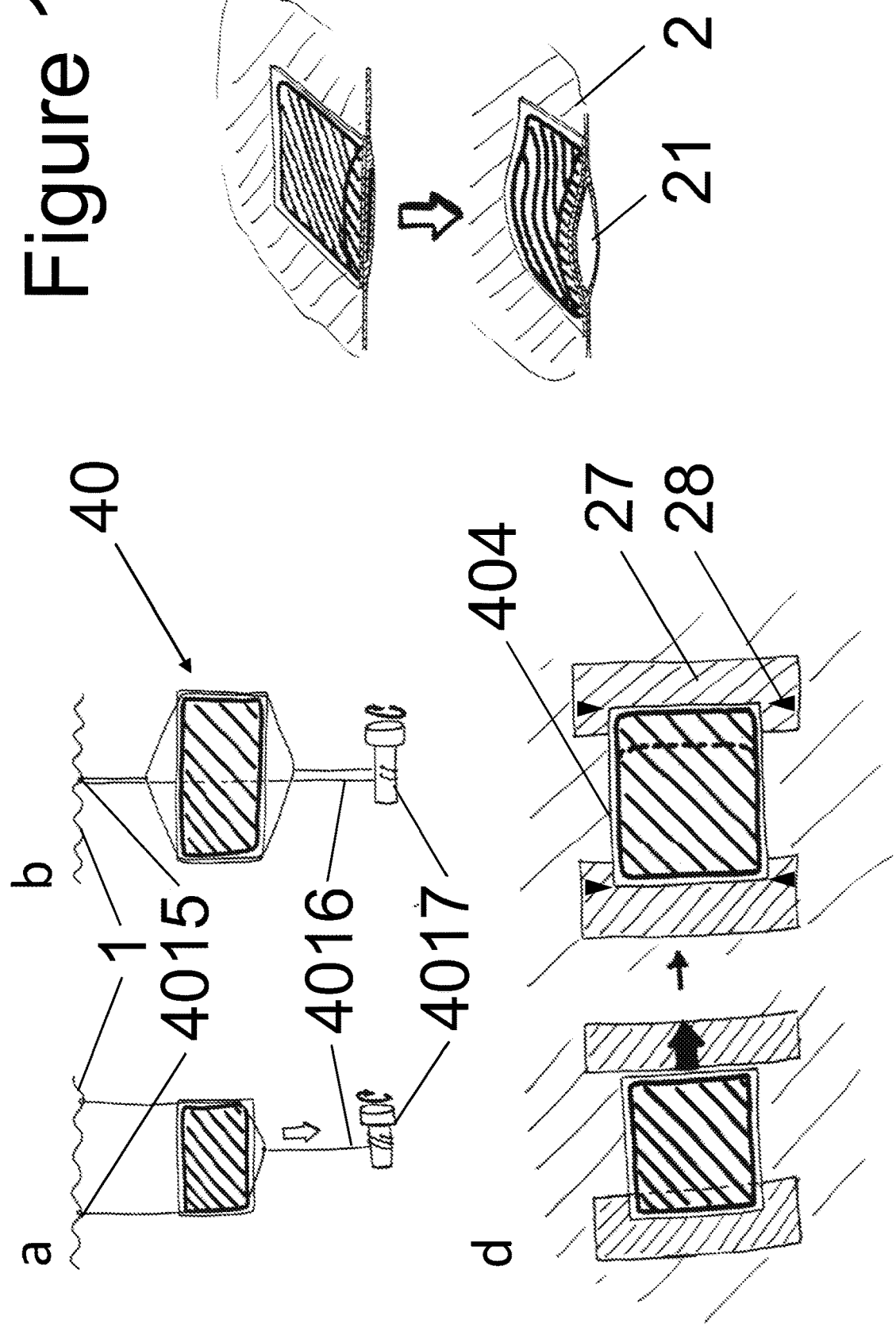
FIG. 14 shows various embodiments which serve to generate a tension in the substance carrier.

FIGS. 14*a* and *b* show exemplary embodiments in which the tensile stress of the substance carrier (40) may be set via a mechanical adjustment mechanism (4017) in the form of coupling elements (4015), a traction element (4016) and a winder (4017). The substance carrier (40) may be coupled to the frame structure (1). This coupling may be produced in this exemplary embodiment through coupling elements, for example through at least one strut, a thread, a cable or at least one wire. The at least one coupling element is affixed to a substance carrier (40) and may be coupled at the end thereof to the frame structure (1), in particular to a frame segment running along the circumference. A traction element (4016), for example a wire, a thread or a plastic strip, may also be affixed to the substance carrier (40), the other end of which traction element (4016) is coupled to a winder. Via the winder, the state of axial stress of the substance carrier (40) may be set. Through setting of the state of axial stress, the growth of living biological cells located on the substance carrier (40) and the physiology of the living biological cells may be influenced. Via the winder, a tensile stress may be applied to one end of the substance carrier (40). Depending on the embodiment of the cable control, a tensile stress may also be applied via the winder to both ends of the substance carrier (40). The tensile stress may be constant. The tensile stress may also be transient in order, for example, to produce a pulsatile stress similar to a physiological stress.

FIG. 14c shows a further embodiment of a device for setting the mechanical load on the substance carrier (40) with the aid of an expandable unit (21). The substance carrier (40) may be mounted via an expandable unit (21) which may be incorporated into the sleeve (2). In the present exemplary embodiment, the expandable unit (21) for adjusting the mechanical load is represented as an inflatable chamber. An expandable unit (21) may press the substance carrier (40) against the surface of the heart. The substance carrier (40) may also be larger than an expandable unit, whereby the expandable unit (21) may be at least partially covered by the substance carrier (40). In this case, an expansion of the expandable unit leads to an elongation of the substance carrier (40) and/or the substance carrier (40) and the substance (403) located thereon, as a result of which mechanical load may be built up. The amount of the elongation and/or stress produced may be regulated via the stroke of the expansion of the expandable unit (21).

FIG. 14d shows an exemplary embodiment of a substance carrier (40) which may be exposed to a mechanical load. The substance carrier (40) may be affixed prestressed to the sleeve (2) and/or the end face of the at least one expandable unit (21). The substance carrier (40) may have, on its underside, at least one planar coupling element with which a preferably materially bonded connection between the substance carrier (40) and the surface of the sleeve (2) and/or the at least one expandable unit (21) may be formed. The materially bonded connection may be an adhesive connection. The state of stress may be set in a targeted manner through at least one marking (28) applied to the surface of the sleeve (2) and/or the end face of the at least one expandable unit (21). This at least one marking (28) may indicate how far the substance carrier (40) has to be elongated in order to build up the stress to be set. The at least one marking (28) may indicate a distance. The at least one marking (28) may also copy the outlines of the elongated substance carrier (40) so that the elongation state to be set during fixing is assured. Alternatively, to fix the prestressed substance carrier (40), positive connection may also be used in order to produce the state of stress to be set. The positive connection may be a button-eyelet connection, a push-button connection, a Velcro fastening connection or a hook-eyelet connection between the coupling elements (27, 404). To facilitate elongation of the substance carrier (40), grips may be provided in the form of loops or wings on the substance carrier (40) which cannot undergo any coupling with the surface of the sleeve. It is therefore possible to pull on these grips without impairing the coupling surface or coupling points through contact with the skin.

Figure 15:
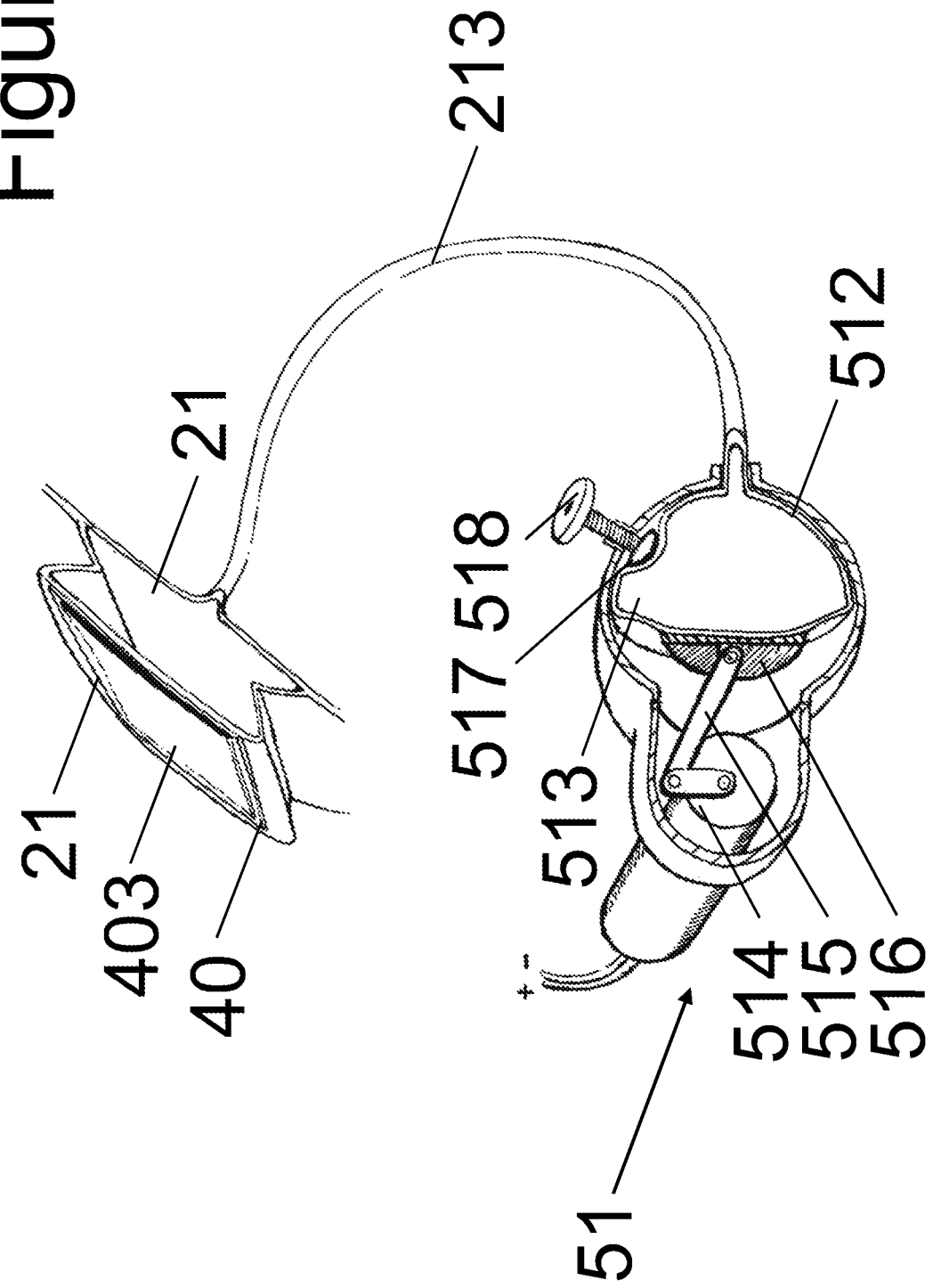
FIG. 15 shows embodiments of an actuator unit for changing the degree of expansion of an expandable unit of the implant.

FIG. 15 shows an embodiment of the at least one actuator unit (51) which may set the volume of the at least one expandable unit (21) via the pneumatic line (213). Embodiments of the device according to the invention may have at least one actuator unit (51). An embodiment of the actuator unit (51) is represented which may comprise a reservoir space (513) filled with a fluid and surrounded by a membrane (512) (this fluid may be a gas and/or a liquid), a drive unit (514) (which may be an electric motor or a pneumatic unit), a connecting rod (515) and a piston (516). The reservoir space (513) may be delimited by a membrane (512). This membrane (512) may be elastic. The membrane (512) may be made out of the same material as the at least one expandable unit (21). The membrane (512) may also be made out of a different material from the at least one expandable unit (21). The membrane (512) may be made out of polyurethane, silicone or polytetrafluoroethylene. The membrane (512) may be ellipsoid in shape. The membrane (512) may also be other than ellipsoid in shape. The piston (516) may be part of the membrane (512). The piston (516) may also be designed as a separate part. The reservoir space (513) is connected to the space of the at least one expandable unit (21) via a line. The reservoir space (513) may lie outside the body. The reservoir space (513) may also lie inside the body. The reservoir space (513) may be accommodated in the supply unit. The space of the at least one expandable unit (21) of the implant may be the chamber space (215) of an inflatable, bellows-like chamber. The reservoir space (513) may be larger than the chamber space (215). The overall space, consisting of the reservoir space (513), the chamber space (215) and the line space, is sealed and filled with a fluid. The fluid may be a gas and/or a liquid.

The piston (516) may reduce the reservoir space (513). The piston (516) may reduce the reservoir space (513) by pressing in the membrane (512). The piston (516) may press in or release the membrane (512) through a translational movement. The pressing in or the releasing of the membrane (512) by the piston (516) may also be achieved through a movement of the piston (516) differing from a translational movement. The pressing in or the releasing of the membrane (512) may be achieved through a combination of translational and rotatory movements. By changing the reservoir space (513), the chamber space (215) may be changed owing to the sealed nature of the overall space. As a result, the pressure exerted by the at least one expandable unit (21) on the surface of the heart may be set.

The piston (516) may be moved by means of a device provided for that purpose and made to press in or release the membrane (512) of the reservoir space (513). The device may be an eccentric disc. This device may also differ in shape from an eccentric disc. This device may be a crankshaft. The device may carry out a rotatory movement for the purposes of moving the piston (516). The device may also carry out a translational movement or a combination of translational and rotatory movements for the purposes of moving the piston (516). Through movement of the device, the piston (516) may be moved and this may change the reservoir space.

The device may also be identical to the piston (516). In such an embodiment, the device may be used to change the reservoir space (513).

An embodiment of the drive unit (514) of the at least one expandable unit (21) may comprise a device for moving the piston (516). This device for moving the piston (516) may be an eccentric disc which may be moved by means of a motor unit. This motor unit may be an electric motor. The motor unit may also be a pneumatic unit. The eccentric disc may be positioned on the drive shaft of the motor unit. The drive shaft of the motor unit may rotate axially. The control variable of the motor unit may be the speed of the shaft. The control variable of the motor unit may also be a translational stroke. The motor unit may change the reservoir space (513) through a translational stroke movement. The motor unit may set a temporally constant stroke. The motor unit may also set a temporally variable stroke.

One embodiment of the actuator unit (51) may also have a further option for setting (517) the reservoir space (513). This setting option (517) may be static. The setting option may be a stroke element. In the present embodiment, the stroke element (517) may be adjusted via a rotary button (518). The setting of the stroke element (517) may also be carried out via an operating element differing from a rotary button, for example by means of a slide control which may control the setting of the stroke element.

FIG. 15 shows an embodiment of the actuator unit (51) in which the eccentric disc is designed by means of a connecting rod (515) mounted eccentrically on the motor shaft. The position of the connecting rod (515) is set by means of a motor unit (514) which may be an electric motor. The end of the connecting rod (515) not mounted eccentrically on the motor shaft may be coupled to the membrane (512) of the reservoir space (513) via an intermediate piece. The coupling may be carried out by gluing, welding or vulcanization or another joining technique or form of coupling. A change in the position of the connecting rod (515) may bring about a change in the reservoir space (513) whereby the chamber space (215) of the at least one expandable unit (21) may change. The reservoir space (513) may be larger than the chamber space (215). The motor unit may be operated by means of the energy store contained in the supply unit to supply energy to the implant.

Figure 16:
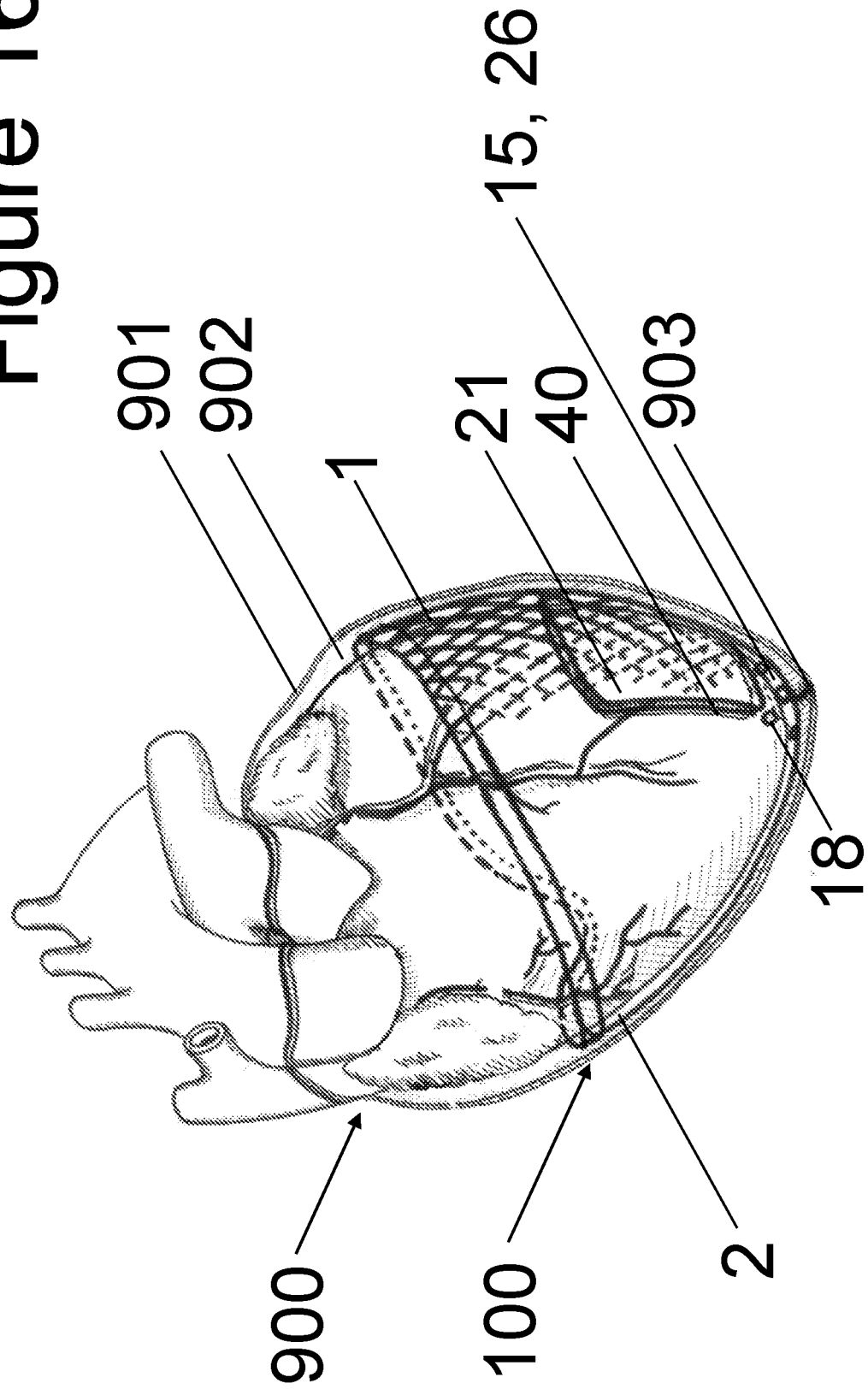
FIG. 16 shows a fully implantable embodiment of the device without a cable harness or supply unit.

FIG. 16 shows an embodiment of the implant (100) which may consist only of the frame structure (1), at least one sleeve (2), the at least one expandable unit (21) and at least one substance carrier (40) with at least one substance. The implant may therefore be implanted entirely into the body or into the pericardial cavity (902) through a surgical opening (903) made in the pericardium (901) without any outlet through an artificial body opening, a pericardium sluice or a cable harness having to be produced. An advantage of this embodiment is the lower risk of infection by avoiding any artificial body opening, its simple implantability because the pericardium may be stitched together again, and the simple structural form which may be material-saving and cost-saving.

The at least one expandable unit (21) may, for example, be a pneumatic unit in the form of a patch that may be filled with a fluid and that may have static pressure exerted upon it. As a result, constant contact between the surface of the heart and the at least one substance carrier (40) mounted on the at least one expandable unit (21) may be guaranteed. Alternatively, the expandable unit (21) may also be designed as a sponge or with the aid of a spring, for example made of nitinol, and may be set to specific degree of expansion by means of this spring.

The at least one sleeve (2) may have at least one opening (26) by means of which the exchange of liquid within the pericardial cavity (902) may be guaranteed. The frame structure (1) may also have an opening (15) coincidentally with the sleeve (2).

The frame structure (1) may have at least one coupling point (18) at the end near to the apex of the heart which may be removed minimally invasively from body with a set of explantation instruments suitable for the purpose or an explantation device similar to the one described in a previous section.

Further embodiments entirely implantable into the body may consist of only a frame structure (1) with at least one expandable unit (21) and/or only at least one substance carrier (40) with at least one substance without the implant comprising a sleeve (2). Yet further embodiments may consist of a sleeve (2) with at least one expandable unit (21) and/or only at least one substance carrier (40) with at least one substance without the implant comprising a frame structure (1). In this case, the wall thickness of the sleeve (2) may be arranged to be so thick that the sleeve (2) alone without the frame structure (1) is sufficiently stiff to remain in the body in the correct fit. For example, such a sleeve (2) may be made out of silicone with a wall thickness of 0.5 mm to 5 mm, or a wall thickness of 1 mm to 3 mm.

In some embodiments, the implant (100) may be made in at least one part out of at least one biodegradable material. An advantage of the embodiment of part of the implant (100) made of a biodegradable material, for example in the case of a biodegradable frame structure (1), is the easier removal from the body because the stiff frame structure (1) no longer has to be removed from the body. An advantage of an implant (100) made entirely out of biodegradable material is that there is no longer any need for explantation.

FIG. 17 shows geometries of the frame structure (1) which may be designed such that pointed and sharp-edged parts of the frame structure (1), which are often located at ends (19) of the frame structure (1), increase the risk of penetration through the sleeve at least partially surrounding the frame structure (1) or of damage to the body tissue.

FIG. 17 shows various embodiments of end fittings (60) which may serve to cover pointed or sharp-edged parts of the frame structure (1). This may be advantageous because the risk of penetration by the frame structure (1) through the sleeve pulled over it (not shown) may thereby be minimized. Moreover, the risk that parts of a potentially pointed or sharp-edged geometry of the frame structure (1) will damage body tissue may be removed.

FIG. 17*a* shows the geometry of a frame structure (1) over which end fittings (60) may be pulled. These end fittings (60) may consist of an elastic, preferably soft material. The end fittings (60) may consist of a plastic or a polymer. For example, the end fittings (60) may consist of silicone or polyurethane. The end fittings (60) may also consist of materials other than silicone or polyurethane. The end fittings (60) may alternatively consist of a plastic foam. The aim of the end fitting (60) is to prevent penetration by the frame structure (1) through the sleeve pulled over it and/or damage caused to body tissue by the frame structure (1).

The end fittings (60) may be coupled to the frame structure (1). Coupling options are, for example, non-positive, materially bonded and/or positive connections. The end fittings (60) may, for example, be glued to the frame structure (1). They may be stuck to the frame structure (1). However, they may also be stuck together through an opening in the frame structure (1). Alternatively, fixing may also be carried out with the aid of pins or buttons (602). For a connection with buttons, the at least two complementary coupling points (601) required for this purpose may be part of the end fitting (60). Alternatively, an end fitting (60) may also only be placed at the corresponding point on the frame structure (1) and then coupled to the sleeve, for example stuck.

The end fittings (60) may have at least one cavity (603) which may be suitable for feeding in part of the frame structure (1). As a result, the retention of an end fitting (60) on the frame structure (1) may be improved.

FIG. 17b shows a further embodiment of an end fitting (60) which may be laid in the form of an at least partial ring over at least part of the circumference of the frame structure (1). The material of the end fitting (60) may be considerably elastically deformable and flexible so that it may be converted, when inserting or removing the implant, from an expanded into a non-expanded state and vice versa without being damaged itself and without damaging other components or any body tissue.

FIG. 17c shows a geometry of the frame structure (1) together with an associated end fitting (60) in which, through appropriate cutting of the initial geometry, the slotted tube (20), an atraumatic form may be produced. This form minimizes the risk of body tissue injury through penetration, impaling, cutting or scratching by the frame structure (1) and the risk of the frame structure (1) breaking through the at least one sleeve surrounding the frame structure (1). The cutting may, for example, be designed such that the respective last slots on at least one end (19) of the slotted tube are arranged such that there is no longer any material connection between the struts protruding through the slots. Free-standing ends may therefore be produced. Upon widening of the structure, during the course of which the expanded geometry (as described in a previous section) is established through heat treatment, the free-standing ends of the frame structure (1) may be deformed such that the established geometry at the ends in the expanded state is curved so that these ends take on an atraumatic form. In addition, these already atraumatically formed ends may also be covered and secured with end fittings (60) of suitable shape. The risks described above may therefore be further reduced.

FIG. 18 shows a step during the removal of the implant (100) from the body. An embodiment of the explantation device (70) may consist of a cylindrical explantation tube (701). The explantation tube (701) has a proximal end facing the operator and a distal end which is inserted into the patient. The cylindrical explantation tube (701) has a radial widening at the distal end. The explantation device (70) may also consist of a traction element (704) with an external thread with a clamp (705) at the distal end of the traction element (704), an end fitting (702) with an axial bore and a nut (703).

As shown in FIG. 18, thoracotomy or a mini-thoracotomy allows access to the implanted device. The sealing of a pericardium opening (903) guaranteed by a pericardium sluice (3) may be removed in order to position the explantation device. The pericardium sluice (3) may remain in its position in the body here as it does not obstruct the explantation process. Alternatively, the pericardium sluice (3) may be removed as it is not otherwise required for the explantation. At least part of the cable harness (4) may be separated off to facilitate the procedure, for example by cutting away or clipping off. For explantation of the implant (100), the explantation tube (701) may first be inserted into the body so that the distal end of the tube is located inside the pericardial cavity and/or, if there is one, a pericardium sluice (3). The cable harness (4) leading away from the implant (100) or the remaining part of a separated cable harness (4) may be passed through the inside of the explantation tube (701). A fraction element (704) may be passed into the explantation tube (701) from outside. The traction element (704) may have an inner lumen through which at least part of the cable harness (4) may be passed. The traction element (704) may comprise a thread, for example an external thread. At the front end of the traction element (704) there may be a clamp (705) which at least partially surrounds the cable harness (4) and may be firmly coupled to the cable harness (4). Alternatively to the clamp (705) on the cable harness (4), a clamping device may also be located on the traction element (704), it being possible for this clamping device to be coupled to the fixing sleeve (41) of the cable harness (4). The traction element (704) and the clamp (705) may be two or more parts, but may also consist of just one part. The explantation device (70) may also comprise an end fitting (702) with an opening, for example a bore, which may be placed at the proximal end of the explantation tube (701). The end fitting (702) may be coupled to the explantation tube (701), for example with the aid of a centring pin (706), such that the end fitting (702) cannot be twisted towards the explantation tube (701). The traction element (704) may be fed through the opening in the end fitting (702). The traction element (704) and the end fitting (702) may be secured against twisting towards one another. The explantation device may also contain a nut (703), for example a milled nut, which has an internal thread which may be brought into engagement with the external thread of the traction element (704). By turning the nut (703), a tensile force may be exerted on the traction element (704) here which is in turn coupled to the cable harness (4)/the implant (100) and which serves to pull the implant (100) into the explantation tube (701). The advantage of this explantation device (70) is that the tensile force required is exerted by the nut (703), the fraction element (704) and the clamp (705) on the implant (100) and the counterforce is applied as compressive force by the implant (100) on the explantation tube, the end fitting (702) and the nut (703). The explantation device (70) is therefore outwardly force-free, that is to say no forces are exerted on the heart or the body of the patient during explantation (for example for support or the like). When the implant (100) is then located far enough inside the explantation tube (701), the entire explantation device (70) together with the implant (100) may be removed from the body. The pericardium and the thoracotomy required for explantation may then be suitably closed.

As shown in FIG. 18, the distal end of the explantation tube (701) may be fed through the pericardium sluice (3) into the pericardial cavity. The inside of the explantation tube (701) defines the explantation channel into which the implant (100) is at least partially pulled during explantation. For the purposes of explantation, the implant (100) may be converted into a compressed state. The explantation tube (701) may have a radial, funnel-shaped widening at the distal end. This widening allows explantation of the implant (100) with low risk of injury because, for example, parts of the implant (100) are prevented from catching, jamming and/or becoming blocked at the distal end. The widening may also serve to compress the implant (100) in a defined manner when it is pulled into the explantation tube (701). The angle of opening of the radial widening may be between 0° and 150°, between 10° and 90° or between 20° and 60°. The length of the explantation tube (701) may be between 4 cm and 40 cm, or between 6 cm and 25 cm. The length of the explantation tube (701) may be chosen so that the implant (100) may be partially or entirely accommodated in the tube in the compressed state. The internal diameter of the explantation tube (701) may be between 2 cm and 5 cm, or between 3 cm and 4 cm. The wall thickness of the explantation tube (701) may be between 0.1 mm and 3 mm, or between 0.5 mm and 1.5 mm. The wall thickness may decline towards the distal end of the explantation tube (701) in order to facilitate the pulling of the implant (100) into the explantation tube (701). The clamp (705) may be designed as at least a single part. However, it may also be designed to be multi-part so that it may be laid around the cable harness (4) or the fixing sleeve. The internal diameter of the clamp (705) may be at least as large as the external diameter of the cable harness or of the fixing sleeve. The internal diameter of the clamp (705) may be variable. The clamp (705) may be designed similarly to a hose clamp. For example, a clamp (705) may be used which has an internal diameter that is larger than the external diameter of the cable harness (4) or of the fixing sleeve so that the clamp (705) can easily be fed over the cable harness (4) or the fixing sleeve. As soon as the clamp (705) is then able to sit in the sought position, the internal diameter may then be reduced in order to couple the clamp (705) to the cable harness (4)/to the fixing sleeve, for example similarly to the functional principle of a hose clamp. By reducing the diameter, the seating and the slip resistance of the clamp (705) in relation to the cable harness (4)/the fixing sleeve to be gripped may be increased. An additional improvement in relation to seating and the slip resistance may be achieved by structuring the internal wall of the clamp (705), for example in the form of teeth, prongs or grooves. The wall thickness of the clamp (705) may be between 0.1 mm and 2 mm, or between 0.3 mm and 1 mm. In the embodiment shown in FIG. 18, the clamp (705) and the traction element (704) are designed as one part. Alternatively, the traction element (704) with the clamp (705) may be designed similarly to a collet through which the cable harness (4) may be fed. The longitudinal fraction element (704) with the clamp (705) may have at least one slot in the longitudinal direction starting at the distal end here, the slot extending over at least a quarter of the total length of the traction element (704). The external diameter of the traction element (704) in the slotted area may increase towards the distal end here so that the slotted area of the fraction element (704) is compressed upon screwing into the end fitting (702) and, for example, the cable harness (4) or the fixing sleeve is clamped. This embodiment has the advantage that the clamp (705) does not have to be manually clamped to part of the implant (100) by the operator because a clamp (705) in the form of a collet automatically compresses as soon as the slotted area of the traction element (704) with an increasing external diameter is compressed by the end fitting (702) of the explantation device (70). The further the slotted traction element (704) is screwed into the end fitting (702) here, the greater the clamping force may become.

The aim of the end fitting (702), amongst other things, is to prevent any relative twisting of the explantation tube (701) and traction element (704) with respect to one another and to convert a turning of the nut (703) into a translational movement of the fraction element (704), for example, by means of a tongue-and-groove connection, as shown in FIG. 18, in which the traction element (704) has a longitudinal groove into which a nib of the end fitting (702) engages. Alternatively, the end fitting (702) may, instead of a nib, also have a slot nut or a different guide element. The end fitting (702) may not twist towards the explantation tube (701) either. Without the end fitting (702), the turning of the nut (703) could cause a twisting of the traction element (704) which could cause a twisting of the implant (100) and possible injury of the patient. The end fitting (702) is designed as at least a single part. However, it may also be designed to be multi-part so that it may more easily be laid around the cable harness (4). The end fitting (702) may be coupled to the proximal end of the explantation tube (701), for example through centred positioning, screwing or a bayonet catch. In the embodiment of the explantation device (70) shown, the clamp (705) with the traction element (704) protrudes through the centric axial bore of the end fitting (702). The coupling of the end fitting (702) to the explantation tube (701) may be secured against the relative twisting of the explantation tube (701) and end fitting (702), for example through a centring pin, a splint, a screw, a bolt or a groove into which an engagement element may be coupled. The diameter of the centric axial bore may be of the order of size of the external diameter of the traction element (704). The external diameters of the end fitting (702) shown in the drawing are similar to the diameters of the explantation tube (701) such that a secure seating of the end fitting (702) on the explantation tube (701) is guaranteed. The turnable nut (703) may now be screwed onto the cable harness clamp. As soon as the nut (703) comes into contact with the end fitting (702), the implanted device (consisting of the fixing sleeve, the frame structure, the sleeve located therein, the expandable units, lines, sensors, etc.) may be pulled out of the pericardium through successive turns on the nut (703). The external diameter of the nut (703) should allow the comfortable operation of the explantation device (70) so that an adult is able to grip at least half of it with one hand. The external diameter of the nut (703) may be between 3 cm and 15 cm, or between 6 cm and 12 cm. The height of the nut (703) may be between 5 mm and 50 mm, or between 10 mm and 30 mm. The thread which allows the explantation should be designed such that the implant (100) may be removed by means of a number of turns of the milled nut that is reasonable for the operator. The thread may be a single- or multi-start thread. By using a multi-start thread, the thread pitch may be increased, whereby each turn of the nut (703) transmits a greater translational movement to the fraction element (704). The thread may be a transmission thread, for example a trapezoidal thread. Transmission threads, unlike fastening threads, have the advantage that the frictional forces are lower and/or no self-retention occurs, so the nut (703) may be turned more easily by the operator than in the case of a fastening thread (such as a metric or imperial coarse-pitch thread). The explantation using the present embodiment of an explantation device (70) has the advantage that the screwing mechanism allows gradual explantation that does not rely on large translational movements of the explantation device (70), which in turn reduces the trauma for the patient.

Alternatively to the explantation process described above, the cable harness (4) may also be cut at the ends of the extension struts. In the case of embodiments of the implant (100) in which the extension struts, as described in a previous section, have hooks, eyelets, loops or angled ends at their ends, the implant (100) may be pulled out thereon. An embodiment of the explantation device (70) may be used for that purpose which alternatively or in addition to the clamp (705) on the traction element (704) also has cable controls, wires and/or levers. The cable controls, cables or levers may be part of the traction element (704) or be coupled to the traction element (704). At the other end, the cable controls, cables and/or levers of the explantation device (70) may be coupled to the hooks, eyelets, loops or angled ends of the extension struts. As a result, the implant (100) may, as before in the previous embodiments, be pulled at least partially into the explantation tube (701) and conveyed out of the pericardium and out of the body of the patient.

In general terms, embodiments of the explantation device (70) may be designed such that they make an embodiment of the implant (100) easier to explant out of the pericardium by returning it to its non-expanded state.

In the case of embodiments of the implant (100) in which the implant (100) without any pericardium sluice (3), cable harness (4) or supply unit is inserted entirely into the pericardial cavity (902), the at least one traction element (704) may, instead of a clamp (705), have a coupling option at its distal end which is complementary to the at least one coupling option provided for the explantation on the frame structure (1) of the implant (100). The coupling may, for example, be designed as a hook-eyelet connection. Other embodiments of the coupling are also conceivable. A more precise description of an implant (100) which may be implanted into the pericardial cavity (902) entirely is described in more detail in a previous section.

Certain aspects of the invention may be formulated as the following embodiments:

In one aspect, a device supporting the function of a heart is described which comprises a frame structure and a sleeve with at least one expandable unit. The frame structure can comprise at least one extension strut. The frame structure can alternatively or in addition have a recess at its upper edge which is shaped such that the frame structure does not come into contact with the vena cava inferior or any other anatomical structure. The sleeve can also have a recess whose shape, size and position can substantially coincide with the recess of the frame structure.

In another aspect, a device supporting the function of a heart is described which comprises a frame structure, which can undergo transition from a non-expanded state to an expanded state. The frame structure can be self-expanding and can be inserted into a delivery system in its non-expanded state, and can at least partially envelope a heart in its expanded state. The frame structure can have a recess at its upper edge, the recess being shaped such that the frame structure in its implanted state does not compromise the inferior vena cava or any other anatomical structure. The recess can have a length along the upper edge of the frame structure of 2 cm, 3 cm, 4 cm, 5 cm, 6 cm, 7 cm or more. The recess can have a depth between 1 mm and 40 mm, in particular between 3 mm and 15 mm. The recess can be curved, semicircular, rectangular or polygonal. The frame structure can further comprise at least on extension strut, in particular two, three, four, five, six or more extension struts. The at least one extension strut can be part of the frame structure, in particular the extension of a wire mesh or the extension of a strut of a latticework. The at least one extension strut can be coupled to the frame structure. The at least one extension strut can have a length of between 1 cm and 10 cm, in particular between 4 cm and 7 cm. The sleeve can comprise a recess whose shape, size and position can substantially coincide with the recess of the frame structure.

What is claimed is:

1. A device for administration of a substance to a surface of a heart of a patient, comprising:
    a heart-shaped self-expanding unit, comprising
        a frame structure for at least partially encircling a circumference of the heart, the frame structure comprising
            a flexible ring structure comprising a single wire formed to follow a periodic, alternating course, wherein the flexible ring structure defines a circumference of an upper edge of the heart-shaped self-expanding unit, and
            a recess in the flexible ring structure dropping beneath the upper edge of the heart-shaped self-expanding unit toward an apex of the heart and defining a break in the circumference of the upper edge of the heart-shaped self-expanding unit, wherein
                the recess defines an open region extending from below the upper edge of the heart-shaped self-expanding unit and through the upper edge of the heart-shaped self-expanding unit, wherein the open region corresponds to an anatomical structure of the heart,
        a sleeve coupled to the frame structure and sized to fit about the apex and at least a portion of ventricles of the heart, wherein the sleeve comprises an internal contour that corresponds to a natural outer contour of the heart of the patient, and
        a plurality of expandable chambers configured to selectively apply pressure to the heart via hydraulic or pneumatic actuation, wherein
            the heart-shaped self-expanding unit is configured for introduction into a pericardium of the patient in a collapsed state, wherein
                the heart-shaped self-expanding unit automatically transforms from the collapsed state to an expanded state upon release in the pericardium of the patient; and
    a substance carrier for delivering the substance, wherein the substance carrier is coupled to the heart-shaped self-expanding unit.

2. The device of claim 1, wherein:
the substance carrier comprises a pocket; and
the substance is inserted into the pocket.

3. The device of claim 2, wherein the pocket comprises a removable area on a surface of the pocket facing the heart.

4. A heart-shaped self-expanding unit, comprising:
    a flexible ring structure for at least partially encircling a circumference of a heart, the flexible ring structure defining a circumference of an upper edge of the heart-shaped self-expanding unit, the flexible ring structure comprising
        a single wire formed to follow a periodic, alternating course at least partially encircling the circumference of the heart, and
        a recess in the flexible ring structure dropping beneath the upper edge of the heart-shaped self-expanding unit toward an apex of the heart and defining a break in the circumference of the upper edge of the heart-shaped self-expanding unit defined by the flexible ring structure, wherein
            the recess defines an open region extending from below the upper edge of the heart-shaped self-expanding unit and through the upper edge of the heart-shaped self-expanding unit, wherein the open region corresponds to an anatomical structure of the heart;
    a sleeve coupled to the flexible ring structure and sized to fit about the apex and at least a portion of ventricles of the heart, wherein the sleeve comprises an internal contour that corresponds to a natural outer contour of the heart of a patient; and
    a plurality of expandable chambers configured to selectively apply pressure to the heart via hydraulic or pneumatic actuation;
    wherein the heart-shaped self-expanding unit is configured for introduction into a pericardium of the patient in a collapsed state; and wherein the heart-shaped self-expanding unit automatically transforms from the collapsed state to an expanded state upon release in the pericardium of the patient.

5. The heart-shaped self-expanding unit of claim 4, wherein the single wire is composed of a polymer material.

6. The heart-shaped self-expanding unit of claim 5, wherein the polymer material of the single wire is a polyurethane material.

7. The heart-shaped self-expanding unit of claim 4, further comprising at least one sensor configured to detect at least one parameter of the heart.

8. The heart-shaped self-expanding unit of claim 7, wherein a first sensor of the at least one sensor is an electrode.

9. The heart-shaped self-expanding unit of claim 7, wherein the at least one sensor comprises a pressure sensor.

10. The heart-shaped self-expanding unit of claim 4, further comprising a substance carrier for delivering a substance, wherein the substance carrier is coupled to the sleeve.

11. The heart-shaped self-expanding unit of claim 10, further comprising at least one sensor configured to detect at least one parameter of the substance or the substance carrier.

12. The heart-shaped self-expanding unit of claim 4, wherein introducing the heart-shaped self-expanding unit into the pericardium of the patient comprises delivering the heart-shaped self-expanding unit into the pericardium via a delivery tube.

13. The heart-shaped self-expanding unit of claim 12, wherein the delivery tube is cylindrical.

14. The heart-shaped self-expanding unit of claim 4, wherein an amplitude of the periodic, alternating course is configured to assist in automatically transforming the heart-shaped self-expanding unit from the collapsed state to the expanded state.

15. The heart-shaped self-expanding unit of claim 4, wherein the sleeve is composed of a polymer material.

16. The heart-shaped self-expanding unit of claim 15, wherein the polymer material of the sleeve is a polyurethane material.

17. The heart-shaped self-expanding unit of claim 4, wherein each chamber of the plurality of expandable chambers is composed of a polymer material.

18. The heart-shaped self-expanding unit of claim 17, wherein the polymer material of each chamber of the plurality of expandable chambers is a polyurethane material.

19. The heart-shaped self-expanding unit of claim 4, wherein the sleeve forms at least a portion of each chamber of the plurality of expandable chambers.

20. The heart-shaped self-expanding unit of claim 4, wherein the sleeve is coupled to the flexible ring structure through welding.

21. The heart-shaped self-expanding unit of claim 4, wherein the periodic, alternating course has a sinusoidal form.

* * * * *